(12) United States Patent
Cooper et al.

(10) Patent No.: US 10,882,862 B2
(45) Date of Patent: Jan. 5, 2021

(54) COMPOSITIONS, METHODS, AND KITS FOR QUANTIFYING METHOTREXATE

(71) Applicant: Micromass UK Limited, Wilmslow (GB)

(72) Inventors: Donald Peter Cooper, Macclesfield (GB); Billy J. Molloy, Stockport (GB)

(73) Assignee: Micromass UK Limited, Wilmslow (GB)

( * ) Notice: Subject to any disclaimer, the term of this patent is extended or adjusted under 35 U.S.C. 154(b) by 101 days.

(21) Appl. No.: 16/305,150

(22) PCT Filed: Jun. 5, 2017

(86) PCT No.: PCT/GB2017/051620
§ 371 (c)(1),
(2) Date: Nov. 28, 2018

(87) PCT Pub. No.: WO2017/208033
PCT Pub. Date: Dec. 7, 2017

(65) Prior Publication Data
US 2020/0216453 A1    Jul. 9, 2020

Related U.S. Application Data

(60) Provisional application No. 62/345,511, filed on Jun. 3, 2016.

(51) Int. Cl.
*C07D 475/08* (2006.01)
*G01N 30/06* (2006.01)
*G01N 30/72* (2006.01)
*G01N 30/86* (2006.01)

(52) U.S. Cl.
CPC ......... *C07D 475/08* (2013.01); *G01N 30/06* (2013.01); *G01N 30/7233* (2013.01); *G01N 30/86* (2013.01)

(58) Field of Classification Search
CPC .................................................. C07D 475/08
See application file for complete search history.

(56) References Cited

FOREIGN PATENT DOCUMENTS

WO    2012/170549 A1    12/2012

OTHER PUBLICATIONS

Przybylski M: "Identification of Metabolism Pathways of Anticancer Drugs by High-pressure Liquid Chromatograph in Combination with Field Desorption Mass Spectrometry", Arzneimittel Forschung. Drug Research, vol. 32, No. 9, 1982, pp. 995-1012, XP001525840, ISSN: 0004-4172 pp. 995-1004 compound 13C5-MTX; p. 1002, right-hand column, last paragraph; figure 7.
Den Boer E et al: "Measuring methotrexate polyglutamates in red blood cells: a new LC-MS/MS-based method", Analytical and Bioanalytical Chemistry, vol. 405, No. 5, 2012, pp. 1673-1681, XP035169495, ISSN: 1618-2650, DOI: 10.1007/S00216-012-6581-7 the whole document compound MTXPG1 13C5, 15N; p. 1674, left-hand column, last paragraph—p. 1675, right-hand column, last paragraph; figure 1.
M G Nair et al: "Synthesis of 14C-Methotrexate", Journal of Labelled Compounds and Radiopharmaceuticals, vol. XIii, No. 1, 1977, pp. 147-153, XP055392766, ISSN: 0362-4803, DOI: 10.1002/jlcr.2580130116 the whole document.
The International Search Report and the Written Opinion of the International Searching Authority; completed on Jul. 21, 2017; dated Aug. 1, 2017.

*Primary Examiner* — Bruck Kifle
(74) *Attorney, Agent, or Firm* — Womble Bond Dickinson (US) LLP; Deborah M. Vernon; Benedict L. Hanrahan

(57) ABSTRACT

The invention relates to stable, isotopically labeled compounds for use in mass spectrometry analysis for quantifying methotrexate in a sample. Exemplary compounds include isotopically labeled variants of methotrexate.

14 Claims, 18 Drawing Sheets

FIG. 3

| Data table (mass intensity) |
|---|
| 454 100 |
| 455 25.0744 |
| 456 4.0238 |
| 457 0.4838 |
| 458 0.047 |
| 459 0.0037 |
| 460 0.0002 |

Plot

COMPOSITIONS, METHODS, AND KITS FOR QUANTIFYING METHOTREXATE

CROSS-REFERENCE TO RELATED APPLICATIONS

This application is a National Stage Application of International Application No. PCT/GB2017/051620, filed Jun. 5, 2017, which claims the benefit of and priority to U.S. Provisional Application No. 62/345,511, entitled "Compositions, Methods, and Kits for Quantifying Methotrexate" filed on Jun. 3, 2016. Each of the foregoing applications is incorporated herein by reference in its entirety.

FIELD OF THE INVENTION

The invention relates generally to stable, isotopically labeled compounds and uses thereof for quantifying methotrexate in a sample by mass spectrometry.

BACKGROUND OF THE INVENTION

Mass spectrometry (MS) is a major discovery tool in the life sciences. By using this analytical technique it is possible to analyze the molecular composition of a sample by ionizing the sample or the analyte molecules contained in said sample and then measuring the mass-to-charge ratios of the resulting ions. The mass spectra obtained by an MS experiment are used to identify, characterize, and quantify the abundance of the analytes of interest. In particular, liquid chromatography-mass spectrometry (LC-MS) has recently been used for quantification of drugs and biologically active compounds, mostly because of the high selectivity, sensitivity, speed, and simplicity imparted by LC/MS/MS.

For quantification of methotrexate in a sample, it is generally necessary to first establish a calibration curve which represents the relationship between the analytical signal obtained from the particular analytical method used, e.g., peak area or peak height in MS spectra or in mass chromatograms, and the quantity of the methotrexate. Thus, prior to the analysis of a sample, the analytical signals of a series of calibration standards (e.g., isolated methotrexate in six different concentrations) have to be determined and this external calibration has to be done regularly (e.g., daily). However, this procedure reduces productivity, increases the costs per sample, and renders the analysis of just one sample inefficient. Accordingly, new efficient methods and compounds for analysis of methotrexate in a sample are needed in the art.

SUMMARY OF THE INVENTION

The invention provides compounds, compositions, kits, and methods for quantifying methotrexate in a sample by mass spectrometry without relying upon conventional calibration and its associated drawbacks and disadvantages.

In embodiments, the invention provides for MS analysis where there is a single sample including a first known quantity of a first calibrator and a second known quantity of a second calibrator, and where the first calibrator, the second calibrator, and the target analyte are each distinguishable within the single sample by mass spectrometry. This avoids the need for an external calibration. Thus, by using internal calibration it is possible that an analyte is quantified by performing a single analysis of one sample so that each analysis yields a result thereby increasing the productivity and decreasing the costs per sample.

In addition to eliminating the inefficiency of conventional calibration, the invention addresses the issue of matrix effects that pose a problem for using MS in the quantitative analysis of methotrexate in samples. For example, the matrix coextracted with methotrexate can alter the signal response, resulting in poor analytical accuracy, linearity, and reproducibility. Accordingly, samples of different individuals may not have identical behavior in the analytic system used and may differ from the behavior of the calibration standards. Thus, an exact analysis using the conventional methods requires the provision of a matrix-based calibration standard, e.g., matrix which is free of methotrexate and which contains the calibration standard. However, such methotrexate-free matrix can be difficult to obtain.

Further issues with such matrix-based calibrator standards include: (i) the requirement to obtain large quantities of methotrexate-free matrix in constant quality and composition; (ii) pathogen testing if the matrix is of human or animal origin; (iii) handling, storage and stability of the matrix; and (iv) handling, storage and stability of the calibrators in the matrix. Moreover, samples to be analyzed can be quite diverse in nature, for example, different bodily samples (e.g., hair and plasma). Thus, the matrixes of such diverse samples can also differ significantly, thereby requiring two different sets of calibration standards, one matched for the bodily sample and one matched for the environmental sample. Therefore, calibration standards and quantification methods that are applicable to a wide variety of samples, for example, samples which are relevant in the field of clinical chemistry (e.g., plasma for the quantification of a metabolite), environmental protection (e.g., sewage for the quantification of a pharmaceutical), or the food industry (e.g., retain sample for the study of a food sample, e.g., an edible product of animal or vegetable origin such as milk, bread, eggs, meat, or an extract thereof) are advantageous.

Accordingly, in one aspect, the invention provides calibrator compounds which can be used as internal calibrators when quantitating the amount of methotrexate in a sample. The internal calibrators include compounds which, with respect to chemical composition, structure and physicochemical properties, are similar to methotrexate but which are distinguishable from methotrexate based on the behavior of the internal calibrator and methotrexate in a mass spectrometer. For example, the calibrator compounds of the invention can be distinguishable from methotrexate based on differences in mass and/or fragmentation pattern. The difference in mass between the calibrator compounds and methotrexate originates from the presence of different isotopes in the calibrator compounds relative to methotrexate. In some embodiments, the internal calibrator compound is generally absent or in a negligible (or otherwise compensable) initial amount in the sample to be analyzed. In some embodiments, the natural abundance of the internal calibrator is below the detection limit of a mass spectrometer.

In exemplary embodiments, multiple calibrator compounds can be used together in the same sample for methotrexate quantification. In such embodiments, the multiple calibrator compounds are preferably distinguishable from methotrexate and from each other based on differences in mass and/or fragmentation pattern. For example, in one embodiment, four or more compounds (such as the first, second, third, or fourth internal calibrator and methotrexate; or the first, second, third, and fourth internal calibrators) can be distinguished from each other by a mass spectrometer due to differences in their mass (i.e., a difference in mass that can be resolved by a MS instrument, or at a given cutoff), fragmentation pattern, or combinations thereof. The difference in mass between the four compounds originates from the presence of different isotopes (e.g., low abundant isotopes in one of the four compounds vs. high abundant isotopes in the other of the four compounds).

The property of being distinguishable based upon the behavior in a mass spectrometer includes situations where four or more compounds (such as the first, second, third, or fourth internal calibrator and methotrexate; or the first, second, third, and fourth internal calibrators) can be distinguished from each other by a mass spectrometer due to differences in their mass (i.e., a difference in mass that can be resolved by a MS instrument, or at a given cutoff), fragmentation pattern, or combinations thereof. The difference in mass between these four compounds originates from the presence of different isotopes (e.g., low abundant isotopes in one of the four compounds vs. high abundant isotopes in the other of the four compounds).

The compounds can be distinguished from each other by a mass spectrometer due to differences in their fragmentation pattern. The calibrators and methotrexate can fragment during the mass spectrometric analysis essentially in the same way, thereby generating fragments similar in chemical composition and structure for isotopic analogs.

For example, the compounds (e.g., the first, second calibrators and methotrexate; the first, second, third, and fourth calibrators and methotrexate; etc.) can be distinguished from each other by a mass spectrometer due to differences in their mass (i.e., a difference in mass that can be resolved by a MS instrument, or at a given cutoff). The masses of the compounds (e.g., the first, second, third, and fourth calibrators and methotrexate) can differ in at least 1 (or 2, 3, 4, 5, . . . ) mass units.

In other respects, the internal calibrator compounds can mimic methotrexate such that at least one of the physicochemical properties of the internal calibrator is essentially identical to the corresponding physicochemical property of methotrexate. In various embodiments, the internal calibrator and methotrexate are effectively indistinguishable from each other by one or more techniques commonly used to process a sample prior to analysis in a mass spectrometer. For example, an internal calibrator and methotrexate can be indistinguishable on the basis of one or more of: solubility (in a solvent, e.g., water or an organic solvent, or a mixture of solvents), retention time (in a separation technique, such as liquid chromatography), affinity (e.g., to an antibody specific for methotrexate), dissociation constant, reactivity and/or specificity towards an enzyme (e.g., hydrolase, transferase).

In one aspect, the invention provides calibrator compounds that differ in mass and/or fragmentation pattern from methotrexate due to incorporation of carbon-13. Accordingly, in one aspect disclosed herein are compounds having the structure:

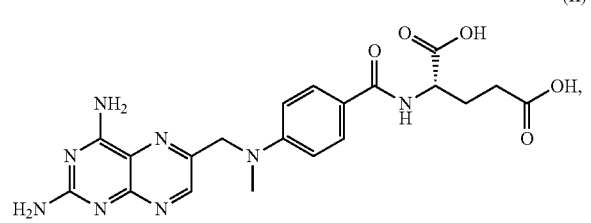

(II)

or a salt thereof, wherein each atom can be independently replaced with its corresponding stable isotope, which can be used as calibrators in compositions and kits for the mass spectrometry methods disclosed herein.

In another aspect, the invention provides calibrator compounds having the structure:

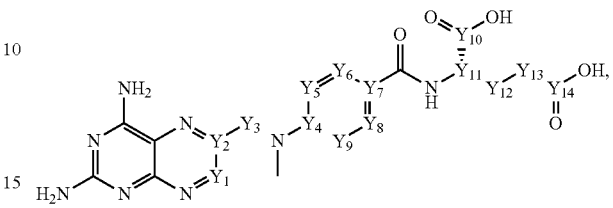

or a salt thereof; wherein each of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ is independently selected from carbon or carbon-13; and wherein at least 5 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In one embodiment, at least 5 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In another embodiment, at least 6 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In yet another embodiment, at least 7 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In still another embodiment, at least 8 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In another embodiment, at least 9 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In yet another embodiment, at least 10 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In another embodiment, at least 11 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In still another embodiment, at least 12 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In another embodiment, at least 13 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In yet another embodiment, all of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In another embodiment, 5 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In still another embodiment, 6 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In another embodiment, 11 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In yet another embodiment, 14 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13. In still another embodiment, at least 5 of $Y_4$, $Y_5$, $Y_6$, $Y_7$, $Y_8$, and $Y_9$, are carbon-13. In another embodiment, $Y_{10}$, $Y_{11}$, $Y_{12}$, $Y_{13}$, and $Y_{14}$ are carbon-13. In an exemplary embodiment at least $Y_1$, $Y_2$, and $Y_3$, are carbon-13.

In a specific embodiment, the calibrator compound has the structure:

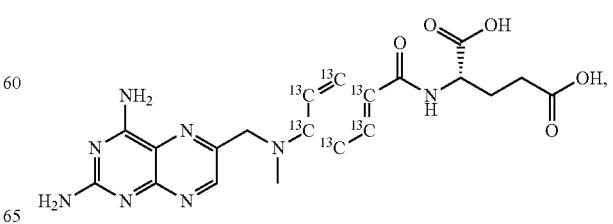

or a salt thereof.

In another embodiment, the calibrator compound has the structure:

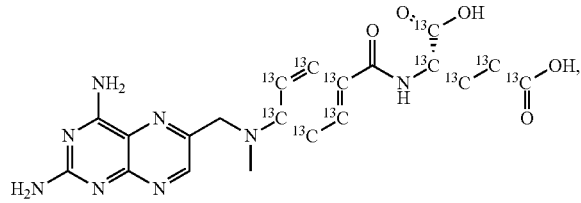

or a salt thereof.

In-yet another embodiment, the calibrator compound has the structure:

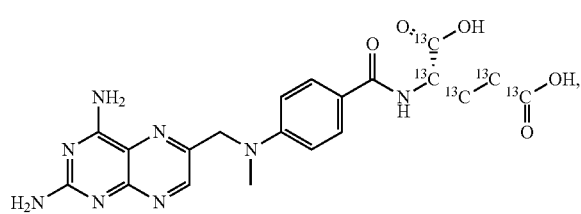

or a salt thereof.

In still another embodiment, the calibrator compound has the structure:

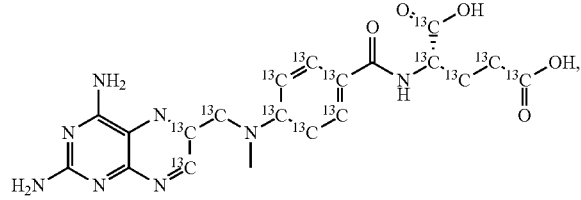 [SMILES: CN([13CH2][13CH]1[13CH]=Nc2nc(N)nc(N)c2N1)[13CH]1[13CH]=[13CH][13C](C(=O)N[13C@@H]([13CH2][13CH2][13C](=O)O)[13C](=O)O)=[13CH][13CH2]1]

or a salt thereof.

Compositions according to the invention can include a known quantity of one or more calibrators described herein; such as one or more of the compounds of the invention described above. For example, the invention provides compositions comprising a first known quantity of a first calibrator; a second known quantity of a second calibrator; optionally a third known quantity of a third calibrator; and optionally a fourth known quantity of a fourth calibrator. In another embodiment, each known quantity of the one or more calibrators is different from the known quantity of calibrators. In another embodiment, the calibrators and the methotrexate are each distinguishable in a single sample by mass spectrometry. Kits according to the invention can include any one or more of the foregoing compounds or compositions, together with instructions (and/or other/additional means) for implementing the methods described herein. In a particular embodiment, the compositions and kits of the invention comprise at least one compound selected from:

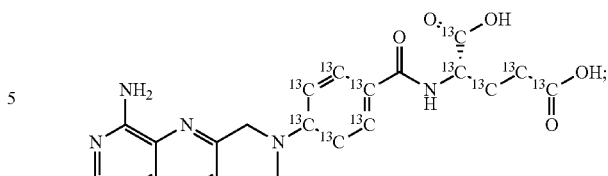

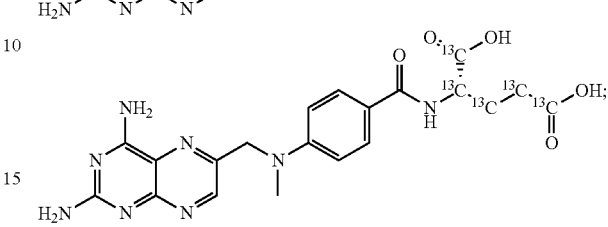

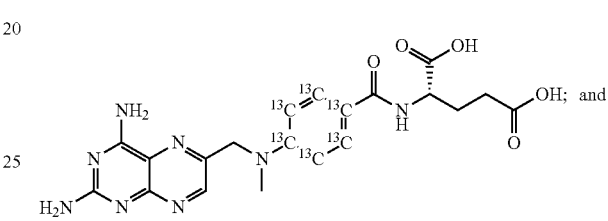

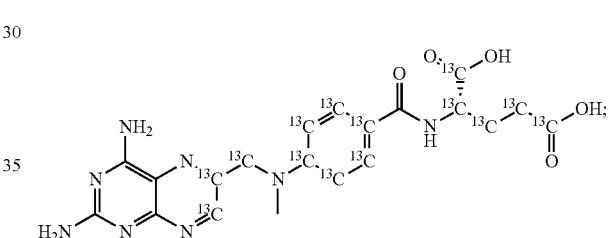

or a salt thereof, as the calibrator compound(s).

The invention also features methods for quantifying unlabeled methotrexate by mass spectrometry. In one embodiment, methods of quantifying methotrexate in a sample include providing a sample comprising providing a sample comprising a known quantity of a first calibrator, a known quantity of a second calibrator corresponding to a second compound, wherein the sample optionally comprises a third known quantity of a third calibrator corresponding to a third compound, a fourth known quantity of a fourth calibrator corresponding to a fourth compound, and unlabeled methotrexate, and wherein the first calibrator, the second calibrator, the third calibrator, the fourth calibrator, and the unlabeled methotrexate are each distinguishable in the sample by mass spectrometry; obtaining a mass spectrometer signal comprising a first calibrator signal, a second calibrator signal, and optionally comprising a third calibrator signal, a fourth calibrator signal, and an unlabeled methotrexate signal, from the sample; and quantifying the amount of unlabeled methotrexate in the sample using the first calibrator signal, the second calibrator signal, the third calibrator signal, the fourth calibrator signal, and the unlabeled methotrexate signal. In embodiments, the first calibrator, the second calibrator, the third (optional) calibrator, and the fourth (optional) calibrator are compounds having the structure selected from any one or more of the following:

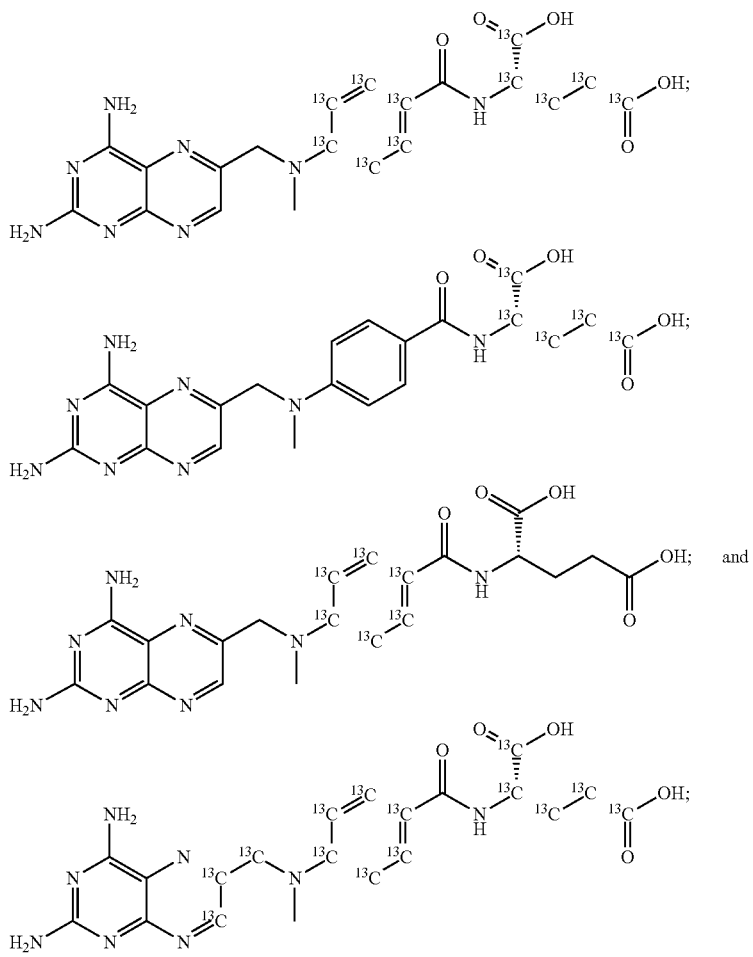

or a salt thereof. In exemplary embodiments, the calibrator compounds are distinguishable from each other and from unlabeled methotrexate using mass spectrometry. In one embodiment, the method preparing the sample by combining the known quantities of the calibrators in a single specimen potentially comprising the unlabeled methotrexate; and/or separating the calibrators, and the unlabeled methotrexate from other components of the sample prior to obtaining the mass spectrometer signal. In a particular embodiment, the method involves quantifying the unlabeled methotrexate by first, obtaining a calibration curve from the known quantities of the calibrators; and second, quantifying the unlabeled methotrexate using the calibration curve and the unlabeled methotrexate signal, or, alternatively, quantifying the unlabeled methotrexate algebraically using the signals of the calibrators and the unlabeled methotrexate signal.

In one embodiment, one of the calibrators used in the foregoing methods has the structure:

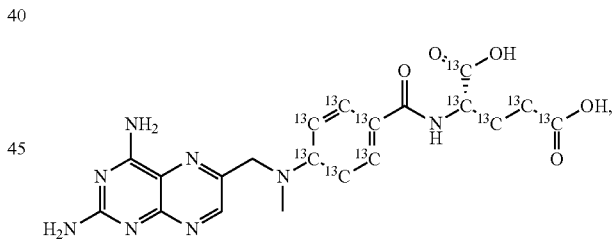

or a salt thereof.

In one embodiment, one of the calibrators used in the foregoing methods has the structure:

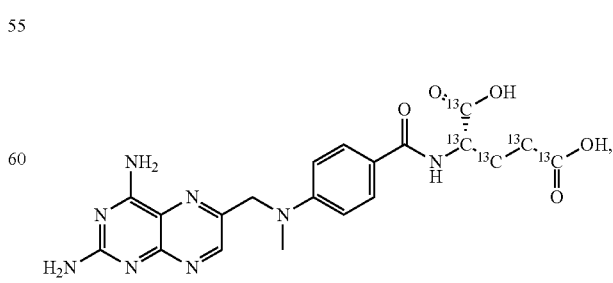

or a salt thereof.

In one embodiment, one of the calibrators used in the foregoing methods has the structure:
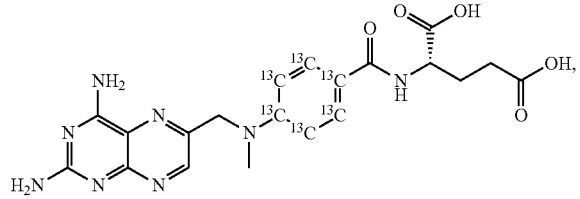
or a salt thereof.
In one embodiment, one of the calibrators used in the foregoing methods has the structure:
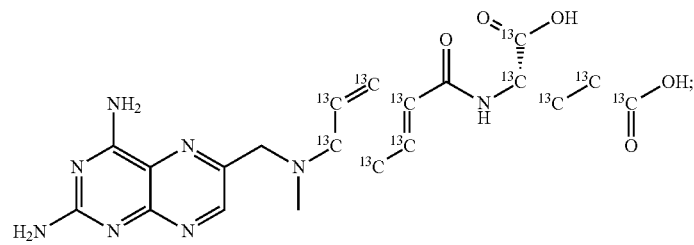
or a salt thereof.
In one embodiment, one of the calibrators used in the foregoing methods is selected from:
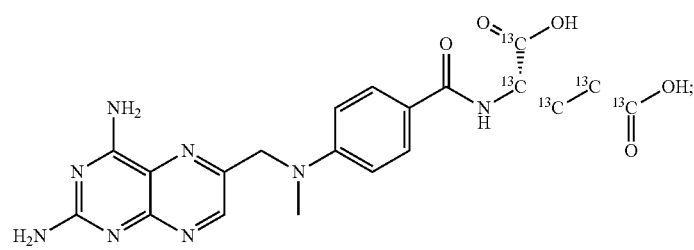
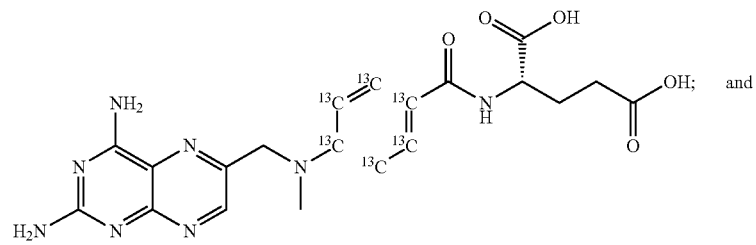
and
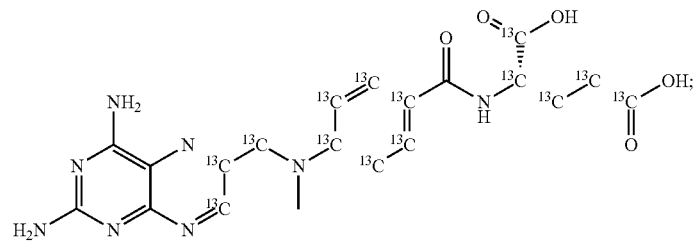
or a salt thereof.

The internal calibrator compositions, kits, and methods described herein are broadly applicable to a wide variety of samples, for example, samples which are relevant in the field of clinical chemistry (e.g., plasma for the quantification of a metabolite), environmental protection (e.g., sewage for the quantification of a pharmaceutical), and the food industry (e.g., an edible product of animal or vegetable origin such as milk, bread, eggs, meat, or an extract thereof). Furthermore, because internal calibrators are added to the sample to be analyzed, they can be processed in exactly the same way as methotrexate and thus, can be used to compensate for sample and/or methotrexate losses during sample preparation.

The materials, methods, and kits provided herein meet the need for efficient quantification of methotrexate in a small number of samples, (e.g., a single sample, or other instances in which the number of samples to be analyzed is smaller than the number of calibration standards). Furthermore, the invention also meets the need for calibration standards and quantification methods which are universally applicable to a wide variety of samples, for example, samples which are relevant in field of clinical chemistry (e.g., plasma for the quantification of a metabolite), environmental protection (e.g., sewage for the quantification of a pharmaceutical), and the food industry (e.g., an edible product of animal or vegetable origin such as milk, bread, eggs, meat, or an extract thereof). The invention meets these, and other needs by providing compositions including two, three, four (or more) compounds of the invention, which are used as internal calibrators, in differing concentrations that can be used to quantify methotrexate in a sample. The internal calibrators and methotrexate are distinguishable from each other based on their behavior in a mass spectrometer. Such calibration standards can be stable, easy to handle, and/or suitable for high-throughput analysis.

A further advantage of at least some of the embodiments of the present invention is that the calibration standards are present in exactly the same matrix as the target analyte and thus, each sample has its own perfectly matrix-matched calibration standards, thereby reducing or eliminating matrix effects. Another advantage of the present invention is reduced costs compared to conventional assays, multiplex capability, and the potential for decreasing time to result and increasing throughput, as compared to conventional methods.

Still another advantage of the present invention is improved specificity and sensitivity over conventional assays, such as an enzyme immunoassay for determination of methotrexate in human serum or plasma using automated clinical chemistry analyzers. Certain commercially available immunoassays for methotrexate detection (e.g., the ARK Methotrexate Assay, Ark Diagnostics, Inc.) are unsuitable for use with specimens obtained from patients who have received glucarpeptidase (carboxypeptidase G2) as a high dose methotrexate rescue therapy. These specimens have increased serum levels of 4-[[2,4-diamino-6-(pteridinyl) methyl]-methylamino]-benzoic acid (DAMPA) that result from metabolism of methotrexate by glucarpeptidase. DAMPA crossreacts with the methotrexate antibody used in this assay, and may continue to circulate for at least five to seven days before accurate measurements of serum methotrexate may return. In contrast, the present methods do not utilize a methotrexate antibody, thereby allowing for more accurate detection of serum methotrexate.

Other features and advantages of the calibrator compositions, methods and kits described herein are set forth herein.

BRIEF DESCRIPTION OF THE DRAWINGS

FIG. 3 shows an expanded view of the Data Table from FIG. 1 showing that the fifth isotope peak of methotrexate has an intensity of 0.0037% compared to the main peak.

In FIG. 4A both compounds are present at the same relative concentration. In FIG. 4B, unlabeled methotrexate is present at 1000 fold higher relative concentration to simulate the situation when a sample contains 10 μM methotrexate and the calibrator contains 0.01 μM $[^{13}C_5]$-methotrexate.

DETAILED DESCRIPTION

Figure 1:
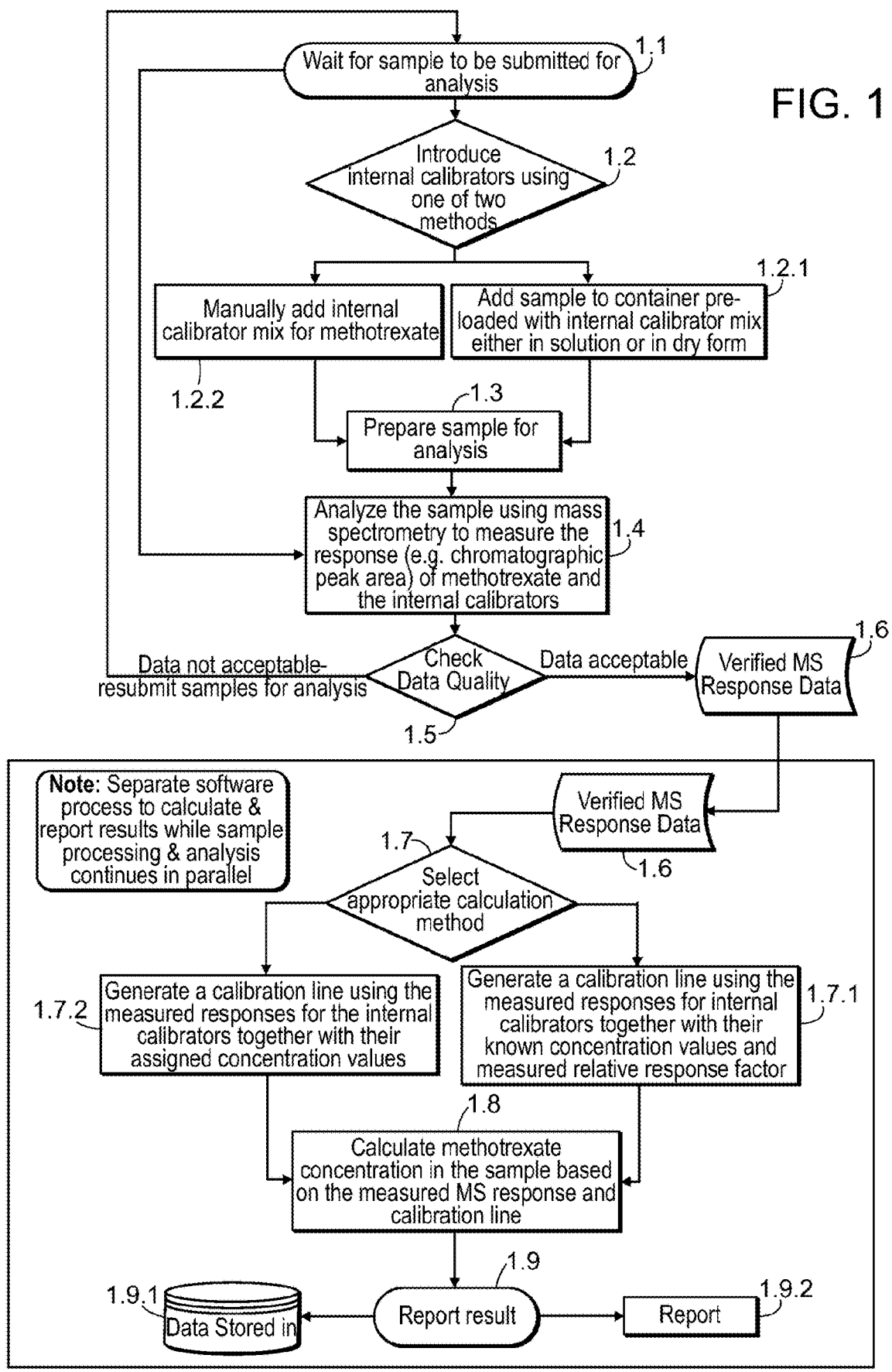
FIG. 1 illustrates an example method for quantifying a sample containing methotrexate.

The invention relates to compositions, kits, methods, and apparatuses for quantifying methotrexate in a sample. In one embodiment, the invention provides stable, isotopically labeled compounds for use in mass spectrometry analysis for quantifying a methotrexate in a sample. Structurally, methotrexate is shown below as the compound of formula (I).

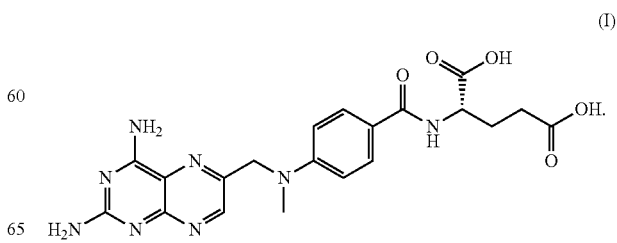

Definitions

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" refers to deuterium.

"$^{13}C$" refers to carbon-13.

"$^{15}N$" refers to nitrogen-15.

"$^{18}O$" refers to oxygen-18.

"Replaced with carbon-13" refers to the replacement of one or more carbon atoms with a corresponding number of carbon-13 atoms.

"Replaced with nitrogen-15" refers to the replacement of one or more nitrogen atoms with a corresponding number of nitrogen-15 atoms.

"Replaced with oxygen-18" refers to the replacement of one or more oxygen atoms with a corresponding number of oxygen-18 atoms.

Throughout this specification, a variable may be referred to generally (e.g., "each Y") or may be referred to specifically (e.g., $Y^{1a}$, $Y^4$, $Y^6$, etc.). Unless otherwise indicated, when a variable is referred to generally, it is meant to include all specific embodiments of that particular variable.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrometric instrument where, due to a combination of magnetic and electric fields, the ions follow a path in space that is dependent upon mass ("m") and charge ("z").

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include (but are not limited to) reverse phase liquid chromatography (RPLC), high performance liquid chromatography (HPLC), ultra-high performance liquid chromatography (UPLC or UHPLC), turbulent flow liquid chromatography (TFLC) (sometimes known as high turbulence liquid chromatography (HTLC) or high throughput liquid chromatography), and carbon dioxide based chromatograpy.

As used herein, the term "high performance liquid chromatography" or "HPLC" (also sometimes known as "high pressure liquid chromatography") refers to liquid chromatography in which the degree of separation is increased by forcing the mobile phase under pressure through a stationary phase, typically a densely packed column. As used herein, the term "ultra high performance liquid chromatography" or "UHPLC" (sometimes known as "ultra high pressure liquid chromatography") refers to HPLC that occurs at much higher pressures than traditional HPLC techniques.

The term "LC/MS" refers to a liquid chromatograph (LC) interfaced to a mass spectrometer. The term "LC/MS/MS" refers to a liquid chromatograph (LC) interfaced to an instrument that includes two mass-spectrometers.

Calibrators

The compounds disclosed herein may be used as internal calibrators in certain MS methods for quantifying methotrexate in a sample. Internal calibrators include compounds which are similar to methotrexate with respect to chemical composition (e.g., empirical formula), structure (e.g., atomic arrangement and bonding), and/or physicochemical properties, but which are distinguishable from methotrexate by behavior in a mass spectrometer. Exemplary calibrators disclosed herein have the same base structure as methotrexate, but differ slightly with respect to their molecular mass. A difference in composition and/or mass can result from replacement of an atom with a corresponding isotope of said atom (e.g. hydrogen is replaced with deuterium, carbon is replaced with carbon-13, etc.).

In other embodiments, a difference in composition and/or mass can result from (i) replacement of one group with a homologous group (e.g., a homologous group can have 1 carbon atom more or less (e.g., ethyl (ethylene) can be considered a homologue to methyl and propyl (methylene and propylene)); (ii) modification of a functional group (e.g., acetylation of an amino group; esterification; methylation; hydroxylation; hydration; biotinylation; cleavage of an amide, ester, thioester, acetal, ketal group; decarboxylation; demethylation; dehydration); and/or (iii) replacement of an atom with another atom of the same group of the period table of elements (e.g., replacement of one halogen with another).

Furthermore, the compounds disclosed herein can mimic methotrexate such that at least one of the physicochemical properties of the internal calibrator is essentially identical to the corresponding physicochemical property of methotrexate. Physicochemical properties can include any measurable property the value of which describes a physical and/or chemical state of a compound. For example, physicochemical properties include, but are not limited to, size, mass, absorbance, emission, electric charge, electric potential, isoelectric point (pi), flow rate (e.g., retention time), magnetic field, spin, solubility, viscosity, reactivity against or affinity to other substances (e.g., antibodies, enzymes), toxicity, chemical stability in a given environment, capability to undergo a certain set of transformations (e.g., molecular dissociation, chemical combination, redox reactions) under certain physical conditions in the presence of another chemical substance, polarity, and hydrophobicity/hydrophilicity.

In various embodiments, the compounds disclosed herein and methotrexate are effectively indistinguishable from each other by one or more techniques commonly used to process a sample prior to mass spectrometric analysis. For example, the compounds disclosed herein and methotrexate can be indistinguishable on the basis of solubility (in a solvent, e.g., water or an organic solvent, or a mixture of solvents), retention time (in a separation technique, such as liquid chromatography), affinity (e.g., to an antibody specific for said methotrexate), dissociation constant, reactivity and/or specificity towards an enzyme (e.g., hydrolase, transferase).

The compounds disclosed herein are generally absent, or present in a negligible (or otherwise compensable) initial amount in the sample to be analyzed. The compounds disclosed herein are generally synthetic compounds, e.g., compounds which do not naturally occur (e.g., in the sample), or the natural abundance of which is below the detection limit of a mass spectrometer. In one embodiment, the compounds disclosed herein are isotope-labeled analogues of methotrexate.

Isotopes relate to nuclides with the same number of protons but differing numbers of neutrons (i.e., they have the same atomic number and are therefore the same chemical element). Different isotopes of the same chemical element generally have essentially the same chemical characteristics and therefore behave essentially identically in chemical and/or biological systems. Therefore, isotope labeled analogs of methotrexate include compounds that are essentially identical to methotrexate in chemical composition and structure, with the exception that at least one atom of the methotrexate is substituted for an isotope thereof.

It will be recognized that some variation of natural isotopic abundance occurs in a synthesized compound depending upon the origin of chemical materials used in the synthesis. Thus, a preparation of methotrexate will inherently contain small amounts of isotopologues. The concentration of naturally abundant stable hydrogen, carbon, nitrogen, and oxygen isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

An isotope labeled analogue can replace between one and n atoms with isotopes, where n is the number of atoms in methotrexate. In various embodiments, isotope labeled analogs can include 1, 2, 3, . . . , n isotopic replacements, which can then form a set of internal calibrators. Preferably, each internal calibrator contains at least 5 isotopes. Most preferably, each internal calibrator contains at least 5 carbon-13 atoms. The isotope labeled analogues can vary by one or more (e.g., where more than one substitution is made between analogs and/or where the isotopes differ by more than one mass unit from the most common naturally occurring isotope) mass units. A given analogue should contain at least 50.1% incorporation of a given isotope at each position. Preferably, a given analogue is isotopically pure at each position.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

Similarly, unless otherwise stated, when a position is designated specifically as "C" or "carbon", the position is understood to have carbon at its natural abundance isotopic composition. Also unless otherwise stated, when a position is designated specifically as "$^{13}$C" or "carbon-13", the position is understood to have carbon-13 at an abundance that is at least 182 times greater than the natural abundance of carbon-13, which is 1.1% (i.e., at least 50.1% incorporation of deuterium).

Moreover, unless otherwise stated, when a position is designated specifically as "N" or "nitrogen", the position is understood to have oxygen at its natural abundance isotopic composition. Also unless otherwise stated, when a position is designated specifically as "$^{15}$N" or "nitrogen-15", the position is understood to have nitrogen-15 at an abundance that is at least 543 times greater than the natural abundance of nitrogen-15, which is 0.368% (i.e., at least 50.1% incorporation of deuterium).

Lastly, unless otherwise stated, when a position is designated specifically as "O" or "oxygen", the position is understood to have oxygen at its natural abundance isotopic composition. Also unless otherwise stated, when a position is designated specifically as "$^{18}$O" or "oxygen-18", the position is understood to have oxygen-18 at an abundance that is at least 979 times greater than the natural abundance of carbon-13, which is 0.204% (i.e., at least 50.1% incorporation of deuterium). The property of being distinguishable based upon behavior in a mass spectrometer includes situations where two or more compounds (such as the first and second internal calibrators; the first or second internal calibrator and methotrexate; or the first internal calibrator, second internal calibrator, and methotrexate, etc.) can be distinguished from each other by a mass spectrometer due to differences in their mass (i.e., a difference in mass that can be resolved by a MS instrument, or at a given cutoff) and/or fragmentation pattern.

For example, two compounds (e.g., the first internal calibrator and methotrexate) can be distinguished from each other by a mass spectrometer due to differences in their mass. The masses of the two compounds (e.g., the first internal calibrator and the methotrexate) can differ in at least 1 (or 2, 3, 4, 5, . . . ) mass units where the compounds are isotopic analogs. A difference in mass can be less than one mass unit, or a non-integer mass unit greater than one.

Depending upon instrument resolution and/or a desired resolution cutoff, a difference in mass can be a difference of +0.1, 0.01, 0.001, 0.0001, 0.0001 mass units. The difference in mass between these two compounds can originate from the presence of different isotopes (e.g., low abundant isotopes in one of the two compounds vs. high abundant isotopes in the other of the two compounds) and/or different chemical moieties.

Two compounds (e.g., the first internal calibrator and the methotrexate) can also be distinguished from each other by a mass spectrometer due to differences in their fragmentation pattern. The fragmentation pattern of a compound relates to the compound-specific set of fragments (e.g., product/daughter ions) generated in a mass spectrometer from the compound. The two or more compounds (e.g., a calibrator and corresponding methotrexate, two calibrators, etc.) can fragment during the MS analysis essentially in the same way, thereby generating fragments similar in chemical composition and structure. However, in some embodiments, the fragment generated from one compound (e.g., the calibrator) can differ from the corresponding structurally similar fragment generated by the other compound (e.g., the methotrexate) by a difference in mass that is resolvable by the instrument being used (or by a predetermined cutoff).

Internal calibrators can be selected, for example, according to the following general scheme: (a) subjecting a given methotrexate to fragmentation in a mass spectrometer in order to obtain its fragmentation pattern; (b) selecting a specific fragment of said fragmentation pattern; (c) designing an isotopically labeled fragment on the basis of the fragment selected in step (b) which differs from the fragment selected in step (b) by a resolvable difference in mass and which is distinguishable from the other fragments and ions of the fragmentation pattern obtained in step (a); (d) designing an isotopically-labeled internal calibrator which will produce said isotopically labeled fragment designed in step (c) in a mass spectrometer; and (e) preparing said isotopically-labeled internal calibrator.

Internal calibrators preferably contain a sufficient number of stable isotope labels to allow them to be differentiated from unlabeled methotrexate (and from each other) using a mass spectrometer. As described herein, unlabeled methotrexate has a characteristic isotope distribution due to the presence of low levels of naturally occurring isotopes in the molecule. Of the elements present in methotrexate ($C_{20}H_{22}N_8O_5$), carbon has the most abundant isotope in the form of carbon-13 ($^{13}C$), which accounts for approximately 1% of all naturally occurring carbon atoms. The presence of twenty carbon atoms in a methotrexate molecule provides an opportunity for the random occurrence of one or more $^{13}C$ atoms, each one causing an increase in the mass of the molecule by approximately 1 Dalton. Such random occurrence of one or more $^{13}C$ atoms in unlabeled methotrexate creates the potential for naturally occurring isotopes of unlabeled methotrexate to interfere internal calibrators.

As described herein, the fifth isotope peak of unlabeled methotrexate was determined by the inventors to have a sufficiently low relative intensity to allow unlabeled methotrexate to be readily distinguishable from internal calibrators comprising methotrexate having five or more stable isotope labels. Accordingly, in one embodiment, internal calibrators for quantifying methotrexate are selected to contain at least five stable isotope labels. In various embodiments, the calibrators are selected to contain five or more stable isotope labels, six or more stable isotope labels, seven or more stable isotope labels, eight or more stable isotope labels, nine or more stable isotope labels, ten or more stable isotope labels, eleven or more stable isotope labels, twelve or more stable isotope labels, thirteen or more stable isotope labels, fourteen or more stable isotope labels, fifteen or more stable isotope labels, sixteen or more stable isotope labels, seventeen or more stable isotope labels, eighteen or more stable isotope labels, nineteen or more stable isotope labels, or twenty or more stable isotope labels.

It may be possible, in some embodiments, to utilize internal calibrators having four stable isotope labels, although this may impact the dynamic range of the assay, due to the higher relative intensity of the fourth isotope peak of unlabeled methotrexate. Accordingly, in one embodiment, the calibrators are selected to contain at least four stable isotope-labels.

Compounds of the Invention

In some embodiments, the invention provides novel compounds that are useful for quantifying the amount of methotrexate in a sample by mass spectrometry disclosed herein is a compound having the structure of Formula (II):

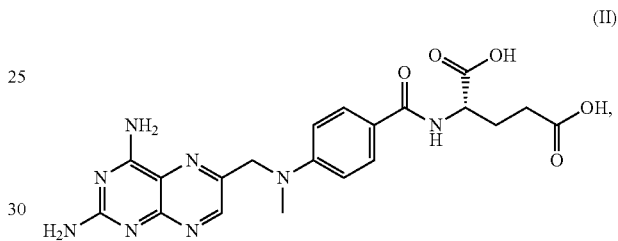

or a salt thereof, wherein each atom can be independently replaced with its corresponding stable isotope.

In a first embodiment, the compound has the structure of Formula (II), wherein the compound contains at least 5 stable isotopes; and wherein each stable isotope represents at least 50.1% incorporation of the isotope at each position. In some embodiments, the compound contains 5, 6, 7, 8, 9, 10, 11, 12, 13, 14, 15, 16, 17, 18, 19, 20, or more stable isotopes.

In a second embodiment, the compound has the structure of Formula (II), wherein each hydrogen can be independently replaced with deuterium (e.g., 1, 2, 3, 4, 5, 6, 7, 8, 9, 10, 11, 12, 13, 14, 15, 16, 17, 18, 19, 20, 21, or 22 deuterium atoms), each carbon can be independently replaced with carbon-13 (e.g., 1, 2, 3, 4, 5, 6, 7, 8, 9, 10, 11, 12, 13, 14, 15, 16, 17, 18, 19, or 20 carbon-13 atoms), each nitrogen can be can be independently replaced with nitrogen-15 (e.g., 1, 2, 3, 4, 5, 6, 7, or 8 nitrogen-15 atoms), or each oxygen can be independently replaced with oxygen-18 (e.g., 1, 2, 3, 4, or 5 nitrogen-15 atoms).

In a third embodiment, the compound has the structure of Formula (II), wherein the compound comprises at least 5 deuterium atoms, at least 5 carbon-13 atoms, at least 5 nitrogen-15 atoms, or at least five oxygen-18 atoms.

In fourth embodiment, the compound has the structure of Formula (II), wherein the compound comprises at least 5 carbon-13 atoms.

In fifth embodiment, the compound has the structure of Formula (II), wherein the compound has a mass difference of +5 to +20 with respect to the compound lacking incorporation of stable isotopes. Preferably, the compound has the structure of Formula (II), wherein the compound has a mass difference of +5 to +12 with respect to the compound lacking incorporation of stable isotopes.

In sixth embodiment, the compound has the structure of Formula (II), wherein the compound has a mass difference of +5 with respect to the compound lacking incorporation of stable isotopes.

In a seventh embodiment, the compound has the structure of Formula (II), wherein the compound has a mass difference of +6 with respect to the compound lacking incorporation of stable isotopes.

In an eighth embodiment, the compound has the structure of Formula (II), wherein the compound has a mass difference of +7 with respect to the compound lacking incorporation of stable isotopes.

In a ninth embodiment, the compound has the structure of Formula (II), wherein the compound has a mass difference of +8 with respect to the compound lacking incorporation of stable isotopes.

In a tenth embodiment, the compound has the structure of Formula (II), wherein the compound has a mass difference of +9 with respect to the compound lacking incorporation of stable isotopes.

In a twelfth embodiment, the compound has the structure of Formula (II), wherein the compound has a mass difference of +10 with respect to the compound lacking incorporation of stable isotopes.

In a thirteenth embodiment, the compound has the structure of Formula (II), wherein the compound has a mass difference of +11 with respect to the compound lacking stable incorporation of isotope labels.

In a fourteenth embodiment, the compound has the structure of Formula (II), wherein the compound has a mass difference of +12 with respect to the compound lacking incorporation of stable isotope labels.

In a fifteenth embodiment, the compound has the structure of Formula (II), wherein the compound has a mass difference of +13 with respect to the compound lacking incorporation of stable isotope labels.

In a sixteenth embodiment, the compound has the structure of Formula (II), wherein the compound has a mass difference of +14 with respect to the compound lacking incorporation of stable isotope labels.

In a seventeenth embodiment, the compound has the structure of Formula (II), wherein the compound has a mass difference of +15 with respect to the compound lacking incorporation of stable isotope labels.

In an eighteenth embodiment, the compound has the structure of Formula (II), wherein the compound has a mass difference of +16 with respect to the compound lacking incorporation of stable isotope labels.

In a nineteenth embodiment, the compound has the structure of Formula (II), wherein the compound has a mass difference of +17 with respect to the compound lacking incorporation of stable isotope labels.

In a twentieth embodiment, the compound has the structure of Formula (II), wherein the compound has a mass difference of +18 with respect to the compound lacking incorporation of stable isotope labels.

In a twenty-first embodiment, the compound has the structure of Formula (II), wherein the compound has a mass difference of +19 with respect to the compound lacking incorporation of stable isotope labels.

In a twenty-second embodiment, the compound has the structure of Formula (II), wherein the compound has a mass difference of +20 with respect to the compound lacking incorporation of stable isotope labels.

In a twenty-third embodiment, the compound has the structure of Formula (II), wherein 5 or more atoms in region A and/or 5 or more atoms in region B can be independently replaced with its corresponding stable isotope; wherein region A of the compound is represented by a fragment having the structure:

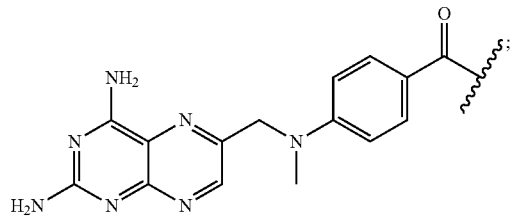 [SMILES: *C(=O)c1ccc(N(C)Cc2cnc3nc(N)nc(N)c3n2)cc1]

and region B of the compound is represented by a fragment having the structure:

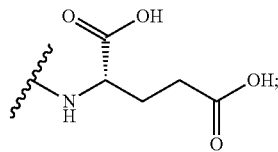 [SMILES: *N[C@@H](CCC(=O)O)C(=O)O]

wherein each stable isotope represents at least 50.1% incorporation of the isotope at each atom.

In one embodiment of the twenty-third embodiment, region A of the compound comprises more than five or more stable isotopes. For example, region A of the compound can contain five, six, seven, eight, nine, ten, eleven, twelve, thirteen, fourteen, fifteen, or more stable isotopes.

In another embodiment of the twenty-third embodiment, region B of the compound comprises more than five or more stable isotopes. For example, region B of the compound can contain five, six, seven, eight, nine, ten, eleven, twelve, thirteen, fourteen, fifteen, or more stable isotopes.

In one embodiment of the twenty-third embodiment, region A of the compound comprises 5 or more stable isotopes and region B of the compound comprises zero stable isotopes, one stable isotope, two stable isotopes, three stable isotopes, four stable isotopes, or five stable isotopes.

In another embodiment of the twenty-third embodiment, region B of the compound comprises 5 or more stable isotopes and region A of the compound comprises zero stable isotopes, one stable isotope, two stable isotopes, three stable isotopes, four stable isotopes, or five stable isotopes.

In yet another embodiment of the twenty-third embodiment, the stable isotopes can be deuterium, carbon-13, nitrogen-15, oxygen-18, or a combination thereof.

In another embodiment of the twenty-third embodiment, region A of the compound has a mass difference of +5 to +16 relative to region A lacking incorporation of stable isotopes. In an exemplary embodiment, region A of the compound has a mass difference of +5 to +11 relative to region A lacking incorporation of stable isotopes.

In yet another embodiment of the twenty-third embodiment, region A of the compound has a mass difference of +5 relative to region A lacking incorporation of stable isotopes.

In still another embodiment of the twenty-third embodiment, region A of the compound has a mass difference of +6 relative to region A lacking incorporation of stable isotopes.

In another embodiment of the twenty-third embodiment, region A of the compound has a mass difference of +7 relative to region A lacking incorporation of stable isotopes.

In still another embodiment of the twenty-third embodiment, region A of the compound has a mass difference of +8 relative to region A lacking incorporation of stable isotopes.

In yet another embodiment of the twenty-third embodiment, region A of the compound has a mass difference of +9 relative to region A lacking incorporation of stable isotopes.

In still embodiment of the twenty-third embodiment, region A of the compound has a mass difference of +10 relative to region A lacking incorporation of stable isotopes.

In another embodiment of the twenty-third embodiment, region A of the compound has a mass difference of +11 relative to region A lacking incorporation of stable isotopes.

In still another embodiment of the twenty-third embodiment, region A of the compound has a mass difference of +12 relative to region A lacking incorporation of stable isotopes.

In yet another embodiment of the twenty-third embodiment, region A of the compound has a mass difference of +13 relative to region A lacking incorporation of stable isotopes.

In another embodiment of the twenty-third embodiment, region A of the compound has a mass difference of +14 relative to region A lacking incorporation of stable isotopes.

In still another embodiment of the twenty-third embodiment, region A of the compound has a mass difference of +15 relative to region A lacking incorporation of stable isotopes.

In yet another embodiment of the twenty-third embodiment, region A of the compound has a mass difference of +16 relative to region A lacking incorporation of stable isotopes.

In still another embodiment of the twenty-third embodiment, region A of the compound has a mass difference of +5 or more relative to region A lacking incorporation of stable isotopes, and region B of the compound has a mass difference of +0 to +5 relative to region B lacking incorporation of stable isotopes.

In another embodiment of the twenty-third embodiment, region B of the compound has a mass difference of +0 relative to region B lacking incorporation of stable isotopes.

In yet another embodiment of the twenty-third embodiment, region B of the compound has a mass difference of +5 relative to region B lacking incorporation of stable isotopes.

In still another embodiment of the twenty-third embodiment, each hydrogen can be independently replaced with deuterium, each carbon can be independently replaced with carbon-13, each nitrogen can be can be independently replaced with nitrogen-15, or each oxygen can be independently replaced with oxygen-18.

In another embodiment of the twenty-third embodiment, the compound contains at least 5 deuterium atoms, at least 5 carbon-13 atoms, at least 5 nitrogen-15 atoms, or at least five oxygen-18 atoms. In an exemplary embodiment, the compound contains at least 5 carbon-13 atoms. In another exemplary embodiment, the compound contains at least 5 deuterium atoms. In yet another exemplary embodiment, the compound contains at least 5 nitrogen-15 atoms. In still another exemplary embodiment, the compound contains at least five oxygen-18 atoms.

In yet another embodiment of the twenty-third embodiment, region A of the compound contains at least 5 carbon-13 atoms on the phenyl ring. In some embodiments, region A can further comprise additional stable isotopes (e.g., 1, 2, 3, or more additional stable isotopes). Preferably, the additional stable isotope labels are located on region AA of the compound, wherein region AA of the compound has the structure:

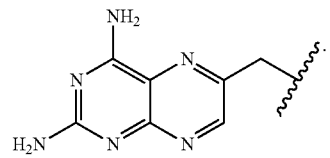

In an exemplary embodiment, the additional isotope labels are carbon replaced with carbon-13. In particular embodiments, region AA of the compound has a mass difference of +0 to +5 relative to region AA lacking incorporation of stable isotopes. For example, region AA can have a mass difference of +1, +2, +3, +4, or +5 relative to region AA lacking incorporation of stable isotopes.

In another embodiment of the twenty-third embodiment, region B of the compound contains 5 carbon-13 atoms.

In a twenty-fourth embodiment, the compound of Formula (II) has the structure of formula (III):

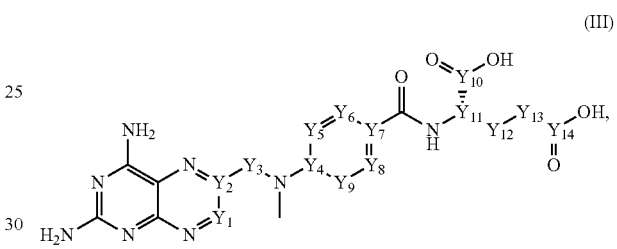

or a salt thereof; wherein each of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ is independently selected from carbon or carbon-13; and wherein at least 5 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

In one embodiment of the twenty-fourth embodiment, at least 5 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

In another embodiment of the twenty-fourth embodiment, at least 6 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

In yet another embodiment of the twenty-fourth embodiment, at least 7 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

In still another embodiment of the twenty-fourth embodiment, at least 8 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

In another embodiment of the twenty-fourth embodiment, at least 9 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

In yet another embodiment of the twenty-fourth embodiment, at least 10 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

In another embodiment of the twenty-fourth embodiment, at least 11 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

In still another embodiment of the twenty-fourth embodiment, at least 12 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

In another embodiment of the twenty-fourth embodiment, at least 13 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

In yet another embodiment of the twenty-fourth embodiment, all of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

In another embodiment of the twenty-fourth embodiment, 5 of $Y, Y_2, Y_3, Y_4, Y_5, Y_6, Y_7, Y_8, Y_9, Y_{10}, Y_{11}, Y_{12}, Y_{13}$, and $Y_{14}$ are carbon-13.

In still another embodiment of the twenty-fourth embodiment, 6 of $Y_1, Y_2, Y_3, Y_4, Y_5, Y_6, Y_7, Y_8, Y_9, Y_{10}, Y_{11}, Y_{12}, Y_{13}$, and $Y_{14}$ are carbon-13.

In another embodiment of the twenty-fourth embodiment, 11 of $Y_1, Y_2, Y_3, Y_4, Y_5, Y_6, Y_7, Y_8, Y_9, Y_{10}, Y_{11}, Y_{12}, Y_{13}$, and $Y_{14}$ are carbon-13.

In yet another embodiment of the twenty-fourth embodiment, 14 of $Y_1, Y_2, Y_3, Y_4, Y_5, Y_6, Y_7, Y_8, Y_9, Y_{10}, Y_{11}, Y_{12}$, $Y_{13}$, and $Y_{14}$ are carbon-13.

In still another embodiment of the twenty-fourth embodiment, at least 5 of $Y_4, Y_5, Y_6, Y_7, Y_8$, and $Y_9$, are carbon-13.

In another embodiment of the twenty-fourth embodiment, $Y_{10}, Y_{11}, Y_{12}, Y_{13}$, and $Y_{14}$ are carbon-13.

In an exemplary embodiment at least $Y_1, Y_2$, and $Y_3$, are carbon-13.

In a twenty-fifth embodiment, the compound of formula (II) has the structure of Formula (IV):

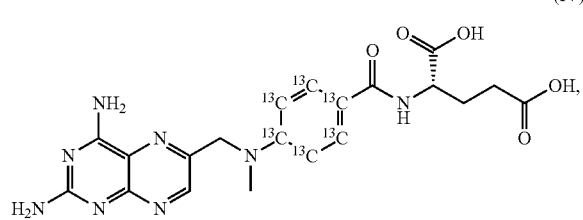

or a salt thereof.

In a twenty-sixth embodiment, the compound of formula (II) the compound has the structure of Formula (V):

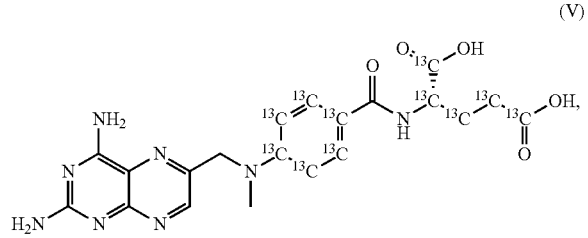 [SMILES: CN(Cc1cnc2nc(N)nc(N)c2n1)[13CH]1[13CH]=[13CH][13C](C(=O)N[13C@@H]([13CH2][13CH2][13C](=O)O)[13C](=O)O)=[13CH][13CH2]1]

or a salt thereof.

In a twenty-seventh embodiment, the compound of formula (II) the compound has the structure of Formula (VI):

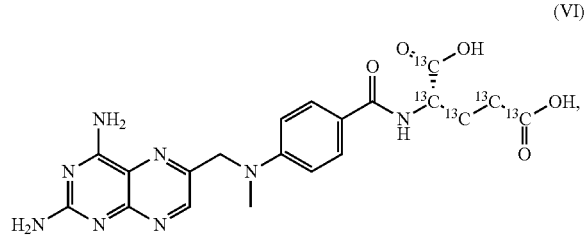 [SMILES: CN(Cc1cnc2nc(N)nc(N)c2n1)c1ccc(C(=O)N[13C@@H]([13CH2][13CH2][13C](=O)O)[13C](=O)O)cc1]

or a salt thereof.

In a twenty-eighth embodiment, the compound of formula (II) the compound has the structure of Formula (VII):

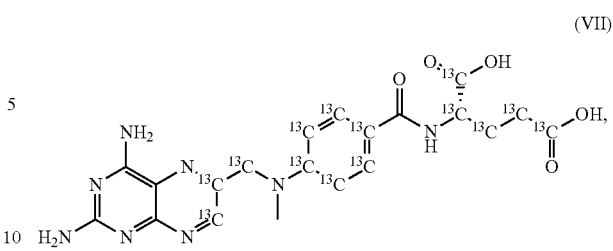

or a salt thereof.

In a twenty-ninth embodiment, the compound of Formula (II) has the structure of formula (III):

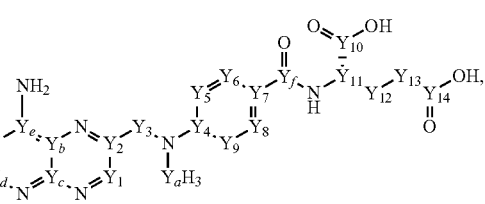

or a salt thereof; wherein each of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e$, and $Y_f$ is independently selected from carbon or carbon-13; and wherein at least 5 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e$, and $Y_f$ are carbon-13.

In another embodiment of the twenty-ninth embodiment, at least 6 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e$, and $Y_f$ are carbon-13.

In yet another embodiment of the twenty-ninth embodiment, at least 7 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e$, and $Y_f$ are carbon-13.

In still another embodiment of the twenty-ninth embodiment, at least 8 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e$, and $Y_f$ are carbon-13.

In another embodiment of the twenty-ninth embodiment, at least 9 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e$, and $Y_f$ are carbon-13.

In yet another embodiment of the twenty-ninth embodiment, at least 10 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e$, and $Y_f$ are carbon-13.

In another embodiment of the twenty-ninth embodiment, at least 11 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e$, and $Y_f$ are carbon-13.

In still another embodiment of the twenty-ninth embodiment, at least 12 of $Y_1, Y_2, Y_3, Y_4, Y_5, Y_6, Y_7, Y_8, Y_9, Y_1, Y_{11}, Y_{12}, Y_{13}, Y_{14}, Y_a, Y_b, Y_c, Y_d, Y_e$, and $Y_f$ are carbon-13.

In another embodiment of the twenty-ninth embodiment, at least 13 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e$, and $Y_f$ are carbon-13.

In yet another embodiment of the twenty-ninth embodiment, at least 14 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e$, and $Y_f$ are carbon-13.

In still another embodiment of the twenty-ninth embodiment, at least 15 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e$, and $Y_f$ are carbon-13.

In another embodiment of the twenty-ninth embodiment, at least 16 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e$, and $Y_f$ are carbon-13.

In yet another embodiment of the twenty-ninth embodiment, at least 17 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e$, and $Y_f$ are carbon-13.

In still another embodiment of the twenty-ninth embodiment, at least 18 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e,$ and $Y_f$ are carbon-13.

In another embodiment of the twenty-ninth embodiment, at least 19 of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y, Y_d, Y_e,$ and $Y_f$ are carbon-13.

In yet another embodiment of the twenty-ninth embodiment, all of $Y_1, Y_2, Y_3, Y_4, Y_5, Y_6, Y_7, Y_8, Y_9, Y_{10}, Y_{11}, Y_{12}, Y_{13}, Y_{14}, Y_a, Y_b, Y_c, Y_d, Y_e,$ and $Y_f$ are carbon-13.

In a thirtieth embodiment, the compound of formula (II) the compound has the structure of Formula (IX):

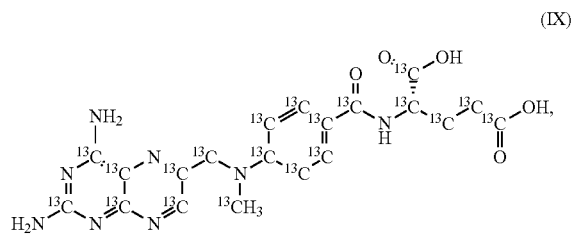 [SMILES: [13CH3]N([13CH2][13c]1[13cH]n[13c]2n[13c](N)n[13c](N)[13c]2n1)[13CH]1[13CH]=[13CH][13C]([13C](=O)N[13C@@H]([13CH2][13CH2][13C](=O)O)[13C](=O)O)=[13CH][13CH2]1]

or a salt thereof.

Samples

In general, a sample used in the methods described herein is a composition known or suspected to contain methotrexate. Samples can include a solid, liquid, gas, mixture, material (e.g., of intermediary consistency, such as a, extract, cell, tissue, organisms) or a combination thereof. In various embodiments, the sample is a bodily sample, an environmental sample, a food sample, a synthetic sample, an extract (e.g., obtained by separation techniques), or a combination thereof.

Bodily samples can include any sample that is derived from the body of a subject. In this context, the subject can be an animal, for example a mammal, for example a human. Other exemplary subjects include a mouse, rat, guinea-pig, rabbit, cat, dog, goat, sheep, pig, cow, or horse. In one embodiment, the subject is currently undergoing treatment with methotrexate. In another embodiment, the subject has previously undergone treatment with methotrexate. The individual can be a patient, for example, an individual suffering from a disease or being suspected of suffering from a disease. A bodily sample can be a bodily fluid or tissue, for example taken for the purpose of a scientific or medical test, such as for studying or diagnosing a disease (e.g., by detecting and/or identifying a pathogen or the presence of a biomarker). Bodily samples can also include cells, for example, pathogens or cells of the individual bodily sample (e.g., tumor cells). Such bodily samples can be obtained by known methods including tissue biopsy (e.g., punch biopsy) and by taking blood, bronchial aspirate, sputum, urine, feces, or other body fluids. Exemplary bodily samples include humor, whole blood, plasma, serum, umbilical cord blood (in particular, blood obtained by percutaneous umbilical cord blood sampling (PUBS)), cerebrospinal fluid (CSF), saliva, amniotic fluid, breast milk, secretion, ichor, urine, feces, meconium, skin, nail, hair, umbilicus, gastric contents, placenta, bone marrow, peripheral blood lymphocytes (PBL), and solid organ tissue extract.

In one embodiment, the sample is a blood sample. In another embodiment, the sample is a blood-derived sample, such as plasma or serum.

In another embodiment, the sample is a cell sample. The cell sample can contain material obtained or derived from a subject. In other embodiments, the cell sample can contain cells from an in vitro or ex vivo cell culture. In other embodiments, the sample is a cell supernatant sample.

While it is recognized that the majority of samples used in the methods described herein will be bodily samples, samples derived from other sources known or suspected to contain methotrexate may also be used in the disclosed methods. Such other samples include environmental samples, which may contain methotrexate due to, for example, the intentional or unintentional contamination of a given natural or manmade environment. Alternatively, other samples may include synthetic samples, which may include methotrexate as a result of, for example, an industrial process.

Environmental samples can include any sample that is derived from the environment, such as the natural environment (e.g., seas, soils, air, and flora) or the manmade environment (e.g., canals, tunnels, buildings). Such environmental samples can be used to discover, monitor, study, control, mitigate, and avoid environmental pollution. Exemplary environmental samples include water (e.g., drinking water, river water, surface water, ground water, potable water, sewage, effluent, wastewater, or leachate), soil, air, sediment, biota (e.g., soil biota), flora, fauna (e.g., fish), and earth mass (e.g., excavated material).

Synthetic samples can include any sample that is derived from an industrial process. The industrial process can be a biological industrial process (e.g., processes using biological material containing genetic information and capable of reproducing itself or being reproduced in a biological system, such as fermentation processes using transfected cells) or a non-biological industrial process (e.g., the chemical synthesis or degradation of a compound such as a pharmaceutical). Synthetic samples can be used to check and monitor the progress of the industrial process, to determine the yield of the desired product, and/or measure the amount of side products and/or starting materials.

In some embodiments, the sample is a biological sample selected from humor, whole blood, plasma, serum, umbilical cord blood, cerebrospinal fluid (CSF), saliva, amniotic fluid, breast milk, secretion, ichor, urine, feces, meconium, skin, nail, hair, umbilicus, gastric contents, placenta, bone marrow, peripheral blood lymphocytes (PBL), and solid organ tissue extract. In an exemplary embodiment, the sample is blood, plasma or serum.

Compositions and Kits

Compositions according to the invention can include a known quantity of one or more calibrators described herein; such as one or more of the compounds of the invention described above. For example, the invention provides compositions comprising a first known quantity of a first calibrator described herein. In one embodiment, the composition can further comprise a second known quantity of a second calibrator described herein. In another embodiment, the composition can further comprise a third known quantity of a third calibrator described herein. In still another embodiment, the composition can comprise a fourth known quantity of a fourth calibrator described herein. In another embodiment, known quantity of the one or more calibrators is different. In another embodiment, the calibrators and the methotrexate are each distinguishable in the single sample by mass spectrometry. Kits according to the invention can include any one or more of the foregoing compositions, together with instructions (and/or other/additional means) for implementing the methods described herein.

In some embodiments, compositions for quantifying methotrexate in a sample contain at least two of the calibrators described herein. However, in certain circumstances, it can be advantageous to include more than two internal calibrators (e.g., to increase precision and/or accuracy, to decrease signal noise and/or interference or to expand the measurement range). Accordingly, a composition comprising multiple internal calibrators can include 2, 3, 4, 5, 6, 7, 8, 9, 10, and up to an arbitrary number of internal calibrators for methotrexate (e.g., a theoretical maximum can be determined by the maximum number of calibrators that can be designed and used for methotrexate, for example, the number of positions that can be substituted for a stable isotope and will produce a usable signal in the contexts of methotrexate, other internal calibrators, and sample matrix. Each internal calibrator in the set should be distinguishable from each other and methotrexate by MS.

In one embodiment, the multiple calibrators are provided in a single sample, i.e., a sample containing a mixture of the multiple calibrators. In another embodiment, the multiple calibrators are provided as separate samples, which can optionally be combined by the user.

In order to quantify methotrexate, at least two of the internal calibrators are preferably present in a test sample in different amounts/concentrations. This facilitates preparation of a standard curve for quantifying an unknown amount of unlabeled methotrexate in the sample. In some embodiments, the amount of each internal calibrator is different. However, certain embodiments can include two or more of the internal calibrators in essentially the same amount/concentration (e.g., as long as at least two of the internal calibrators are present in different amounts/concentrations).

The amounts of the internal calibrators included in the compositions and/or kits can be selected to facilitate quantification of methotrexate. For example, the amounts of the internal calibrators can be selected to provide accuracy and precision over a specific analytical range of methotrexate. In another example, the amounts of the internal calibrators can be selected to provide maximum flexibility over the analytical range of the instrument.

In various embodiments, the multiple internal calibrators span a portion or essentially the entire analytical range of methotrexate in the sample to be analyzed. The analytical range can describe the range over which meaningful data can be collected (e.g., within predetermined statistical parameters). The analytical range can be defined by the detection limit of an internal calibrator or target analyte in a mass spectrometer and/or the expected amount(s) of target analyte in the sample.

Thus, the amount of one or more internal calibrators can approximate the expected amount of methotrexate in the sample (e.g., 50%, 75%, 95%, 96%, 97%, 98%, 99%, 100%, 101%, 102%, 103%, 104%, 105%, 125%, 150%, 200% ... of the expected amount of methotrexate in the sample). If the amount of methotrexate in the sample is expected to vary by orders of magnitude, then the amount of one or more internal calibrators can be, for example, 1%, 10%, 100%, 1000%, 10,000% of the expected amount of methotrexate in the sample.

The amount of one or more internal calibrators can be around/above the lower end of the analytical range of the internal calibrator in the instrument (e.g., 95%, 96%, 97%, 98%, 99%, 100%, 101%, 102%, 103%, 104%, 105%, 1000%, 10,000% of the lower end of the analytical range of the internal calibrator in the instrument). Similarly, the amount of one or more internal calibrators can be around/below the upper end of the analytical range of the internal calibrator in the instrument (e.g., 0.1%, ..., 1%, ... 95%, 96%, 97%, 98%, 99%, 100%, 101%, 102%, 103%, 104%, 105%, ... of the upper end of the analytical range of the internal calibrator in the instrument).

The relative amounts of the two or more calibrators (e.g., 4 calibrators) can be linear (e.g., 2×, 3×, 4×, ... ), exponential (e.g., $10^1$×, $10^2$×, $10^3$×, ... ), random, or a combination or variations thereof.

The relative amounts of any two internal calibrators (e.g., the internal calibrators present in the highest and lowest amounts) can be defined by a ratio, for example: 1.1, 1.15, 1.20, 1.25, 1.3, 1.4, 1.5, 2, 2.5, 3, 3.5, 4, 4.5, 5, 6, 7, 8, 9, 10, 11, 12, 13, 14, 15, 20, 25, 30, 35, 40, 45, 50, 55, 60, 65, 70, 75, 80, 90, 100, 150, 200, 250, 300, 350, 400, 450, 500, 600, 700, 800, 900, 1,000, 10,000, 100,000, 1,000,000, or more. For example, the ratio of the first calibrator and the second calibrator can be 1:4, or 4; the ratio of the first calibrator and the third calibrator can be 1:40, or 40, and/or the ratio of the first calibrator and the fourth calibrator can be 1:400, or 400. In an exemplary embodiment, the first calibrator, the second calibrator, the third calibrator, and the fourth calibrator are provided in a ratio of about 1:4:40:400. In another exemplary embodiment, there is a 5-fold difference in the amount of each calibrator (e.g., in embodiments where 4 internal calibrators are used, the calibrators are provided in a ratio of 1:5:25:125). In another exemplary embodiment, there is a 10-fold difference in the amount of each calibrator (e.g., in embodiments where 4 internal calibrators are used, the calibrators are provided in a ratio of 1:10:100:1000). In another exemplary embodiment, there is a 100-fold difference in the amount of each calibrator (e.g., in embodiments where 4 internal calibrators are used, the calibrators are provided in a ratio of 1:100:1000:10000).

The compositions of the present invention include dry preparations and liquid preparations (e.g., a solution, emulsion, suspension, etc.). The preparation can be determined by the requirement of compatibility with the internal calibrator (e.g., which could be incompatible with drying or unstable in liquid) or the sample (e.g., a liquid could be required to facilitate mixing and could need to be aqueous or organic or ion/pH balanced to be compatible with the sample).

Liquid preparations can include various inorganic or organic solvents, or mixtures thereof, which are compatible with the internal calibrators, sample, and MS analysis. In some embodiments, the solvent is selected for compatibility with a preparation, extraction, or separation (e.g., a chromatographic mobile phase and media). Exemplary solvents include water, acetonitrile, aliphatic alcohols (e.g., methanol, ethanol, propanol, isopropanol), hexafluoroacetone, and combinations thereof. The solvent can include additives, such as buffer salts (e.g., ammonium acetate), inorganic or organic acids (e.g., formic acid, trifluoroacetic acid, orthophosphoric acid, heptafluorobutyric acid), and/or inorganic or organic bases (e.g., $NH_3$).

Dry preparations can be prepared by various conventional drying techniques, such as, air drying, vacuum drying, spray-drying, drum drying, dielectric drying, freeze drying (e.g., lyophilization), supercritical drying, or a combination thereof. Dry preparations include preparations that are substantially free from a liquid, for example a solvent (e.g., water). In various embodiments, dry compositions can be quantified as having less than 10% w/w liquid (e.g., less than 9% w/w liquid, less than 8% w/w liquid, less than 7% w/w liquid, less than 6% w/w liquid, less than 5% w/w liquid, less than 4% w/w liquid, less than 3% w/w liquid, less than 2% w/w liquid, less than 1% w/w liquid, less than 0.5% w/w liquid, or less than 0.1% w/w liquid).

Compositions in accordance with the invention can include one or more additional substances, e.g., substances which improve the stability of the composition, improve or facilitate the processing of a sample, and/or allow, improve or facilitate the analysis of methotrexate. Such additional substances include antimicrobial agents (e.g., antibiotics, azides), antioxidants, reducing agents, pH adjusting agents (e.g., inorganic and/or organic acids, bases or buffers), chelating agents (e.g., EDTA), detergents, chaotropic agents, protease inhibitors (e.g., if degradation of peptides/proteins in the sample is to be avoided), DNase inhibitors (e.g., if degradation of DNA in the sample is to be avoided), RNase inhibitors (e.g., if degradation of RNA in the sample is to be avoided), beads (e.g., beads to disrupt cell membranes or beads having ion-exchange, magnetic, size-exclusion, and/or partition properties), proteases (e.g., if degradation of peptides/proteins in the sample is desired), DNase (e.g., if degradation of DNA in the sample is desired), RNase (e.g., if degradation of RNA in the sample is desired), and solvents (e.g., if the composition is in the form of a liquid preparation).

In some embodiments, the compositions and/or kits include quality control (QC) material, e.g., a dry or liquid preparation containing a known amount of methotrexate, either alone or in combination with one or more internal calibrators (e.g., unlabeled methotrexate), which is specific for said target analyte. In various embodiments, the QC is measured in the matrix. A kit can include pure methotrexate as a QC for the user to supply their own blank matrix or, alternatively, a kit can include one or more blank matrices that are pre-spiked or can be selected by the desired use to add to the pure QC material provided in the kit.

For example, a kit can include QC materials for each set of internal calibrators/target analyte. Compositions can include, for example, the internal calibrators and QC material in a single mixture. Kits can include, for example, one or more mixtures of internal calibrators as well as one or more corresponding QC materials.

Compositions in accordance with the invention can be contained in a sample holder defining at least one sample receptacle. The sample holder can be sealable (e.g., a sealable vial, a sealable tube such as a ready-to-use tube, a sealable microtitre plate such as a 6, 24, or 96 well plate, and the like). Numerous sample receptacles, such as vials, tubes, and plates, are known in the art.

In various embodiments, compositions according to the invention can be contained in a sample holder having one or more compartments. In one example, one or more compartments of the sample holder contain internal calibrators (i.e., two or more internal calibrators as described above) in amounts that are sufficient for the analysis of one sample (e.g., including one or more target analytes) per compartment.

In some embodiments, the sample holder defines an array of sample receptacles, each receptacle containing or receiving identical compositions (i.e., sets of two or more internal calibrators for each target analyte), thereby facilitating analysis of a plurality of samples against a common analytical panel. Alternatively, a sample holder can define an array of sample receptacles, each containing or receiving different compositions (i.e., distinct sets of two or more internal calibrators for each target analyte), thereby facilitating analyzing a single sample against a plurality of analytical panels.

In another embodiment, the composition is contained in one compartment (such as a sealable tube or vial) that contains the internal calibrators (e.g., two or more internal calibrators) in amounts and proportions that are sufficient for the analysis of multiple samples. The internal calibrators can be in a dry preparation, which can be reconstituted into a liquid preparation by addition of a solvent. The reconstituted liquid preparation can be added in equal aliquots to each of a plurality of samples to be analyzed, thereby ensuring that each sample includes the same quality and quantity of internal calibrators.

Compositions according to the invention can be contained in ready-to-use reaction tubes, for example, pre-aliquoted reaction tubes that can be directly used for sample processing or analysis. Pre-aliquoted reaction tube can contain internal calibrators in amounts and proportions sufficient for the analysis of one or more samples. For example, the reaction tube may contain a set of four internal calibrators, and the amounts of each internal calibrator within the set differ from each other. The tube can be securely closed (e.g., by a screw cap, snap-on cap, or puncture cap). Example tubes can have a volume in the range of less than 1 mL, 1 to 15 mL, or 1 to 2 mL (e.g., 1.5 mL). In general, the volume of a sample receptacle can be selected on the basis of the nature and amount of sample to be processed/analyzed.

Calibrators can be provided in compositions including (i) individual calibrators, (ii) sets of two or more calibrators for a target analyte, (iii) panels including sets for calibrators for two or more target analytes, and (iv) combination and variations thereof. A user or programmed apparatus can use such compositions (e.g., ii or iii) directly in an assay. Alternatively, a user or programmed apparatus can use such compositions (e.g., i-iv) to prepare a predetermined or customized composition for assaying a particular sample, analyte, or panel of analytes. Customized compositions can be advantageous in random access operation and/or in conducting multi-analyte panels from a single run with a single sample. Therefore, the inventive compositions provide flexibility and adaptability to essentially any assay and assay format.

Kits according to the invention can include any one or more of the compositions described herein, together with instructions (and/or other/additional means) for implementing methods and/or employing apparatuses for quantifying methotrexate in a sample. Such methods and apparatuses are discussed, in turn, below.

Methods

The invention features methods for quantifying methotrexate by mass spectrometry. In one embodiment, methods of quantifying methotrexate in a sample include providing a sample comprising a known quantity of a first calibrator corresponding to a first compound selected from any of the compounds of the invention, wherein the sample potentially comprises unlabeled methotrexate, and wherein the first calibrator, the second calibrator, and the unlabeled methotrexate are each distinguishable in the sample by mass spectrometry. A mass spectrometer signal comprising a first calibrator signal, a second calibrator signal, and potentially comprising an unlabeled methotrexate signal, can be obtained from the sample. The amount of unlabeled methotrexate in the sample can be determined by comparison of the unlabeled methoxtrexate signal to the first calibrator signal and the second calibrator signal.

In some embodiments, the method can further comprise providing a known quantity of a third calibrator corresponding to a third compound selected from any of the compounds of the invention. In this embodiment, the method further comprises obtaining a third calibrator signal from the sample, and quantifying the amount of unlabeled methotrexate in the sample using the first calibrator signal, the second calibrator signal, and the third calibrator signal.

In other embodiments, the method can further comprise providing a known quantity of a fourth calibrator corresponding to a fourth compound selected from any of the compounds of the invention. In this embodiment, the method further comprises obtaining a fourth calibrator signal from the sample, and quantifying the amount of unlabeled methotrexate in the sample using the first calibrator signal, the second calibrator signal, the third calibrator signal, and the fourth calibrator signal.

The methods described herein can also be adapted to use four or more calibrators (e.g., 5 calibrators, 6 calibrators, 7 calibrators, 8 calibrators, etc.).

As discussed above in the context of the properties and selection of calibrators for quantifying methotrexate, the methods can employ in some embodiments four or more calibrators for methotrexate. Additional calibrators can potentially be used to increase the precision and/or accuracy of methotrexate quantification. Additional calibrators can also be used where matrix effects are expected to obscure or distort a calibrator signal, thereby ensuring that an accurate calibration curve (or formula) can be determined despite any issues with the calibrator signals. Such additional calibrators are generally provided in different concentrations from the other calibrators for the given target analyte. However, in some embodiments, such additional calibrators can be provided in the same or essentially the same concentration as another calibrator, as long as at least two calibrators for the given target analyte are present in different amounts.

The relative amounts of any two internal calibrators (e.g., the internal calibrators present in the highest and lowest amounts) can be defined by a ratio, for example: 1 to 1.1, 1.15, 1.20, 1.25, 1.3, 1.4, 1.5, 2, 2.5, 3, 3.5, 4, 4.5, 5, 6, 7, 8, 9, 10, 11, 12, 13, 14, 15, 20, 25, 30, 35, 40, 45, 50, 55, 60, 65, 70, 75, 80, 90, 100, 150, 200, 250, 300, 350, 400, 450, 500, 600, 700, 800, 900, 1,000, 10,000, 100,000, 1,000,000, or more. For example, the ratio of the first calibrator and the second calibrator can be 1:4, or 4; the ratio of the first calibrator and the third calibrator can be 1:40, or 40, and/or the ratio of the first calibrator and the fourth calibrator can be 1:400, or 400. In an exemplary embodiment, the first calibrator, the second calibrator, the third calibrator, and the fourth calibrator are provided in a ratio of about 1:4:40:400.

Different methods for obtaining a mass spectrometer signal are known in thd art. In various implementations, mass spectrometric analysis includes ionizing one or more compounds to generate charged molecules or molecule fragments and measuring their mass-to-charge ratios (cf. Sparkman, O. D. (2000). Mass spectrometry desk reference. Pittsburgh: Global View Pub. ISBN 0-9660813-2-3). Such procedures can include the following steps: loading a mixture containing one or more compounds onto the MS instrument and vaporizing the one or more compounds; ionizing the components of the mixture, to form charged particles (ions); electromagnetic ally separating the ions according to their mass-to-charge ratio in an analyzer; detecting the ions (e.g., by a quantitative method); and transforming the ion signals into mass spectra.

The mass spectrometer can be operated, for example, in any of the following modes: (1) full scan, e.g., the mass spectrometer detects all ions between two distant points on the m/z scale (such as 0 and 10000); (2) Single Ion Monitoring (SIM) or Single Ion Recording (SIR), e.g., the mass spectrometer detects only ions which have a particular m/z value or which lie in a small mass m/z range (e.g., a range of 1 or 2 mass units); (3) Multiple Reaction Monitoring (MRM), e.g., in a mass spectrometer having multiple mass spectrometer units, at least two units are operated in the SIM/SIR mode.

After separation and measurement of the intensities of the ions in the mass spectrometer, mass spectra are created, for example by plotting the intensities measured for the detected ions vs. their mass-to-charge ratio (m/z). Depending on the mode by which the mass spectrometer is operated (full scan, SIM/SIR, or MRM), the mass spectra can include (1) the peaks corresponding to all ions (precursor and product ions) detected in the mass spectrometer between two distant points on the m/z scale; (2) the peaks corresponding to (a) all ions which have a particular m/z value or which lie within a very small m/z range and optionally (b) all product ions derived from the ions specified under (a); or (3) only one or more selected product/daughter ions (MRM channels).

For example, when the mass spectrometer is operated in MRM mode, one can create a single mass spectrum for a set of internal calibrators and methotrexate. The single mass spectrum will contain one peak for each internal calibrator and, if present in the sample, one peak for methotrexate. Alternatively, multiple mass spectra can be created for the first set of internal calibrators and methotrexate, where each of the multiple mass spectra only represents one of the internal calibrators or methotrexate. Such single mass spectrum or multiple mass spectra can be created for each set of internal calibrators and methotrexate.

Mass spectra created using MRM channels and where peak intensities are plotted against time (such as retention time if the mass spectrometer is coupled to a SPE, chromatography, or electrophoresis device) are often described as mass chromatograms. Thus, the term mass spectra, as used herein, can also relate to mass chromatograms (e.g., where the MS operates in MRM mode).

Next, the MS signal intensities (or relative signal intensities) of the ions representative of each of the internal calibrators and methotrexate are determined. The signal intensities of the ions in the mass spectra (e.g., the intensities of the peaks corresponding to these ions) can be determined on the basis of the peak height or peak area, for example on the basis of peak area such as by integrating the signal intensity of a specific ion with respect to time. The intensities of the ions signals in the mass spectrum/spectra can be normalized e.g., to 100%, to the most intense ion signal detected.

As discussed above in the context of the properties and selection of calibrators, analytes, compositions, and kits, the calibrators and methotrexate can be distinguished from each other based on their behavior in a mass spectrometer (e.g., due to differences i-their mass and/or fragmentation pattern).

In one embodiment, any four or more compounds (e.g., the first, second, third, and fourth calibrators and methotrexate) are distinguished and separated from each other in a mass spectrometer due to differences in their mass (e.g., due to difference in the mass of the precursor ions/parent ions derived from the two compounds). The masses of the two compounds (e.g., the first internal calibrator and methotrexate) can differ by a number of mass units that are resolvable by the instrumentation being used or that meet a predetermined cutoff. For example, the difference in mass of at least 1 (or 2, 3, 4, 5, . . . ) mass units between these two parent/precursor ions can originate from the presence of different isotopes (e.g., low abundant isotopes in one of the two parent/precursor ions vs. high abundant isotopes in the other of the two parent/precursor ions).

Next, methotrexate in the single sample is quantified using the first calibrator signal, the second calibrator signal, the third calibrator signal, the fourth calibrator signal, and methotrexate signal. The methods include quantifying methotrexate using methotrexate signal and a calibration curve or algebraic equation (i.e., based upon the calibrator signals). For example, the method can include (i) obtaining a calibration curve from the first calibrator signal and the second calibrator signal; and (ii) quantifying methotrexate using the calibration curve and methotrexate signal. Alternatively, the method can include quantifying methotrexate algebraically using the first calibrator signal, the second calibrator signal, the third calibrator signal, the fourth calibrator signal, and methotrexate signal. In one embodiment, the quantifying step can be carried out manually (e.g., using pencil and paper, a calculator, or a spreadsheet, for example in a one-off, research, or development setting) or automatically (e.g., using a programmed machine or purpose built machine, for example in a high-throughput or commercial setting).

Calibration curves can be obtained by applying a suitable regression algorithm (e.g., a Gauss least-square fitting method) to the data. Suitable regression algorithms can include the following steps: (1) selecting a mathematical function (model); (2) fitting the function from the experimental data; and (3) validating the model. The function can be, but is not necessarily, linear over the entire analytical range. Where the method is quantifying multiple target analytes, the step of creating a calibration curve using the corresponding calibrator signals can be performed for each set of internal calibrators, thereby creating a distinct calibration curve for methotrexate.

The amount of methotrexate, if present in the sample, can be quantified using the calibration curve. For example, quantification can be achieved by extrapolation using (1) a calibration curve based upon the calibrators corresponding to methotrexate and (2) methotrexate signal.

In various embodiments, the methods include one or more additional steps before mass spectrometry. Additional steps can be conducted manually or can be automated (e.g., in a specifically programmed or specifically built machine).

In one embodiment, the method includes (i) preparing a single sample by combining a known quantity of each calibrator in a single specimen potentially comprising methotrexate; and (ii) generating a mass spectrometer signal from the single sample using a mass spectrometer. Suitable sample preparation can vary depending upon the nature of the sample, calibrators, and analytical protocol. For example, sample preparation can include selecting suitable calibrators, selecting an analytical panel, and/or selecting the amounts of the various internal calibrators.

In another embodiment, the method also includes processing the sample prior to obtaining the mass spectrometer signal. For example, processing the sample can include separating the calibrators, and methotrexate from other components of the single sample. Processing can be performed by techniques commonly used for processing samples prior to MS analysis, or by a combination of such techniques, in order to (1) reduce the number of compounds introduced into the mass spectrometer; (2) concentrate the internal calibrators and target analyte(s), e.g., by depleting unwanted compounds and/or enrichment of the internal calibrator and target analyte; (3) separate the internal calibrators and target analyte(s) from other compounds that could interfere with the MS analysis; and/or (4) separate at least one set of internal calibrators and corresponding target analyte from other sets of internal calibrators and corresponding methotrexate. Such techniques can include one or more of solid phase extraction, liquid phase extraction, and chromatography (e.g., liquid, gas, affinity, immunoaffinity, and supercritical fluid chromatography).

FIG. 1 presents a flow chart outlining an example method for quantifying methotrexate in one or more samples, each independently including methotrexate in using internal calibration. In various implementations, the method of FIG. 1 can be carried out manually, semi-automatically, or automatically. Similarly, one or more steps can be added, omitted, and/or repeated. The method of FIG. 1 (and its variants) can also serve as the basis for instructions (e.g., to be included in a kit, in human and/or machine readable format), for a program (e.g., an algorithm or computer program, embodied in a computer readable medium), and/or for analytical system (e.g., specifically adapted or purpose-built machine).

Step 1.1 includes waiting for a sample to be submitted for analysis. Samples can include quality control samples or system suitability samples, as well as routine samples (e.g., samples potentially including methotrexate). Because the method does not require analyzing a separate series of calibrators (e.g., the calibrators and methotrexate are in a single sample), samples can be submitted in any order rather than as batches grouped according to the analysis that is required (e.g., the method is a random access method). In some embodiments, a bar-code label or other unique identifier is attached to the sample, to inform a user or automated system which internal calibrator set(s) to add to the sample and can thus also instruct the user or automated system to use appropriate LC and/or MS parameters.

Step 1.2 includes introducing internal calibrators into the sample. The internal calibrators can be added to the sample in different ways, for example, to suit automated or manual processes and to allow the determination of a single analyte or a panel of analytes in one assay. For example, Step 1.2.1 shows an embodiment where calibrators corresponding to the analyte(s) are added to the sample manually, Step 1.2.2 shows an embodiment where the sample is added to a container that is pre-loaded with calibrators (e.g., in a solution or dry format), and Step 1.2.3 shows an embodiment where an automated system is used to add one or more sets of internal calibrators (e.g., as directed, for example, by barcode recognition of sample).

Step 1.3 includes preparing the sample for analysis. Sample preparation can include any of the various techniques discussed herein, for example, protein precipitation, solid phase extraction, liquid-liquid extraction, immunoaffinity purification, affinity purification, and the like. Sample preparation can be carried out on-line or off-line.

Step 1.4 includes analyzing the sample by MS (e.g., using MS to measure the response, such as chromatographic peak area, of methotrexate and corresponding calibrators).

Step 1.5 includes checking the data. quality from Step 1.4. If the data is not acceptable, the sample can be resubmitted for analysis (e.g., return to Step 1.1). If the data is acceptable, the verified MS response data 1.6 can be used to quantify methotrexate.

Step 1.6 includes selecting an appropriate calculation method for quantifying methotrexate(s). One option is illustrated in step 1.6.1, which includes generating a sample-specific calibration line for each target analyte using the measured responses for the internal calibrators, together with their assigned concentration values. Another option is illustrated in step 1.6.2, which includes generating a sample-specific calibration line for methotrexate using the measured responses for the internal calibrators together with their known concentration values and measured relative response factor.

Step 1.7 includes calculating methotrexate concentration(s) in the single sample based upon the measured MS response and sample-specific calibration line. In an alternative embodiment, methotrexate concentration(s) can be calculated algebraically using methotrexate signal and the corresponding calibrator signals.

Step 1.8 includes reporting the result. In various embodiment, the result can be stored (step 1.8.1) in a computer (e.g., in a laboratory information management system or LIMS).

In various embodiments, the result can be reported (step 1.8.2) in a user readable format such as a printed report or screen display. Reporting methods are not mutually exclusive and the result can be reported and/or stored by two or more techniques.

Whereas Steps 1.1 thru 1.5 pertain most directly to a specifically programmed or specifically built machine for carrying out the method, the following steps 1.6 thru 1.8 pertain most directly to a software-based process that calculates and reports the results. Both processes can be completed by a single apparatus (e.g., where calculation is carried out on a computer that also controls the MS and sample handling hardware). However, because the steps are separable, the sample processing and analysis steps can continue in parallel to the calculation and reporting steps, thereby-increasing the speed and efficiency of the apparatus.

The methods of the invention can be embodied in tangible articles. For example, the methods can be included as instructions in a kit and/or can be in a computer readable medium including computer executable instructions (e.g., for operating an apparatus that implements the method). Instructions can include directions for executing, adapting, or modifying any one or more methods described herein and can be embodied in hard copy (e.g., handbooks, printouts, and the like) or in soft copy (e.g., electronic, in computer memory or storage, on a display, and the like). Likewise, computer readable media (e.g., disk storage, solid state memory, and the like) can include computer executable instructions for executing, adapting, or modifying any one or more methods described herein.

INCORPORATION BY REFERENCE

Reference is hereby made to U.S. Patent Publication No. 2014/0158881. All subject matter therein is incorporated herein by reference.

EXEMPLIFICATION

Unless indicated otherwise, all techniques, including the use of kits and reagents, were carried out according to the manufacturers' information, methods known in the art, or as described, for example, in *Tietz Text Book of Clinical Chemistry* 3 Edition (Burtis, C. A. & Ashwood, M. D., Eds.) W. B. Saunders Company, 1999; *Guidance for Industry. Bioanalytical Method Validation*. USA: Centre for Drug Evaluation and Research, US Department of Health and Social Services, Food and Drug Administration, 2001; and Sambrook et al., Molecular Cloning: A Laboratory Manual, $2^{nd}$ Edition (1989) Cold Spring Harbor Laboratory Press, Cold Spring Harbor, N.Y. The methods used below and described in these references are hereby incorporated by reference in their entirety.

Example 1: Consideration of the Minimum Number of Stable Isotope Labels Required in the Design of a Set of Internal Methotrexate Calibrators The synthesis of stable isotope labeled analogues is a time consuming and expensive process and cannot be undertaken on a trial and error basis. Expected analytical conditions were modelled theoretically so that appropriate materials could be synthesised. This example describes considerations for determining the theoretical minimum number of stable isotope labels required as a starting point to design a set of internal methotrexate calibrators that can be used to quantify the amount of methotrexate in a sample. Factors to consider include, for example, (1) the isotope distribution of methotrexate, (2) the dynamic range of the assay, and (3) the maximum allowable error in the result of the assay.

Methotrexate Isotope Distribution

Of those elements present in methotrexate ($C_{20}H_{22}N_8O_5$), carbon has the most abundant isotope in the form of carbon-13 ($^{13}C$) which accounts for approximately 1% of all naturally occurring carbon atoms. The presence of twenty carbon atoms in a methotrexate molecule provides the opportunity for the random occurrence of one or more $^{13}C$ atoms, each one causing an increase in the mass of the molecule by approximately 1 Dalton. As a result, methotrexate has a characteristic isotope distribution with relative intensities that can be predicted accurately.

Assay Dynamic Range

To accommodate the majority of samples submitted for analysis without performing dilution steps, an assay concentration range from approximately 0.01 μM to 10 μM unlabeled methotrexate is required. A sample at the upper end of the range may therefore contain up to 1000 times more unlabeled methotrexate (10.0 μM) than the amount of labeled methotrexate present in the lowest calibrator (0.01 μM).

Maximum Allowable Error

Typically, a maximum allowable error of approximately ±10% is preferred for therapeutic drug monitoring assays. Previous studies using a regular LC/MS calibration procedure for methotrexate demonstrated an error of <6% RSD (see, e.g. Waters Application Note, part number 720005508EN). To ensure that the total error does not exceed 10%, a maximum potential additional error of ≤4% was used in the design of the calibrators.

Figure 2:
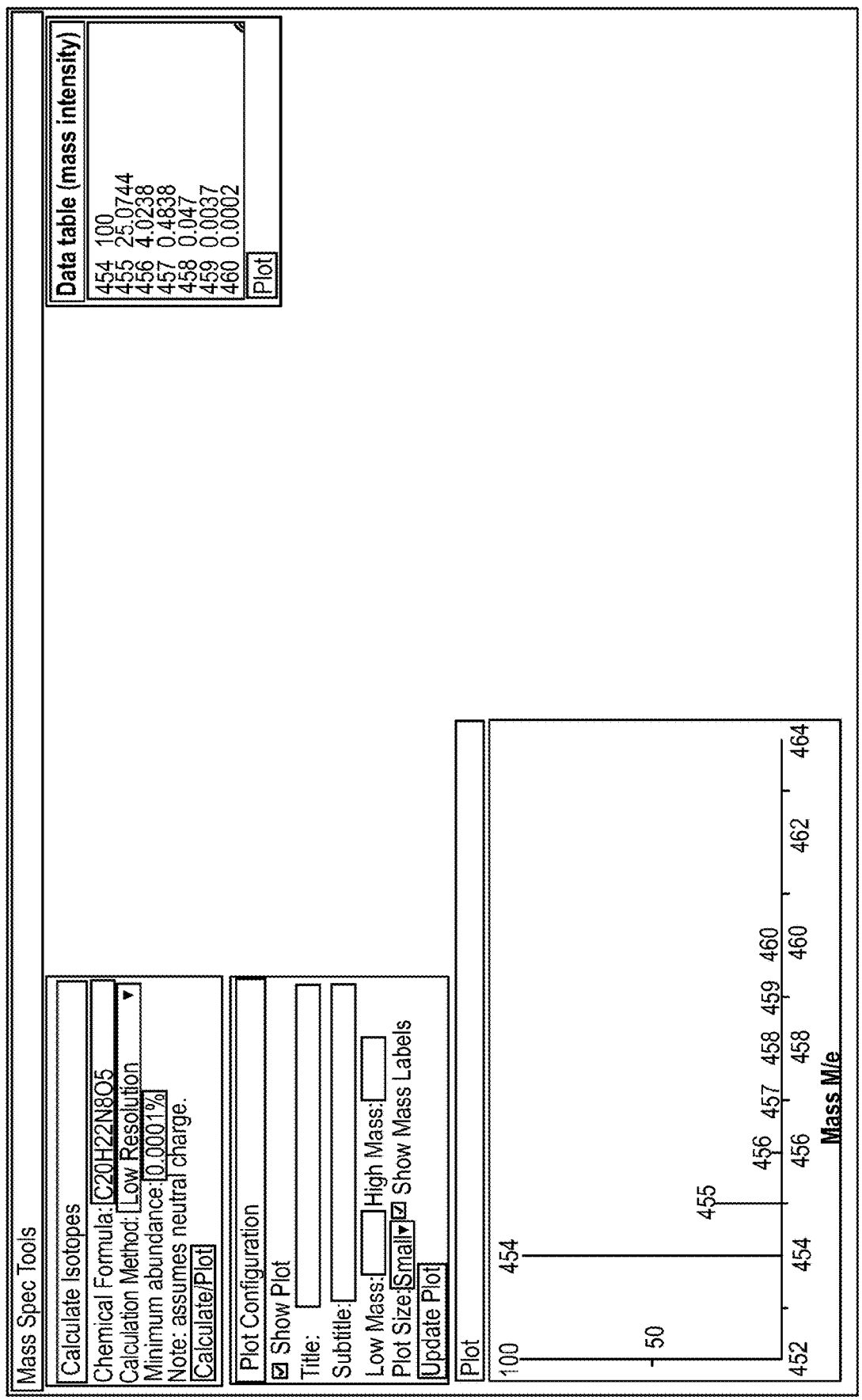
FIG. 2 illustrates an example of an output from the Scientific Instrument Services Isotope Distribution Calculator using the chemical formula for methotrexate as input.
Figure 4:
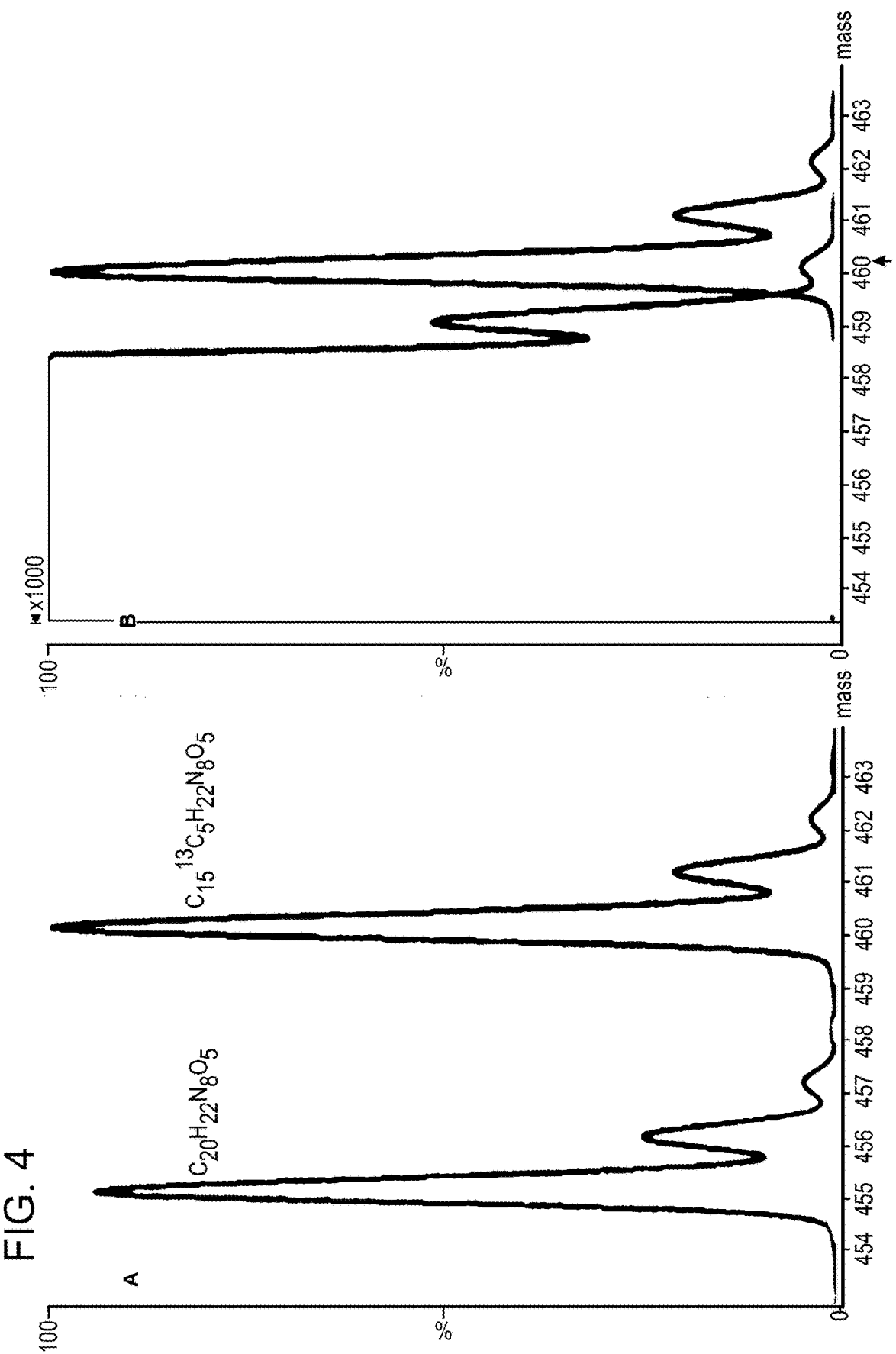
FIGS. 4A & 4B shows overlaid isotope distributions for methotrexate and $[^{13}C_5]$-methotrexate generated by MassLynx software.

By design, the internal methotrexate calibrators will contain a number of stable isotope labels so that they can be differentiated from unlabeled methotrexate and from each other using a mass spectrometer. The main isotope peak for each of the calibrators will therefore always be at higher mass compared to unlabeled methotrexate, and this creates the potential for naturally occurring isotopes of unlabeled methotrexate to interfere with the calibrators. In a worst case scenario, a sample may contain 10 μM unlabeled methotrexate (the upper end of the dynamic range of the assay) whereas the lowest calibrator will contain approximately 0.01 μM labeled methotrexate (the lower end of the dynamic range of the assay). To meet the error goal, the corresponding unlabeled methotrexate isotope peak must contribute ≤4% of the signal produced by the labeled calibrator. Due to the 1000 fold difference in concentration, that is equivalent to 0.004% of the intensity of the main isotope peak of the unlabeled methotrexate. This scenario was modelled mathematically using an on-line calculator (http://www.sisweb.com/mstools/isotope.htm) to determine the relative intensity of each of the isotope peaks of unlabeled methotrexate. The calculator indicates that the fifth isotope peak of unlabeled methotrexate has a relative intensity of 0.0037% (FIG. 2 and FIG. 3) and therefore meets the error goal. This was confirmed visually using the isotope tool in MassLynx software to generate and overlay mass spectra of unlabeled methotrexate and [$^{13}C_5$]-methotrexate (FIG. 4). Note that the calculator assumes that the molecules are neutral whereas MassLynx assumes that the molecules carry a positive charge so that the masses reported by MassLynx are one unit higher due to the additional proton. When analyzed using positive electrospray ionization mass spectrometry, the observed masses will correspond with the masses indicated by the MassLynx model. The MassLynx model confirms that a minimum of five stable isotope labels is required to reach the error goal and also highlights that methotrexate with four stable isotope labels (e.g. corresponding to [$^{13}C^2H_3$]-methotrexate; m/z 459) would not generally be suitable and could result in up to 50% interference under the conditions shown (FIG. 3 and FIG. 4B).

Conclusion

Based on the assumptions and assay parameters described above, a minimum of five stable isotope labels is desirable as a starting point for the design of a set of internal calibrators. From this starting point, similar principles can be used to design the additional internal calibrators for quantifying methotrexate.

Example 2: Preparation of Internal Methotrexate Calibrator Mixture for Quantifying Methotrexate An internal calibration assay for methotrexate was developed using four 13C-labeled methotrexate molecules. This was achieved by comparing the intensity of the MS signal produced by solutions of each of the 13C-labeled materials to the MS signal produced by a similar concentration of unlabeled Certified Reference methotrexate and determining relative response ratios. A large number of replicate analyses were used to ensure the accuracy of the relative response ratios so that the ratios could be used to determine the composition of the calibrator mix as shown below. This concentration value assignment process was performed because the exact purity of the 13C-labeled materials is not known, and because the 13C-labeled materials have isotope patterns that differ in intensity from unlabeled methotrexate and from each other.

Starting Materials (i) Cerilliant Certified Reference Material (CRM) methotrexate (MTx) at 1 mg/mL.
(ii) Four 13C-labeled methotrexate analogues, whose purity is unknown.

Preparation of Calibrator Stock Solutions

Using an accurate (5 figure or better) balance that has been calibrated with a 1 mg checkweight, >1 mg of each material was weighed and dissolved in the appropriate amount of solvent to yield 1 mg/mL solutions (e.g. If 1.13 mg of material is weighed, use 1.13 mL of MeOH:0.1N NaOH 90:10 v:v to dissolve). The mix was vortexed and sonicated to complete dissolution.

Theoretical Concentration of Stock Solutions

Initially, assume purity of 100% for calibrators 1 to 4.

| ID | Conc. (g/L*) | Molar Mass (g/mol) | Conc. (mol/L) | Conc. (µmol/L) |
|---|---|---|---|---|
| Unlabeled CRM MTx | 1.00 | 454.44 | 0.0022005 | 2200.5 |
| MTx Cal 1 ($^{13}C_{11}$) | 1.00 | 465.36 | 0.0021489 | 2148.9 |
| MTx Cal 2 ($^{13}C_5$) | 1.00 | 459.41 | 0.0021767 | 2176.7 |
| MTx Cal 3 ($^{13}C_6$) | 1.00 | 460.44 | 0.0021718 | 2171.8 |
| MTx Cal 4 ($^{13}C_{11}$) | 1.00 | 468.34 | 0.0021352 | 2135.2 |

*equivalent to mg/mL

Value Assignment

A mixed theoretical 0.5 µmol/L solution containing unlabeled methotrexate and the 4 $^{13}C$ labeled analogues was prepared using the following scheme:

| | |
|---|---|
| 0.0227 | mL of unlabeled MTx 1 mg/mL stock |
| 0.0232 | mL of MTx Cal 1 1 mg/mL stock |
| 0.023 | mL of MTx Cal 2 1 mg/mL stock |
| 0.023 | mL of MTx Cal 3 1 mg/mL stock |
| 0.0234 | mL of MTx Cal 4 1 mg/mL stock |
| 100 | mL final volume, made up with MeOH in a volumetric flask |
| 0.50 | µmol/L unlabeled MTx |
| 0.50 | µmol/L MTx Cal 1 |
| 0.50 | µmol/L MTx Cal 2 |
| 0.50 | µmol/L MTx Cal 3 |
| 0.50 | µmol/L MTx Cal 4 |

10 µL of the resulting stock was diluted in 990 µL 5% MeOH solution and analyzed 25 times, determining peak areas for all 5 components.

This experiment was repeated on a further 3 occasions, such that 100 injections were made in total.

Individual and mean ratios of labeled:unlabeled MTx peak areas were determined. Due to impurities, etc., the mean ratio will be <1.

These ratios were then used in the production of the spiking solution.

Preparation of Spiking Solution

In this example, mean ratios, of 0.9 are used in calculations.

Intended concentration of calibrators is as shown:

| ID | Conc. (µmol/L) | Ratio |
|---|---|---|
| Calibrator 1 | 0.025 | 1 |
| Calibrator 2 | 0.1 | 4 |
| Calibrator 3 | 1 | 40 |
| Calibrator 4 | 10 | 400 |

The preparation scheme involves adding 0.005 mL spiking solution to 0.095 mL sample.

Since the process of adding spiking solution dilutes unlabeled MTx (which is to be quantified), reduced quantities of calibrators were used:

| ID | Required conc. In matrix (µmol/L) | Solvent conc. required (µmol/L) | Conc. in matrix (µmol/L) | Conc. used for processing (µmol/L) |
|---|---|---|---|---|
| Calibrator 1 | 0.025 | 0.475 | 0.0238 | 0.0250 |
| Calibrator 2 | 0.1 | 1.90 | 0.0950 | 0.100 |
| Calibrator 3 | 1 | 19.0 | 0.950 | 1.00 |
| Calibrator 4 | 10 | 190 | 9.50 | 10.0 |

The following scheme may then be used to prepare an calibrator mix at the requisite concentrations:

| ID | Labeled:unlabeled Ratio Determined in Value Assignment | Molar Mass (g/mol) | Assigned Conc. of 1 mg/mL stock (μmol/L) | Conc. of solution taken (μmol/L) | Volume Taken (mL) | Final Volume (mL) | Conc. In solution (μmol/L) | Conc. in matrix (μmol/L) | Conc. used for processing (μmol/L) |
|---|---|---|---|---|---|---|---|---|---|
| 1 mg/mL Calibrator 1 | 0.9 | 465.36 | 1934.0 | 19.340 | 0.0247 | 1.00 | 0.478 | 0.0239 | 0.0251 |
| 1 mg/mL Calibrator 2 | 0.9 | 459.41 | 1959.0 | 195.90 | 0.0098 | | 1.92 | 0.0960 | 0.101 |
| 1 mg/mL Calibrator 3 | 0.9 | 460.44 | 1954.7 | 1954.7 | 0.0098 | | 19.2 | 0.958 | 1.01 |
| 1 mg/mL Calibrator 4 | 0.9 | 468.34 | 1921.7 | 1921.7 | 0.0989 | | 190 | 9.50 | 10.0 |

Note:
Calibrator 1 diluted 100-fold to and calibrator 2 10-fold to obtain solutions of desired concentrations. No dilution required for calibrators 3 and 4 (1 mg/mL stocks used neat).

Potential Number of Samples Analyzed and Consumption of Materials

It can be seen that calibrator 4 will be consumed at a faster rate than other materials.

Using this scheme: 10.1 mL of calibrator mix may be made from 1 mg of calibrator. Given that 0.005 mL of calibrator mix is used for one sample, this equates to 2022 samples/mg.

Example 3: Analysis of Methotrexate in Serum Using Internal Calibrators

This example describes a LC-MS/MS method for the analysis of methotrexate in plasma and serum. Analysis of methotrexate in serum was performed using the ACQUITY I-Class Xevo TQD (Tandem Quadrupole Detector) system with calibration.

A method had been developed using conventional UPLC (Ultra Performance Liquid Chromatography)-MS/MS methodology using the ACQUITY UPLC HSS SB C18, 2.1 mm×30 mm, 1.8 μm column. The column, in combination with the chromatography, gives good separation of methotrexate from its two principal metabolites.

Sample preparation icorporates a large dilution step, which is made possible by the sensitivity of the instrument.

Test Method
Equipment and Materials
  Equipment
  ACQUITY UPLC I-Class
  Xevo TQD
  ACQUITY UPLC HSS SB C18, 2.1 mm×30 mm, 1.8 μm (PN: 1860041.17)
  MassLynx®
  TargetLynx™
  Materials
  Unlabeled Methotrexate
  Methotrexate Calibrator 1, $^{13}C_{11}$
  Methotrexate Calibrator 2, $^{13}C_5$
  Methotrexate Calibrator 3, $^{13}C$
  Methotrexate Calibrator 4, $^{13}C_{14}$
  NEQAS EQA serum samples
  WEQAS EQA serum samples
  Serum samples received from Central Manchester University Hospitals
  Quality control samples from UTAK
  UPLC/MS grade methanol
  UPLC/MS grade water
  TraceSelect grade ammonium acetate
  Formic Acid Mobile Phase and Reagent Preparation
Mobile Phase A
  154 mg (±2 mg) of ammonium acetate was added to a 1 L bottle of LCMS Chromasolv water. 1 mL of formic acid was then added and the bottle was thoroughly mixed.
Mobile Phase B
  154 mg (±2 mg) of ammonium acetate was added to a 1 L bottle of LCMS Chromasolv methanol. 1 mL of formic acid was then added and the bottle was thoroughly mixed.
Wash Solvent
  800 mL of methanol and 200 mL of water were measured out and combined together. 1 mL of formic acid was then added and the bottle was thoroughly mixed.
Purge Solvent
  Mobile Phase A was used as purge solvent.
Seal Wash
  200 mL of methanol and 800 mL of water were measured out and combined together.
  The bottle was thoroughly mixed prior to being placed on the system.
Methanol in 0.01N sodium hydroxide
  90 mL of methanol and 10 mL of 0.1N sodium hydroxide were measured out and combined together. The bottle was thoroughly mixed prior to use.
Sample Preparation
  Standard Stocks
  The unlabeled analyte was supplied in a snap cap 1 mg/mL solution and was transferred to a glass vial for working solution preparation.
  Solutions at 1 mg/mL of calibrators 1 to 4 were prepared by dissolving the appropriate amount of material in methanol in 0.01N sodium hydroxide.
  Calibrator Mix
  A mixture containing calibrators in methanol in 0.01N sodium hydroxide at concentrations of 0.025 μmol/L (calibrator 1), 0.1 μmol/L (calibrator 2), 1 μmol/L (calibrator 3) and 10 μmol/L (calibrator 4) in serum was prepared (ratio=1:4:40:400).
  This involved preparing a solution containing approximately 0.5 μmol/L calibrator 1, 2 μmol/L calibrator 2, 20 μmol/L calibrator 3 and 200 μmol/L calibrator 4. When 5 μL of this mixture was spiked into 95 μL sample, the desired concentrations were obtained (50 μL of the sample was taken for analysis).
  Quality Controls (QCs)
  UTAK provided independent quality control materials
Sample Extraction
  1. Add 95 μL aliquot of sample to a micro-centrifuge tube.
  2. Add 5 μL of calibrator mix.

3. Place on a multi-tube vortex mixer for 30 seconds at 2500 r.p.m.
4. Transfer 50 μL to a clean micro-centrifuge tube.
5. Add 250 L methanol.
6. Place on a multi-tube vortex mixer for 30 seconds at 2500 r.p.m.
7. Centrifuge at 16100 g for 2 minutes.
8. Transfer 50 μL of the supernatant to a 96-well 2 mL plate, add 950 μL of UPLC/MS grade water and seal for analysis.

UPLC Method

| Column | ACQUITY UPLC HSS SB C18, 2.1 mm × 30 mm, 1.8 μm |
|---|---|
| Temperature | 45° C., precolumn heater active |
| Injection volume | 20 μL |
| Needle size | 30 μL |
| Syringe size | 100 μL |
| Run time | 5.0 minutes |
| Mobile Phase A | Water with 2 mM ammonium acetate and 0.1% formic acid |
| Mobile Phase B | Methanol with 2 mM ammonium acetate and 0.1% formic acid |
| Needle Wash | 80% methanol, 20% water and 0.1% formic acid |
| Purge Solvent | Mobile Phase A |
| Seal Wash | 80% water and 20% methanol |
| Flow Rate | 400 μL/min |

Gradient Timetable

| Time (mins) | Mobile Phase A (%) | Mobile Phase B (%) | Curve |
|---|---|---|---|
| Initial | 77 | 23 | Initial |
| 3.50 | 77 | 23 | 11 |
| 4.00 | 5 | 95 | 6 |
| 4.50 | 5 | 95 | 11 |
| 4.51 | 77 | 23 | 11 |

MS/MS Method

| Mode: | Positive |
|---|---|
| MS 1 Resolution | 0.75 FWHM |
| MS 2 Resolution | 0.75 FWHM |
| Capillary | 0.80 kV |
| Source Temperature | 150° C. |
| Desolvation Temperature | 500° C. |
| Desolvation Gas Flow | 800 L/Hr |
| Cone gas flow | 0 L/Hr |
| Extractor | 3.0 kV |
| RF | 2.5 V |
| MS Inter-scan delay | 0.02 |
| Polarity/Mode Switch Inter-scan delay | 0.02 |
| Inter-channel delay | 0.1 |

| Compound | Parent Mass | Daughter Mass | Dwell (s) |
|---|---|---|---|
| Methotrexate (unlabeled) | 455.2 | 308.1 | 0.05 |
| Methotrexate Calibrator 1 ($^{13}C_{11}$) | 466.2 | 314.1 | 0.05 |
| Methotrexate Calibrator 2 ($^{13}C_5$) | 460.2 | 308.1 | 0.02 |
| Methotrexate Calibrator 3 ($^{13}C_6$) | 461.2 | 314.1 | 0.01 |
| Methotrexate Calibrator 4 ($^{13}C_{14}$) | 469.2 | 317.1 | 0.01 |

Results

Value Assignment

The 1 mg/mL stocks of unlabeled methotrexate and calibrators 1 to 4 were diluted to make a mixed solvent (methanol in 0.01N sodium hydroxide) solution containing 0.5 μmol/L of each entity.

The solution was analyzed in 4 batches of 25 samples (n=100 in total), and the mean ratio between each calibrator and the unlabeled methotrexate established. Typically, these were approximately 0.9. These ratios were then used in the scheme to prepare the calibration mix.

Equipment and Materials

Calibration of the method was performed over the range of 0.025-10 μmol/L, with lines consistently linear with coefficient of determinations ($r^2$)>0.99) and individual calibrators deviating by no more than 15% from nominal concentrations (20% for calibrator 1). 1/x weighting was used, and lines were not forced through the origin.

Carryover

No significant system carryover was observed from high concentration samples at 100 μmol/L serum. Carryover was assessed by comparing concentration of unprotected blanks (analyzed immediately after the high concentration sample) to protected blanks (analyzed after a solvent blank).

Sensitivity

Analytical sensitivity, investigations reveal that the sensitivity of this method would allow precise quantification (≤20% RSD) at 0.015 μmol/L for methotrexate in serum (Table 1).

TABLE 1

Assessment of functional sensitivity across and below the calibration range at 6 concentrations (n = 30).

| Pool | Nominal Conc μmol/L | Mean Conc μmol/L | SD | % RSD | % Deviation |
|---|---|---|---|---|---|
| A | 0.0025 | 0.00219 | 0.00205 | 93.5 | −12.4 |
| B | 0.005 | 0.00440 | 0.00198 | 45.1 | −12.0 |
| C | 0.01 | 0.00853 | 0.00215 | 25.2 | −14.7 |
| D | 0.015 | 0.0130 | 0.00227 | 17.4 | −13.3 |
| E | 0.02 | 0.0183 | 0.00313 | 17.2 | −8.5 |
| F | 0.025 | 0.0223 | 0.00269 | 12.1 | −10.8 |

Figure 18:
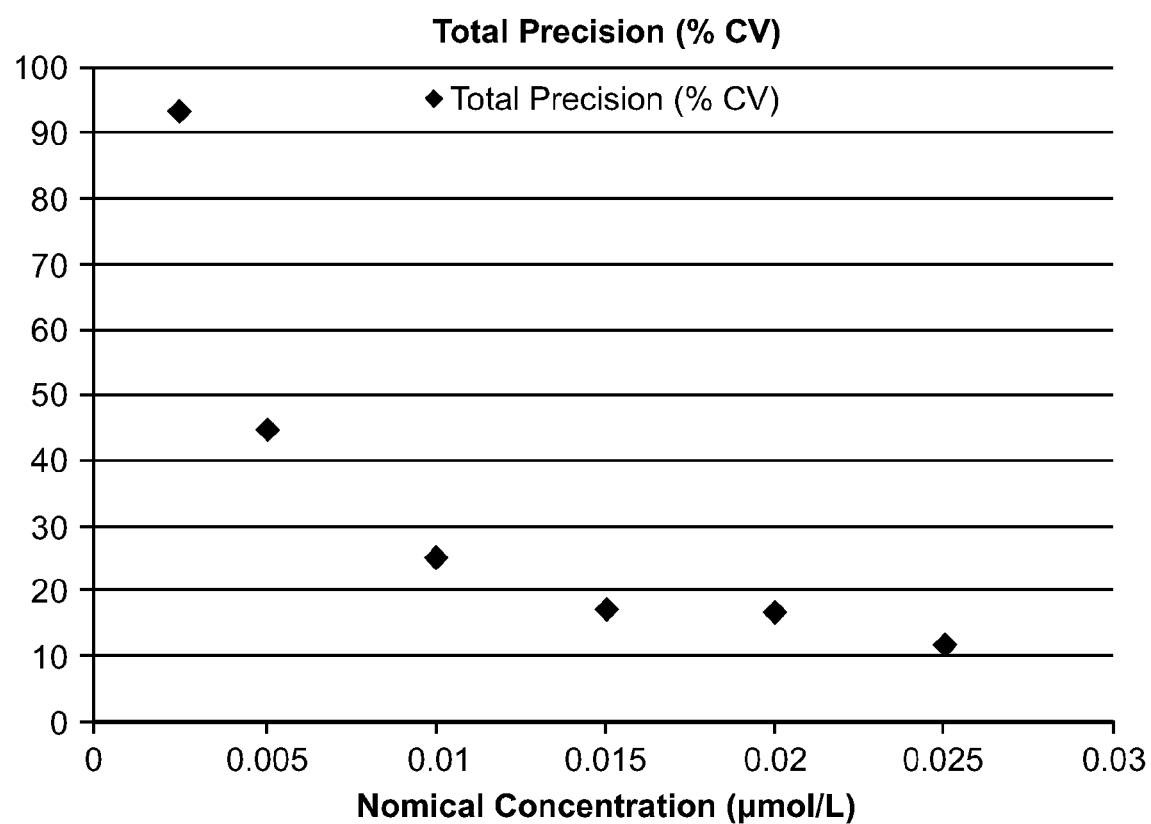
FIG. 18 is a graph demonstrating the functional sensitivity of the method performance.

10 replicates of methotrexate samples of decreasing concentration were analysed on 3 occasions. The results indicated that the method would allow precise quantification (≤20% RSD for total precision and repeatability) at 0.015 μmol/L (FIG. 18).

Precision

Total precision and repeatability was performed with five replicates of each QC levels extracted once per day for five days (n=25) (Table 2).

TABLE 2

Assessment of total precision and repeatability at 0.1, 1, 2.5 and 10 μmol/L methotrexate in serum.

| | Total QC Precision (% RSD) | | | | QC Repeatability (% RSD) | | | |
|---|---|---|---|---|---|---|---|---|
| | Concentration (μmol/L) | | | | | | | |
| | 0.1 | 1 | 2.5 | 10 | 0.1 | 1 | 2.5 | 10 |
| Methotrexate | 6.8 | 3.3 | 2.8 | 2.2 | 6.3 | 1.8 | 1.3 | 0.9 |

Linearity

The method was shown to be linear over the range of 0.175-13.0 μg/mL when different volumes of high and low concentration pools of methotrexate were combined and analysed.

Figure 17:
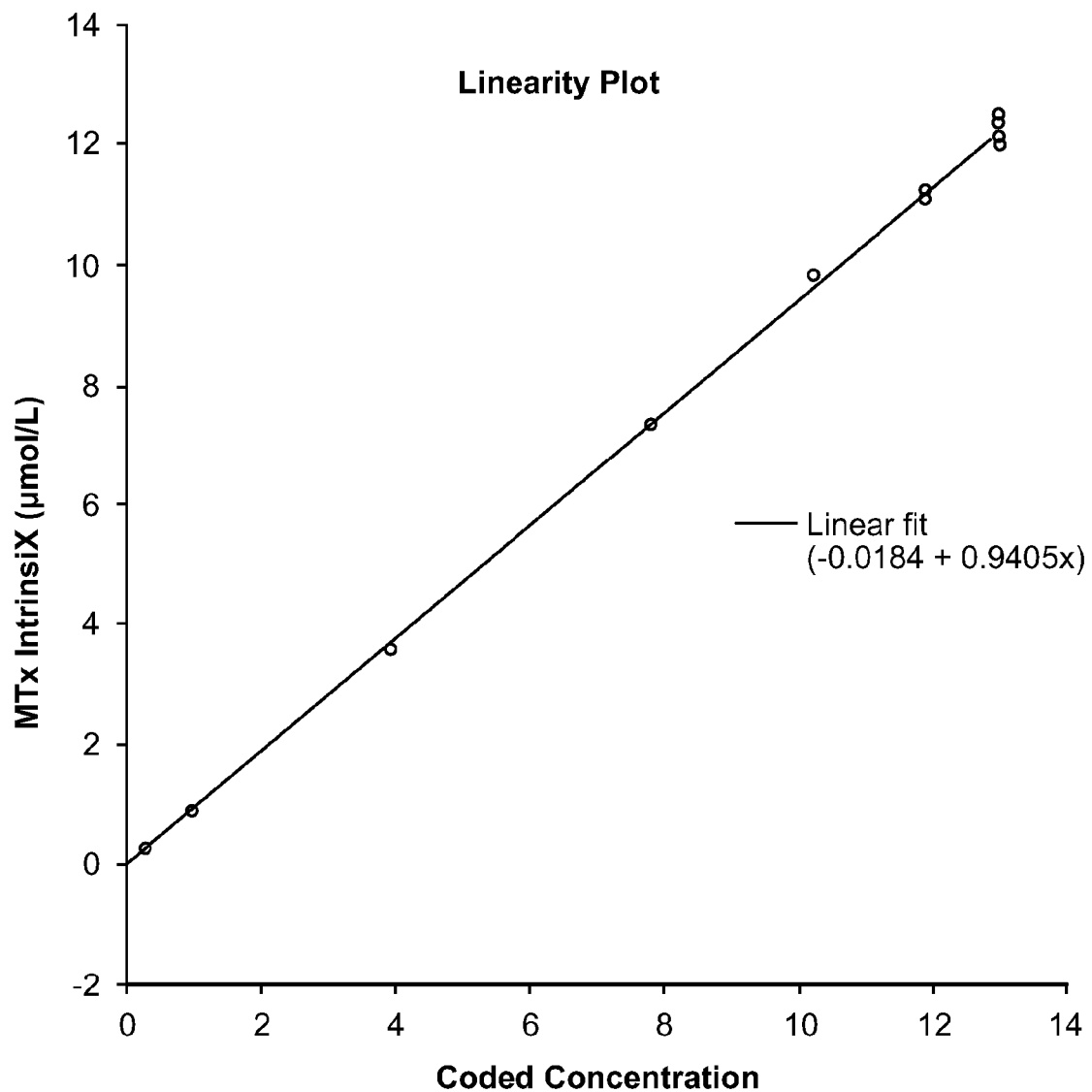
FIG. 17 is a graph demonstrating the linearity of the method performance.

When processed using 1/x weighting, not forcing through origin, all calibration lines were acceptable. MTx pools spanning 0.0175-13.0 μmol/L were prepared and analysed (30% above intended range) as per CLSI EP06-A and absence of non-linear terms established (FIG. 17).

Analytical Specificity

There was no significant interference in the quantification of methotrexate when the following individual endogenous and exogenous compounds were assessed in serum: albumin, bilirubin, cholesterol, intralipid, creatinine, triglycerides and uric acid (Tables 3 and 4).

TABLE 3

Analytical specificity (endogenous/exogenous compounds) for methotrexate at low concentration, 0.1 μmol/L.

| Substance | Concentration Supplemented | Mean Concentration Control Pool (μmol/L, n = 3) | Mean Concentration Test Pool (μmol/L, n = 3) | $d_{obs}$ | % Difference | % Recovery |
|---|---|---|---|---|---|---|
| Albumin | 120 mg/mL | 0.0893 | 0.0878 | 0.0014 | −1.6 | 98.4 |
| Bilirubin | 700 μg/mL | 0.0878 | 0.0853 | 0.0025 | −3.0 | 97.0 |
| Cholesterol | 4 mg/mL | 0.0882 | 0.0938 | −0.0056 | 6.0 | 106.0 |
| Intralipid | 5 mg/mL | 0.0927 | 0.0978 | −0.0051 | 5.2 | 105.2 |
| Triglycerides | 7.5 mg/mL | 0.0920 | 0.0954 | −0.0035 | 3.6 | 103.6 |
| Uric Acid | 300 μg/mL | 0.0877 | 0.0887 | −0.0010 | 1.1 | 101.1 |

TABLE 4

Analytical specificity (endogenous/exogenous compounds) for methotrexate at high concentration, 1.0 μmol/L.

| Substance | Concentration Supplemented | Mean Concentration Control Pool (μmol/L, n = 3) | Mean Concentration Test Pool (μmol/L, n = 3) | $d_{obs}$ | % Difference | % Recovery |
|---|---|---|---|---|---|---|
| Albumin | 120 mg/mL | 0.913 | 0.872 | 0.041 | −4.7 | 95.3 |
| Bilirubin | 700 μg/mL | 0.900 | 0.899 | 0.001 | 0.0 | 100.0 |
| Cholesterol | 4 mg/mL | 0.879 | 0.890 | −0.011 | 1.2 | 101.2 |
| Intralipid | 5 mg/mL | 0.949 | 0.906 | 0.043 | −4.7 | 95.3 |
| Triglycerides | 7.5 mg/mL | 0.922 | 0.946 | −0.024 | 2.5 | 102.5 |
| Uric Acid | 300 μg/mL | 0.879 | 0.916 | −0.037 | 4.0 | 104.0 |

Similarly, there was no significant interference in the quantification of methotrexate in the presence of the principle metabolites 7-hydroxymethotrexate and 2,4-diamino-$N^{10}$-methypteroic acid (DAMPA) at high concentration in serum (Tables 5 and 6).

TABLE 5

Analytical specificity (metabolites) for methotrexate at low concentration, 0.1 μmol/L.

| Substance | Concentration Supplemented | Mean Concentration Control Pool (μmol/L, n = 3) | Mean Concentration Test Pool (μmol/L, n = 3) | $d_{obs}$ | % Difference | % Recovery |
|---|---|---|---|---|---|---|
| 7-hydroxymethotrexate | 5 μmol/L | 0.0892 | 0.0912 | −0.0020 | 2.1 | 102.1 |
| | 50 μmol/L | 0.0860 | 0.0902 | −0.0042 | 4.7 | 104.7 |
| DAMPA | 5 μmol/L | 0.0880 | 0.0875 | 0.0005 | −0.5 | 99.5 |
| | 50 μmol/L | 0.0885 | 0.0922 | −0.0037 | 4.0 | 100.4 |

TABLE 6

Analytical specificity (metabolites) for methotrexate at low concentration, 0.1 μmol/L.

| Substance | Concentration Supplemented | Mean Concentration Control Pool (μmol/L, n = 3) | Mean Concentration Test Pool (μmol/L, n = 3) | $d_{obs}$ | % Difference | % Recovery |
|---|---|---|---|---|---|---|
| 7-hydroxymethotrexate | 5 μmol/L | 0.908 | 0.908 | 0.000 | 0.0 | 100.0 |
| | 50 μmol/L | 0.915 | 0.922 | −0.006 | 0.7 | 100.7 |
| DAMPA | 5 μmol/L | 0.925 | 0.917 | 0.008 | −0.9 | 99.1 |
| | 50 μmol/L | 0.919 | 0.903 | 0.016 | −1.8 | 98.2 |

Recovery of methotrexate from several (n=6) WEQAS samples fortified at 0.1, 2.5 and 7.5 μmol/L was assessed, with the 0.1 μmol/L mean being marginally greater than 110% and other concentrations within 90-110%.

Accuracy

Samples were obtained from the NEQAS and WEQAS schemes and analysed.

Figure 14:
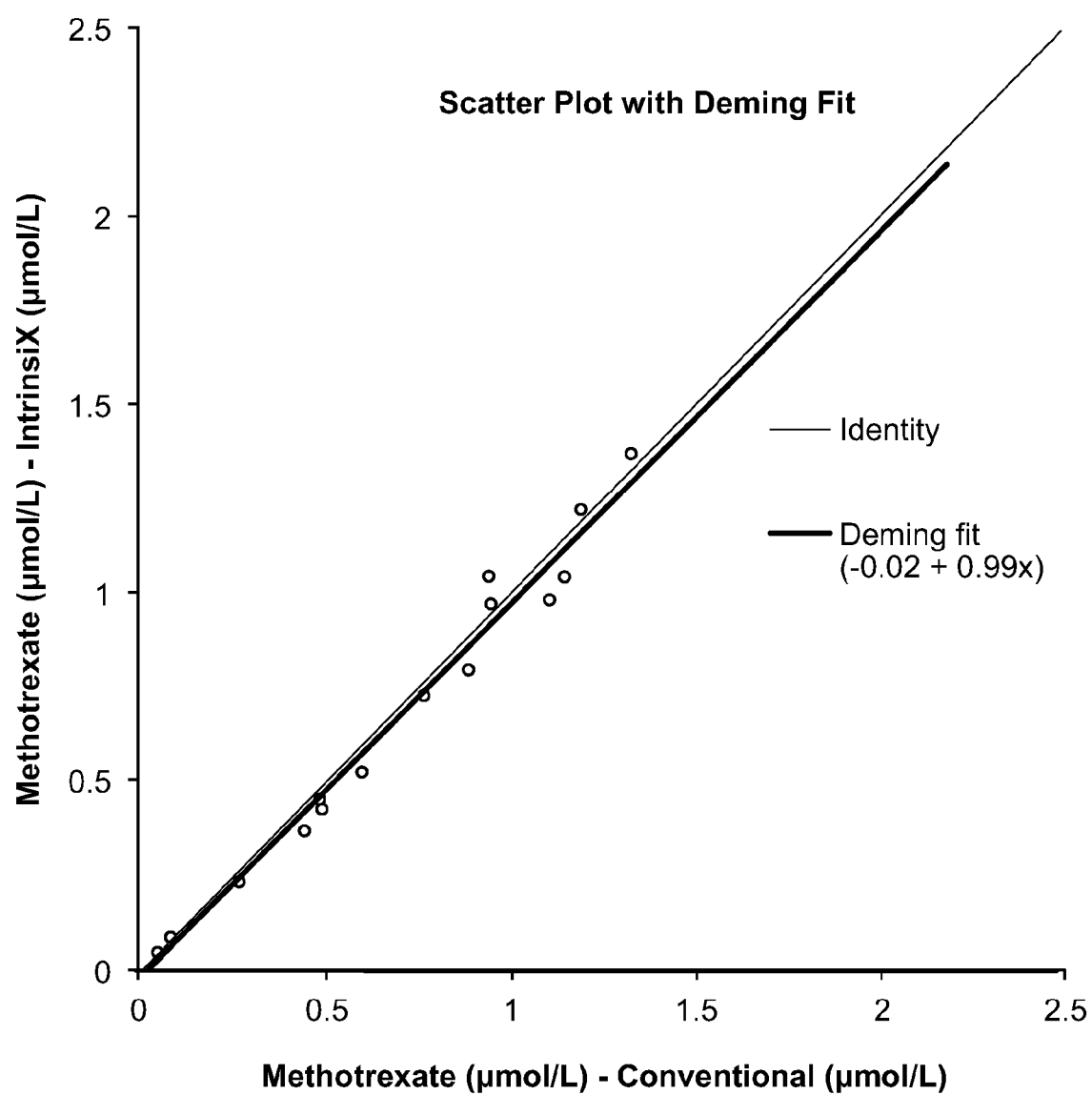
FIG. 14 shows the correlation between the internal methotrexate calibration methodology described herein and conventional UPLC-MS/MS analysis, described by Deming equation y=−0.99x−0.02 (n=23, range 0.025-2.18 μmol/L).

Correlation between internal calibration analysis and conventional UPLC-MS/MS analysis was described by Deming equation y=−0.99x-0.02 (n=23, range 0.025-2.18 μmol/L); significant constant bias though no proportional bias (p>0.05) (FIG. 14).

Figure 15:
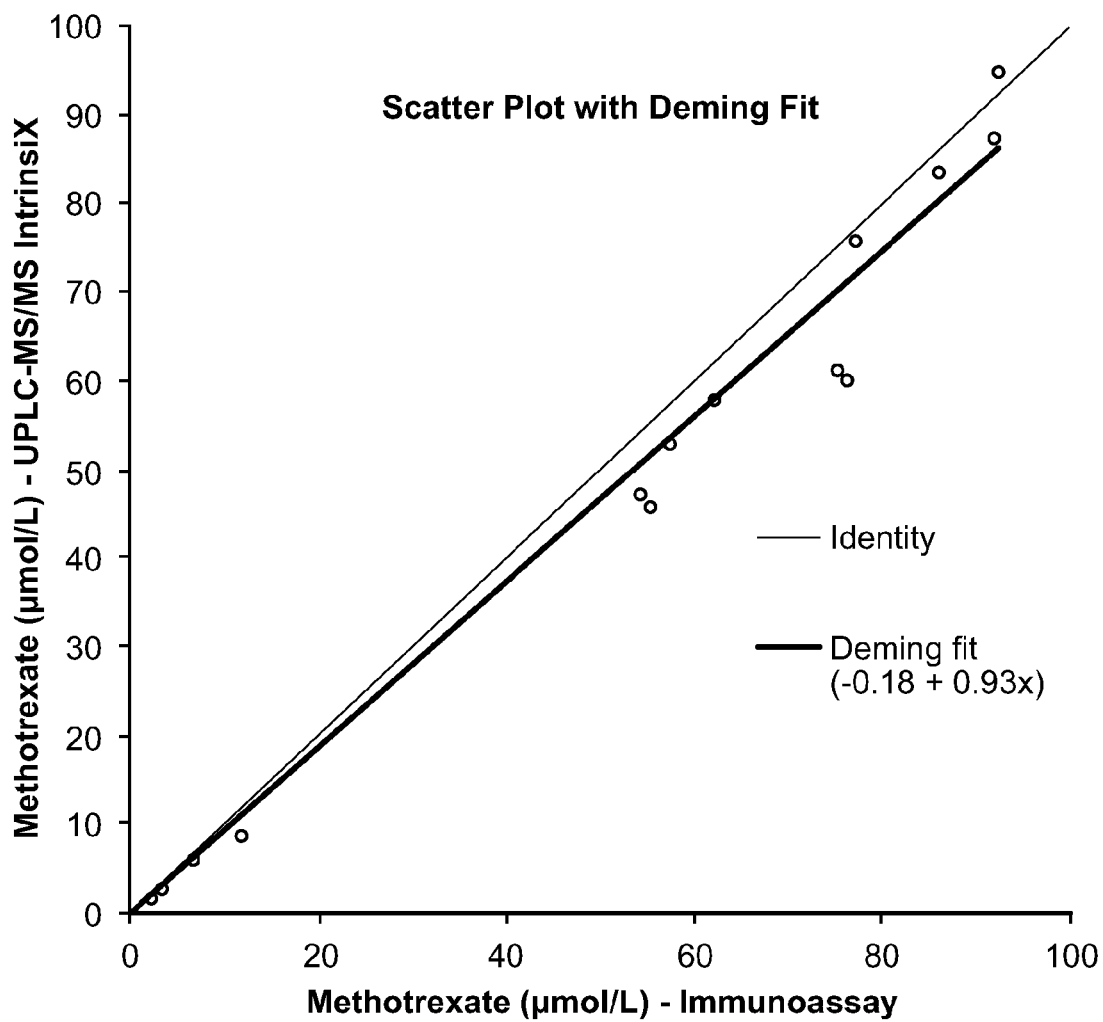
FIG. 15 shows the correlation between the internal methotrexate calibration methodology described herein and ALTM (all laboratory trimmed mean) described by Deming equation y=0.94x+0.03 (n=14, range 0.030-2.14 μmol/L)

Correlation between internal calibration and ALTM (all laboratory trimmed mean) was described by Deming equation y=0.94x+0.03 (n=14, range 0.030-2.14 μmol/L); significant constant bias though no proportional bias (p>0.05) (FIG. 15).

Serum Sample Analysis

Figure 16:
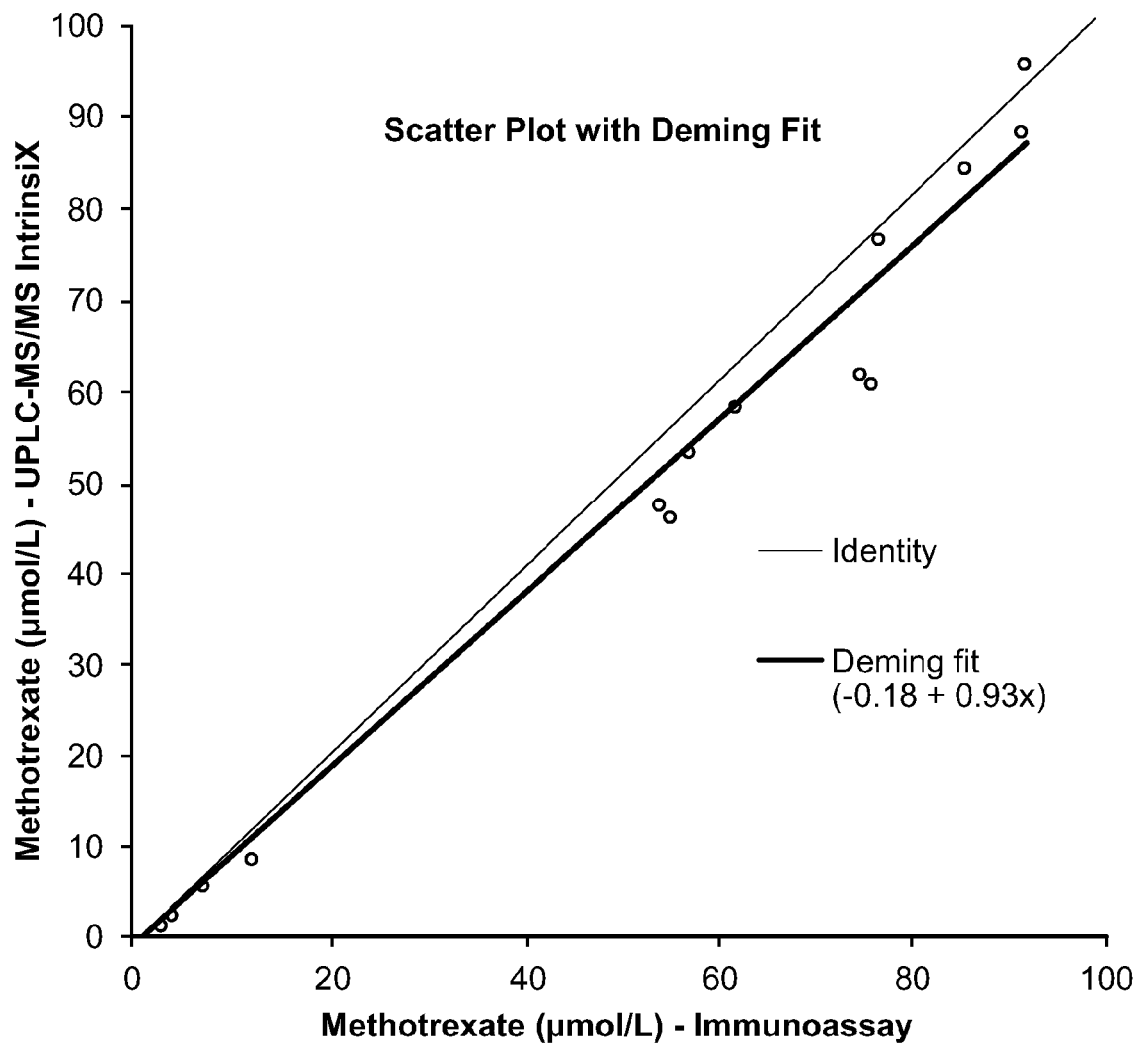
FIG. 16 shows a scatter plot with Deming fit of immunoassay method versus internal methotrexate calibration UPLC-MS/MS method.

Serum samples were obtained from Central Manchester University Hospitals NHS Foundation Trust. The agreement between the immunoassay method traditionally used to analyse samples and the internal calibration analysis method was described by the Deming equation y=0.93x−0.18 (n=67, range 0.05-92.5 μmol/L) (FIG. 16), demonstrating neither significant constant nor proportional bias (p>0.05). Some of these samples are likely to be post-glucarpidase administration, for which the immunoassay is known to overestimate methotrexate concentrations due to cross reactivity of the DAMPA metabolite. The internal calibration method described herein is suitable for use with samples obtained from subjects treated with glucarpidase.

Conclusion

A method for the analysis of methotrexate in serum using the internal calibration has been developed and assessed for feasibility, following CLSI and Bioanalytical guidelines.

Example 4: Dried Methotrexate Calibrators as Prototype Kit Components

The feasibility of analysing unlabeled methotrexate in samples using calibrators dried down in a receptacle was assessed. For comparison, an aliquot of solvent containing calibrators was added to parallel samples prior to processing and analysis ("spiking approach"). Replicate analyses of two quality control samples is used to compare the "dried-down" approach to the validated spiking approach.

Method

A previously prepared spiking solution containing 0.477 μmol/L calibrator 1, 1.92 μmol/L calibrator 2, 19.2 μmol/L calibrator 3 and 190 μmol/L calibrator 4 was diluted 20-fold by making 250 μL to a final volume of 5.0 mL in methanol.

20 microcentrifuge tubes were opened and 100 μL of the diluted calibrator mix was added to each. Tubes were left open in a fume hood overnight (approximately 16 hr) to allow evaporation of solvent. No nitrogen or temperature was used to assist evaporation.

The following day, visual inspection suggested no residual solvent remained. Into ten of the microtubes, 95 μL of a 0.5 μmol/L serum methotrexate sample was added. In the remaining ten microtubes, 95 μL of a 5.0 μmol/L serum methotrexate sample was added. For consistency with the spiking approach, 5 μL of solvent was also added to each tube. Following 30 minutes of equilibration at room temperature, tubes were capped then shaken at 2500 r.p.m. for 5 minutes on a multitube vortex mixer. 50 μL of the sample was taken for analysis.

Simultaneously, ten replicates of both 0.5 μmol/L and 5.0 μmol/L samples were analysed using the previous spiking approach, in which 5 μL of solvent containing calibrators was added to 95 μL of sample, then 50 μL taken for analysis.

All twenty samples were analysed by LC/MS/MS using the optimised conditions as described Example 3.

Results

| Sample ID | Spiked-in Conc (μmol/L) | Mean Spiked-in Conc. (μmol/L) | SD Spiked-in Conc (μmol/L) | % CV | Dried-down Conc. (μmol/L) | Mean Dried-down Conc. (μmol/L) | SD Spiked-in Conc (μmol/L) | % CV | % Difference from Spiked-in |
|---|---|---|---|---|---|---|---|---|---|
| 0.5 μmol/L Rep 1 | 0.529 | 0.507 | 0.015 | 2.9 | 0.500 | 0.509 | 0.018 | 3.5 | 0.4 |
| 0.5 μmol/L Rep 2 | 0.508 | | | | 0.500 | | | | |
| 0.5 μmol/L Rep 3 | 0.494 | | | | 0.504 | | | | |
| 0.5 μmol/L Rep 4 | 0.515 | | | | 0.494 | | | | |
| 0.5 μmol/L Rep 5 | 0.496 | | | | 0.492 | | | | |
| 0.5 μmol/L Rep 6 | 0.484 | | | | 0.520 | | | | |

| Sample ID | Spiked-in Conc (µmol/L) | Mean Spiked-in Conc. (µmol/L) | SD Spiked-in Conc (µmol/L) | % CV | Dried-down Conc. (µmol/L) | Mean Dried-down Conc. (µmol/L) | SD Spiked-in Conc (µmol/L) | % CV | % Difference from Spiked-in |
|---|---|---|---|---|---|---|---|---|---|
| 0.5 µmol/L Rep 7 | 0.505 | | | | 0.511 | | | | |
| 0.5 µmol/L Rep 8 | 0.507 | | | | 0.501 | | | | |
| 0.5 µmol/L Rep 9 | 0.503 | | | | 0.516 | | | | |
| 0.5 µmol/L Rep 10 | 0.532 | | | | 0.553 | | | | |
| 5 µmol/L Rep 1 | 5.04 | 5.14 | 0.093 | 1.8 | 5.18 | 5.24 | 0.062 | 1.2 | 2.1 |
| 5 µmol/L Rep 2 | 5.26 | | | | 5.38 | | | | |
| 5 µmol/L Rep 3 | 4.99 | | | | 5.24 | | | | |
| 5 µmol/L Rep 4 | 5.17 | | | | 5.20 | | | | |
| 5 µmol/L Rep 5 | 5.10 | | | | 5.28 | | | | |
| 5 µmol/L Rep 6 | 5.07 | | | | 5.25 | | | | |
| 5 µmol/L Rep 7 | 5.17 | | | | 5.24 | | | | |
| 5 µmol/L Rep 8 | 5.08 | | | | 5.21 | | | | |
| 5 µmol/L Rep 9 | 5.25 | | | | 5.29 | | | | |
| 5 µmol/L Rep 10 | 5.22 | | | | 5.17 | | | | |

Conclusion

The calculated concentration and precision (% CV) were in close agreement between the two approaches. This suggests that tubes with pre-dried calibrators at appropriate concentrations can be used for the analysis of unlabeled methotrexate in samples. There was no suggestion of loss or degradation of the materials during drying. This format could be used as a component of a kit designed for the analysis of unlabeled methotrexate.

Example 5: —Internal Calibration Approach for Performing Quantitative LC-MS/MS Analysis of Serum Methotrexate Background Batch mode analysis has limited the utility and throughput of quantitative LC-MS/MS assays. This experiment describes the analysis of methotrexate in serum using $^{13}$C-labeled analogs of methotrexate as internal calibrators. An accurate and precise quantitative result is generated in a single injection, eliminating the need to analyse a traditional set of external calibrators.

Methods

Four $^{13}$C-labeled analogs of methotrexate were designed to minimize isotopic interference. The analogs were used to prepare a 4-point calibration curve over the range 0.025-10 µmol/L. Calibrators were added to each serum sample (50 µL) and proteins were precipitated using methanol. Following centrifugation, the supernatant was diluted and injected onto a Waters HSS-SB C18 UPLC column (2.1×30 mm, 1.8 µm) using a Waters ACQUITY UPLC® I-Class and quantified with a Xevo® TQD mass spectrometer.

For comparison, external quality assessment (EQA) samples supplied by NEQAS (Nottingham, UK; n=14) and WEQAS (Cardiff, UK; n=9) were analyzed using a conventional LC-MS/MS method, in which six non-zero external calibrators were used for quantification. Results were compared with the internal calibrator approach.

Results

Following CLSI EP6-A the calibration range was shown to be linear from 0.0175-13.0 µmol/L, with no detectable carryover up to 100 µmol/L. Coefficients of variation for inter- and intra-method imprecision for 0.1 µmol/L, 1.0 µmol/L, 2.5 µmol/L and 7.5 µmol/L samples were all ≤6.8% (n=25, days=5).

The agreement between the internal calibration approach and the conventional external calibration LC-MS/MS method for the analysis of the EQA samples was described by the Deming equation $y=-0.99x-0.0^2$ (n=23, range 0.025-2.18 µmol/L), demonstrating significant constant bias with no proportional bias (p>0.05). The correlation between the internal calibration approach and the all laboratory trimmed mean (ALTM) for the EQA results was described by the Deming equation y=0.94x+0.03 (n=14, range 0.030-2.14 µmol/L), again demonstrating significant constant bias with no proportional bias (p>0.05).

Interference testing demonstrated a mean recovery of 101% for both endogenous compounds and metabolites tested. Following CLSI EP7-A2, recovery of samples containing 0.1 and 1.0 µmol/L methotrexate (n=3) were unaffected (mean 101.0%, range 95.5-106.3%) when co-spiking with high concentrations of endogenous compounds (albumin, bilirubin, cholesterol, triglycerides and uric acid) and Intralipid©. Similarly, recovery was unaffected (mean 101.1%, range 98.2-104.9%) when methotrexate pools were supplemented with 5 and 50 µmol/L 7-OH methotrexate (n=3) and 4-deoxy-4-amino-$N^{10}$-methylpteroic acid (DAMPA; n=3), showing the absence of interference from these metabolites.

The foregoing internal calibration approach can be used for performing quantitative LC-MS/MS analysis of serum methotrexate in clinical research. Incorporating the calibrators into each test sample allows improved throughput, shorter time to first result, and the possibility of a workflow that does not require samples to be grouped into batches. Additionally, each sample is perfectly matrix-matched as demonstrated by the excellent results of the interference testing (mean bias 101%).

Example 6: Compounds of the Invention

Methotrexate, and synthetic measures for preparing methotrexate are known in the art. See e.g., U.S. Pat. No. 4,080,235 and Medicinal Research Reviews, Vol. 8(1), January/March 1988, 95-155. Isotopically labeled analogues of methotrexate, such as those described herein, can be prepared following known procedures for synthesizing methotrexate using the appropriate isotopically labeled synthons (building blocks). A representative method for synthesizing compounds of Formula I is depicted in Scheme 1. It is to be understood that the synthetic procedures for forming the claims compounds are not limited to the methods described in Scheme 1, but rather extend to processes involving isotopically labeled synthons that are commercially available, or which can be synthesized and used as intermediates for preparing the disclosed compounds.

Benzyl alcohol (Phenyl-$^{13}C_6$), Acetone $^{13}C_3$, and L-glutamic acid $^{13}C_5$ were used as building blocks for the synthesis of internal calibrators for methotrexate. Benzyl alcohol was used in methotrexate $^{13}C_6$ (M+6, compound of Formula IV), methotrexate $^{13}C_{11}$ (M+11, compound of Formula V), and methotrexate $^{13}C_{14}$ (M+14, compound of Formula VII). Acetone $^{13}C_3$ was used in methotrexate $^{13}C_{14}$ (M+14, compound of Formula VII). L-Glutamic acid $^{13}C_5$ was be used in methotrexate $^{13}C_5$ (M+5, compound of formula VI). These starting materials were procured and tested for isotopic purity and distribution by HRMS analysis.

Exemplary Synthesis

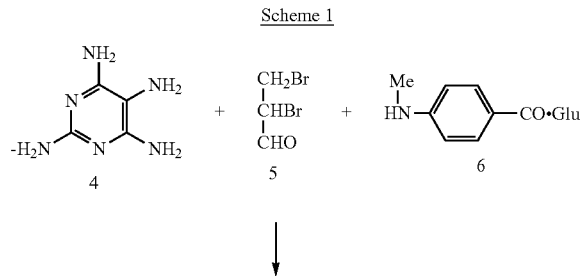

Scheme 1

Compound of Formula IV

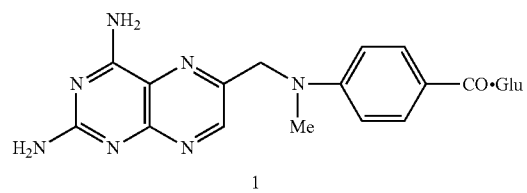

Figure 5:
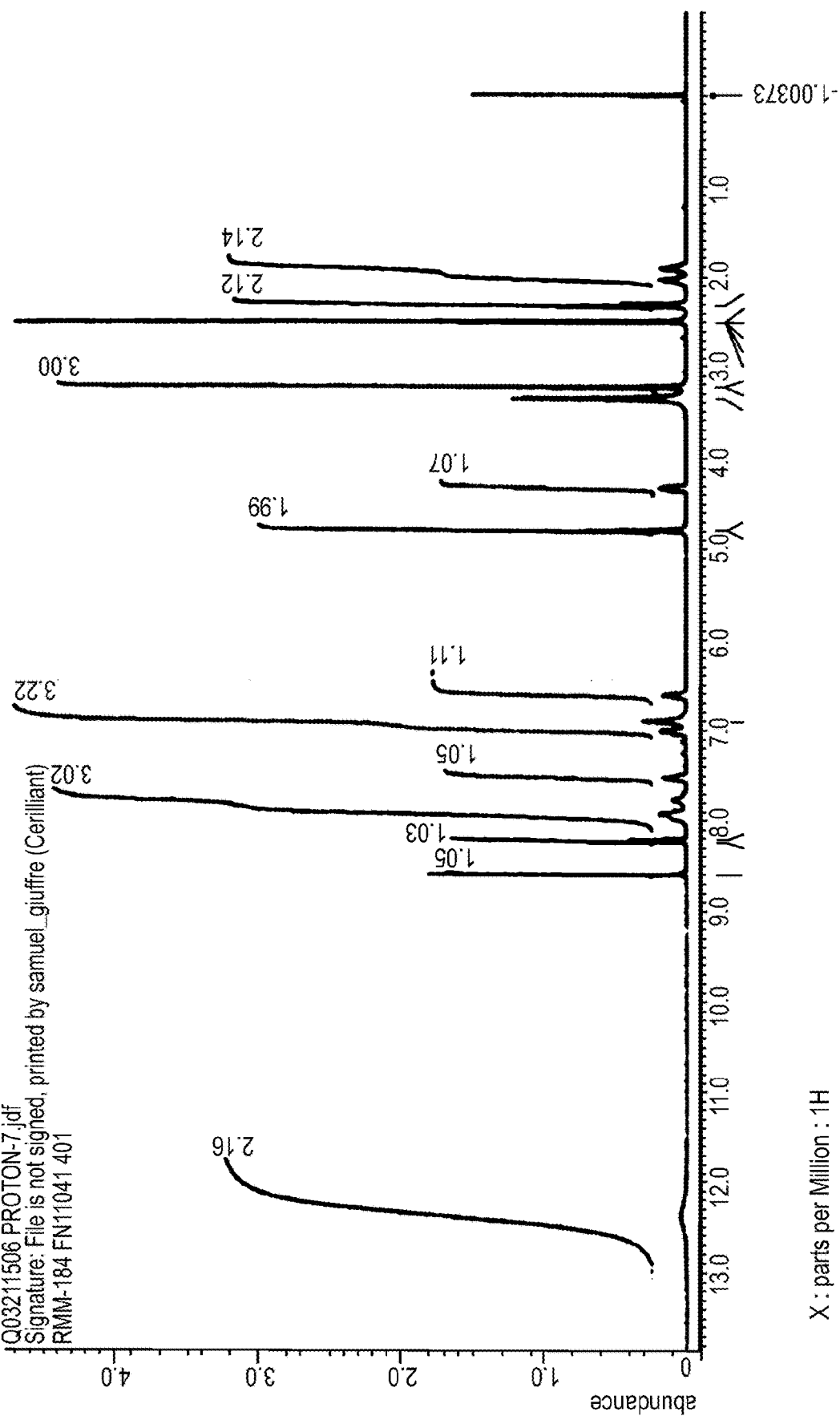
FIG. 5 shows the $^1$H NMR spectrum for compound (IV).
Figure 6:
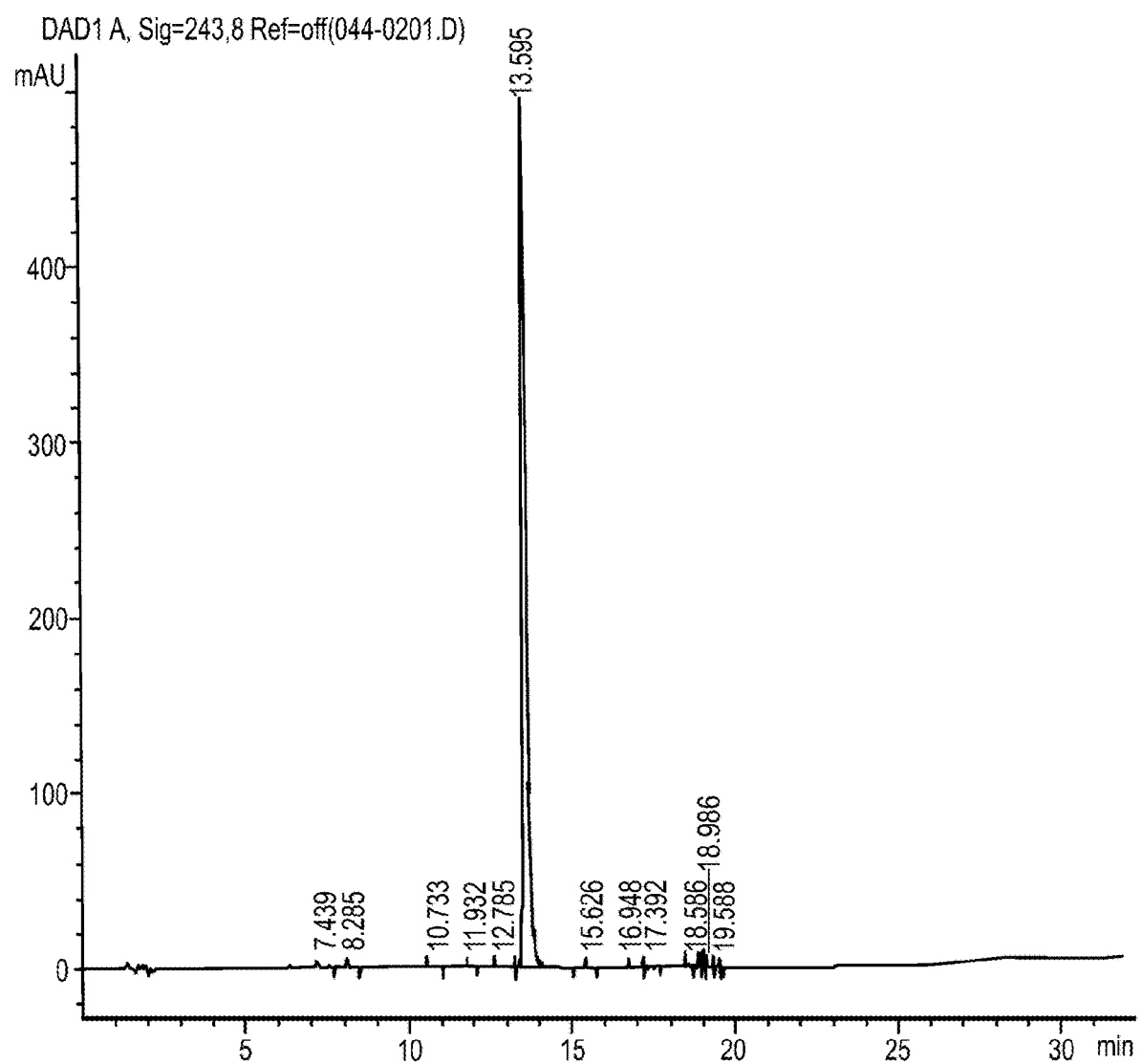
FIG. 6 shows the UPLC/UV purity of compound (IV).

Compounds of Formula (IV) were synthesized as described above using benzyl alcohol (ring-$^{13}C_6$) (e.g., commercially available fromCambridge Isotope Laboratories, Inc., Catalog #CL-2298-0.1). FIG. 5 shows the 1H NMR spectrum obtained for compound (IV). FIG. 6 shows the UPLC/UV purity of compound (IV). Spectral and physical data for compound (IV) are provided below:

(IV)

Spectral and Physical Data

| Analytical Test | Method | Results | |
|---|---|---|---|
| Chromatographic Purity by HPLC/UV Analysis | USP<621>, SP10-0102 | 99.6% [1] | |
| Isotopic Purity Evaluation by LC/MS/MS Analysis | USP<736>, SP10-0107 | MRM Transition Results | |
| | | 455 » 308 | 0.00% |
| | | 460 » 308 | 0.00% |
| | | 461 » 314 | 99.99% |
| | | 466 » 314 | 0.00% |
| | | 469 » 317 | 0.00% |
| Identity by LC/MS Analysis | USP<736>, SP10-0107 | Consistent with Structure | |
| Isotopic Purity and Distribution by High Resolution MS Analysis[2] | USP <736>, SP10-0107 | 0.00% $^{13}C_0$ vs $^{13}C_5$ | |
| | | 0.00% $^{13}C_0$ to $^{13}C_3$ | 96.22% $^{13}C_6$ |
| | | 0.04% $^{13}C_4$ | 0.00% $^{13}C_7$ to $^{13}C_8$ |
| | | 3.75% $^{13}C_5$ | |

| Analytical Test | Method | Results |
| --- | --- | --- |
| Identity by $^1$H-NMR Analysis | USP <761>, SP10-01 IS | Consistent with Structure |
| Residual Solvent by $^1$H-NMR Analysis | USP <761>, SP10-0116 | None Detected |
| Residual Water Analysis by Karl Fischer Coulometry | AM1346[3] | 4.59% |
| ICP-MS Analysis[4] | Outsourced | 166.1 ppm |
| Purity Factor: HPLC Assay[5] | Internal | 86.3% |
| Purity Factor: LCMS Assay[5] | Internal | 55.7% |

[1] Purity value is the average of two independent analyses
[2] Isotopic distribution values are adjusted for the natural abundance of isotopes (M + 1 adjusted 18.52%; M + 2 adjusted 2.66%; M + 3 adjusted 0.28%)
[3] Validated analytical method
[4] Counter ion to Na+ by Ion Chromatography confirmed to be CL
[5] Assay performed by generating a 100 μg/mL solution m Methanol with 0.1N Sodium hydroxide, and comparing against a Certified Reference Standard of 100 μg/mL Methotrexate or Methotrexate-D3 in Methanol with 0.1N Sodium hydroxide.

| | |
| --- | --- |
| Purity Factor: | HPLC Assay |
| Analysis Method: | HPLC/UV |
| Column: | Prodigy ODS3. 5 μm. 4.6 × 250 mm |
| Mobile Phase: | Acetonitrile::0.1% Phosphoric acid in Water (15::85) |
| Flow Rite: | 1.0 mL/min |
| Wavelength: | 243 nm |
| Check Standard | |
| Check Standard: | Methotrexate-D$_3$. Primary Standard |
| Certified Concentration: | 100.0 ± 0.9 μg ml |

| Sample IV | Prepared Concentration | Verified Concentration | No. of Injections | % RSD - Homogeneity |
| --- | --- | --- | --- | --- |
| | 100.0 μg/mL | 86.3 μg/mL | 6 | 1.6 |

* Concentration is verified through multiple analyses and is calculated as the average of multiple analyses compared to an independently prepared check standard.

| | |
| --- | --- |
| Purity Factor: | LC/MS Assay |
| Analysis Method: | LC/MS |
| Column: | Kinetex. 2.6 μm. 2.1 × 50 mm |
| Mobile Phase: | 0.1% Formic acid m Water::Acetonitrile (90:: 10) |
| Flow Rate: | 0.3 mL/min |
| Polarity: | MRM, Positive Ion |
| Check Standard 1 | |
| Check Standard: | Methotrexate Primary Standard |
| Certified Concentration: | 1.000 ± 0.005 mg/mL |

| Sample | Prepared Concentration | Verified Concentration | No. of Injections | % RSD - Homogeneity |
| --- | --- | --- | --- | --- |
| | 100.0 μg/mL | 55.7 μg/mL | 6 | 4.0 |

*Concentration is verified through multiple analyses and is calculated as the average of multiple analyses compared to an independently prepared check standard.
[1] Check standard diluted 1:10 from 1.000 mg/mL to 100.0 μg/mL for comparison to Sample IV.

Identity by LC/MS

| | |
| --- | --- |
| Column: | Ascentis Express Phenyl-Hexyl, 2.7 μm. 3.0 × 50 mm |
| Mobile Phase: | A:: 0.1% Formic Acid in Water |
| | B:: Acetonitrile |
| Flow Rate: | 0.4 mL/min |
| Scan Range: | 100-1200 amu |
| Ionization: | Electrospray. Positive Ion |
| Instrument: | Waters XEVO G2 QTOF |
| Acquired: | May 22, 2015 |

| Gradient: | Time (min) | % A | % B |
| --- | --- | --- | --- |
| | 0.0 | 90 | 10 |
| | 5.0 | 70 | 30 |
| | 6.0 | 70 | 30 |
| | 6.1 | 90 | 10 |
| | 8.0 | 90 | 10 |

Isotopic Purity Evaluation by LC/MS/MS

| | |
| --- | --- |
| Column: | Kinetex, 2.6 μm, 2. |
| Mobile Phase: | A:: 0.1% Formic Acid in Water::Acetonitrile (90::10) |
| Flow Rate: | 0.3 mL/min |
| Ionization: | Electrospray Positive Ion |
| Instrument: | Agilent 6410A Mass Spectrometer |
| Acquired: | May 22, 2015 |

| Compound m/z | MRM Transition | Transition area % |
|---|---|---|
| 455 (native) | 455 » 308 | 0.00% |
| 460 (m/z for M + 5) | 460 » 314 | 0.00% |
| 461 (m/z for M + 6) | 461 » 314 | >99.99% |
| 466 (m/z for M + 11) | 466 » 314 | 0.00% |
| 469 (m/z for M + 14) | 469 » 317 | 0.00% |

Isotopic Purity by High Resolution MS

| | |
|---|---|
| Column: | Ascentis Express Phenyl-Hexyl, 2.7 μm, 3.0 × 50 mm |
| Mobile Phase: | A:: 0.1% Formic Acid in Water |
| | B:: Acetonitrile |
| Flow Rate: | 0.4 mL/min |
| Scan Range: | 455-463 amu |
| Ionization: | Electrospray, Positive Ion |
| Instrument: | Waters XEVO G2 QTOF |
| Acquired: | May 22, 2015 |

| Gradient: | Time (min) | % A | % B |
|---|---|---|---|
| | 0.0 | 90 | 10 |
| | 5.0 | 70 | 30 |
| | 6.0 | 70 | 30 |
| | 6.1 | 90 | 10 |
| | 8.0 | 90 | 10 |

| | Area | Isotopic % | Adjusted Area | Adjusted Isotopic % | |
|---|---|---|---|---|---|
| $^{13}C$ | 0 | 0.000 | 0 | 0.000 | Adjusted area and isotopic |
| $^{13}_0C$ | 0 | 0.000 | 0 | 0.000 | distribution values are adjusted |
| $^{13}_1C$ | 0 | 0.000 | 0 | 0.000 | for the natural abundance of |
| $^{13}_2C$ | 0 | 0.000 | 0 | 0.000 | isotopes. In this case area for |
| $^{13}_3C$ | 12 | 0.029 | 12 | 0.035 | M + 1 is adjusted 18.52%; M + 2 is |
| $^{13}_4C$ | 1282 | 3.123 | 1280 | 3.747 | adjusted 2.66%; and M + 3 is |
| $^{13}_5C$ | 33098 | 80.617 | 2861 | 6.218 | adjusted 0.28%. If adjusted areas |
| $^{13}_6C$ | 5852 | 14.254 | 0 | 0.000 | were negative numbers, they were |
| $^{13}_7C$ | 812 | 1.978 | 0 | 0.000 | set to a value of zero. |
| $^8$Sum | 41056 | — | 34152 | — | |
| $^{13}C_0/^{13}C_6 \times 100$ | | 0.000 | | 0.000 | |

Compound of Formula V

Figure 7:
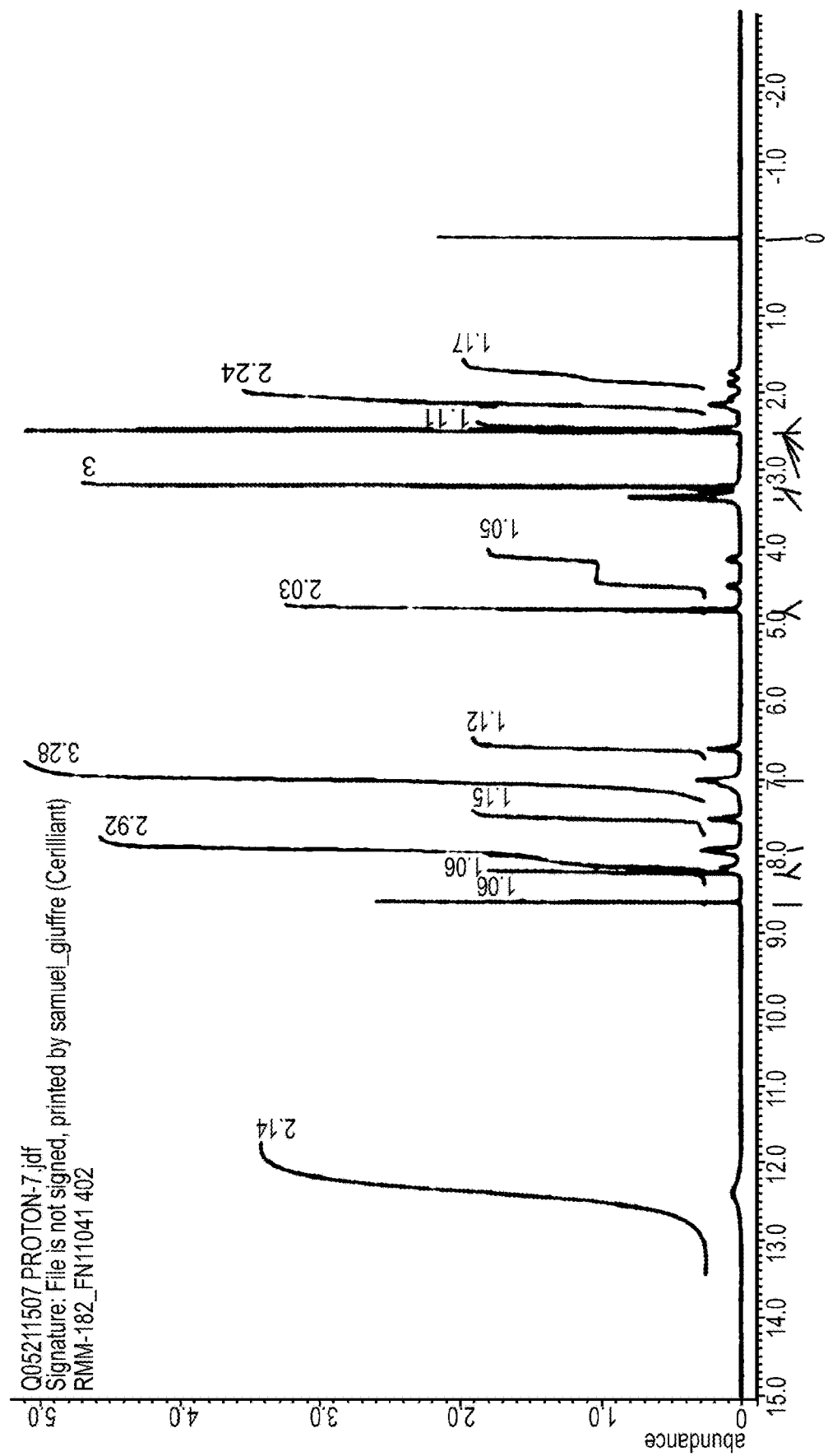
FIG. 7 shows the H NMR spectrum for compound (V).
Figure 8:
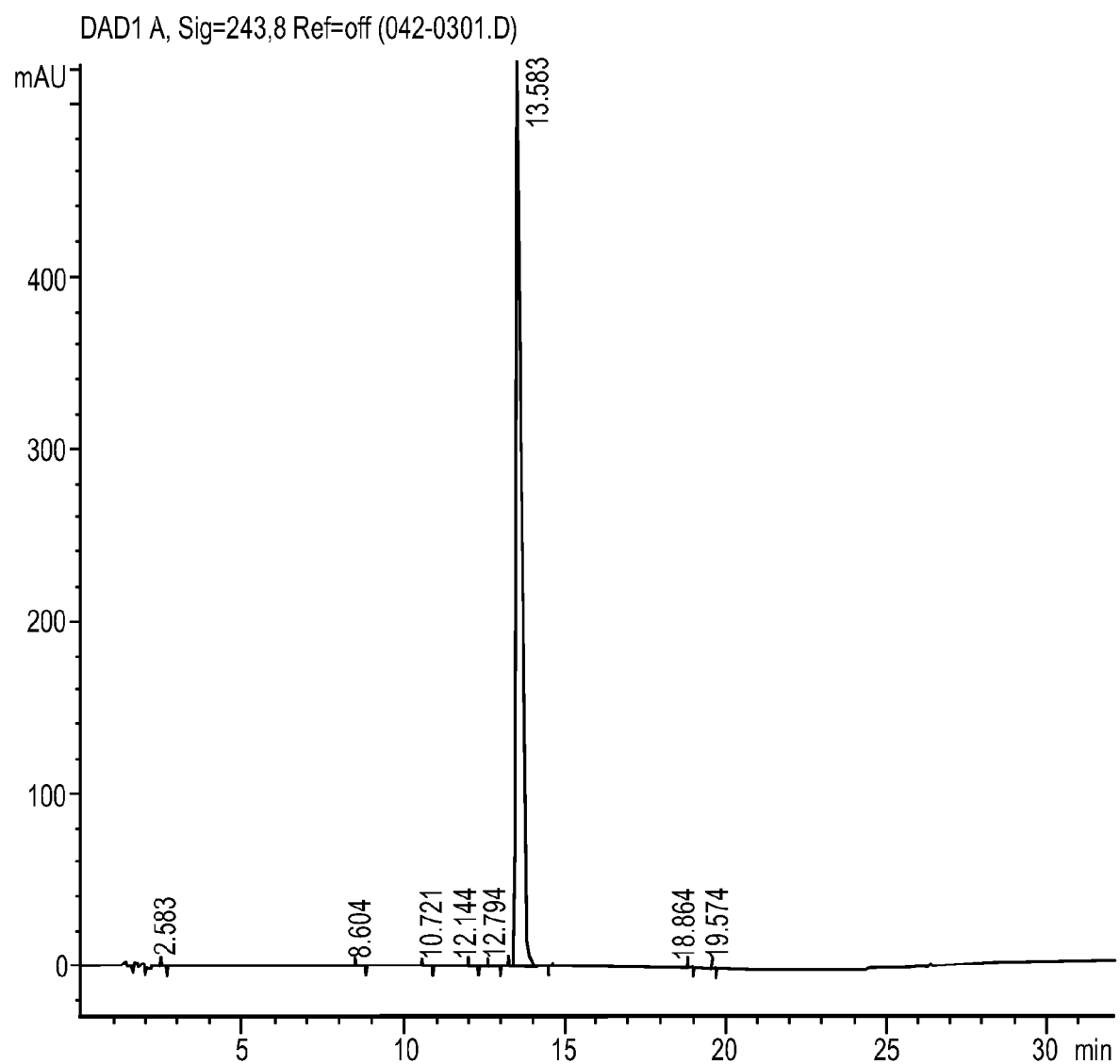
FIG. 8 shows the UPLC/UV purity of compound (V).

Compounds of Formula (V) were synthesized as described above using L-glutamic acid-$^{13}C_5$ (e.g., commercially available from Sigma-Aldrich, Catalog #60480), benzyl alcohol (ring-$^{13}C_6$) (commercially available from Cambridge Isotope Laboratories, Inc., Catalog #CL-2298-0.1). FIG. 7 shows the 1H NMR spectrum obtained for compound (V). FIG. 8 shows the UPLC/UV purity of compound (V). Spectral and physical data for compound (V) are provided below:

(V)

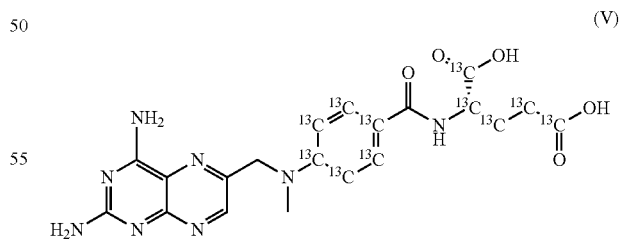

Spectral and Physical Data

| Analytical Test | Method | Results |
|---|---|---|
| Chromatographic Purity by HPLC/UV Analysis | USP<621>, SP10-0102 | 99.6% [1] |
| Isotopic Purity Evaluation by LC/MS/MS Analysis | USP <736>, SP10-0107 | MRM Transition Results |
| | | 455 » 308   0.00% |

| Analytical Test | Method | Results | | |
| --- | --- | --- | --- |
| | | 460 » 308 | 0.00% |
| | | 461 » 314 | 0.01% |
| | | 466 » 314 | 99.94% |
| | | 469 » 317 | 0.04% |
| Identity by LC/MS Analysis | USP<736>, SP10-0107 | Consistent with Structure | |
| Isotopic Purity and Distribution by High Resolution MS Analysis | USP <736>, SP10-0107 | 0.00% $^{13}C_0$ vs $^{13}C_{11}$ | |
| | | 0.00% $^{13}C_0$ to $^{13}C_7$ | 6.69% $^{13}C_{10}$ |
| | | 0.01% $^{13}C_8$ | 93.19% $^{13}C_{11}$ |
| | | 0.12% $^{13}C_9$ | |
| Identity by $^1$H-NMR Analysis | USP <761>, SP10-01 IS | Consistent with Structure | |
| Residual Solvent by $^1$H-NMR Analysis | USP <761>, SP10-0116 | None Detected | |
| Residual Water Analysis by Karl Fischer Coulometry | AM1346[2] | 2.30% | |
| ICP-MS Analysis[3] | Outsourced | 144 ppm Na$^+$ | |
| Purity Factor: HPLC Assay[4] | Internal | 85.4% | |
| Purity Factor: LGMS Assay[4] | Internal | 56.1% | |

[1] Purity value is the average of two independent analyses
[2] Validated analytical method
[3] Counter ion to Na+ by Ion Chromatography confirmed to be CL
[4] Assay performed by generating a 100 μg/mL solution m Methanol with 0.1N Sodium hydroxide, and comparing against a Certified Reference Standard of 100 μg/mL Methotrexate or Methotrexate-D3 in Methanol with 0.1N Sodium hydroxide.

| | |
| --- | --- |
| Purity Factor: | HPLC Assay |
| Analysis Method: | HPLC/UV |
| Column: | Prodigy ODS3. 5 μm. 4.6 × 250 mm |
| Mobile Phase: | Acetonitrile::0.1% Phosphoric acid in Water (15::85) |
| Flow Rate: | 1.0 mL/min |
| Wavelength: | 243 nm |
| Check Standard | |
| Check Standard: | Methotrexate-D$_3$. Primary Standard |
| Certified Concentration: | 100.0 ± 0.9 μg ml |

| Sample V | Prepared Concentration | Verified Concentration | No. of Injections | % RSD - Homogeneity |
| --- | --- | --- | --- | --- |
| | 100.0 μg/mL | 85.4 μg/mL | 6 | 0.2 |

* Concentration is verified through multiple analyses and is calculated as the average of multiple analyses compared to an independently prepared check standard.

| | |
| --- | --- |
| Purity Factor: | LC/MS Assay |
| Analysis Method: | LC/MS |
| Column: | Kinetex. 2.6 μm. 2.1 × 50 mm |
| Mobile Phase: | 0.1% Formic acid m Water::Acetonitrile (90::10) |
| Flow Rate: | 0.3 mL/min |
| Polarity: | MRM, Positive Ion |
| Check Standard[1] | |
| Check Standard: | Methotrexate Primary Standard |
| Certified Concentration: | 1.000 ± 0.005 mg/mL |

| Sample | Prepared Concentration | Verified Concentration | No. of Injections | % RSD - Homogeneity |
| --- | --- | --- | --- | --- |
| | 100.0 μg/mL | 56.1 μg/mL | 6 | 3.2 |

*Concentration is verified through multiple analyses and is calculated as the average of multiple analyses compared to an independently prepared check standard.
[1] Check standard diluted 1:10 from 1.000 mg/mL to 100.0 μg/mL for comparison to Sample V.

| | |
| --- | --- |
| Column: | Ascentis Express Phenyl-Hexyl, 2.7 μm. 3.0 × 50 mm |
| Mobile Phase: | A:: 0.1% Formic Acid in Water |
| | B:: Acetonitnle |
| Flow Rate: | 0.4 mL/min |
| Scan Range: | 100-1200 amu |
| Ionization: | Electrospray. Positive Ion |
| Instrument: | Waters XEVO G2 QTOF |
| Acquired: | May 22, 2015 |

| Gradient: | Time (min) | % A | % B |
| --- | --- | --- | --- |
| | 0.0 | 90 | 10 |
| | 5.0 | 70 | 30 |
| | 6.0 | 70 | 30 |
| | 6.1 | 90 | 10 |
| | 8.0 | 90 | 10 |

Isotopic Purity Evaluation by LC/MS/MS

| Column: | Kinetex, 2.6 µm, 2. | Instrument: | Agilent 6410A Mass Spectrometer |
|---|---|---|---|
| Mobile Phase: | A::0.1% Formic Acid in Water::Acetonitrile (90::10) | Acquired: | May 22, 2015 |
| Flow Rate: | 0.3 mL/min | | |
| Ionization: | Electrospray Positive Ion | | |

| Compound m/z | MRM Transition | Transition area % |
|---|---|---|
| 455 (native) | 455 » 308 | 0.00% |
| 460 (m/z for M + 5) | 460 » 314 | 0.00% |
| 461 (m/z for M + 6) | 461 » 314 | 0.01% |
| 466 (m/z for M + 11) | 466 » 314 | 99.94% |
| 469 (m/z for M + 14) | 469 » 317 | 0.04% |

Isotopic Purity by High Resolution MS

| Column: | Ascentis Express Phenyl-Hexyl, 2.7 µm, 3.0 × 50 mm |
|---|---|
| Mobile Phase: | A: 0.1% Formic Acid in Water |
| | B: Acetonitrile |
| Flow Rate: | 0.4 mL/min |
| Scan Range: | 455-463 amu |
| Ionization: | Electrospray, Positive Ion |
| Instrument: | Waters XEVO G2 QTOF |
| Acquired: | May 22, 2015 |
| Instrument: | Waters XEVO G2 QTOF |
| Acquired: | May 22, 2015 |

| Gradient: | Time (min) | % A | % B |
|---|---|---|---|
| | 0.0 | 90 | 10 |
| | 5.0 | 70 | 30 |
| | 6.0 | 70 | 30 |
| | 6.1 | 90 | 10 |
| | 8.0 | 90 | 10 |

Compound of Formula VI

Figure 9:
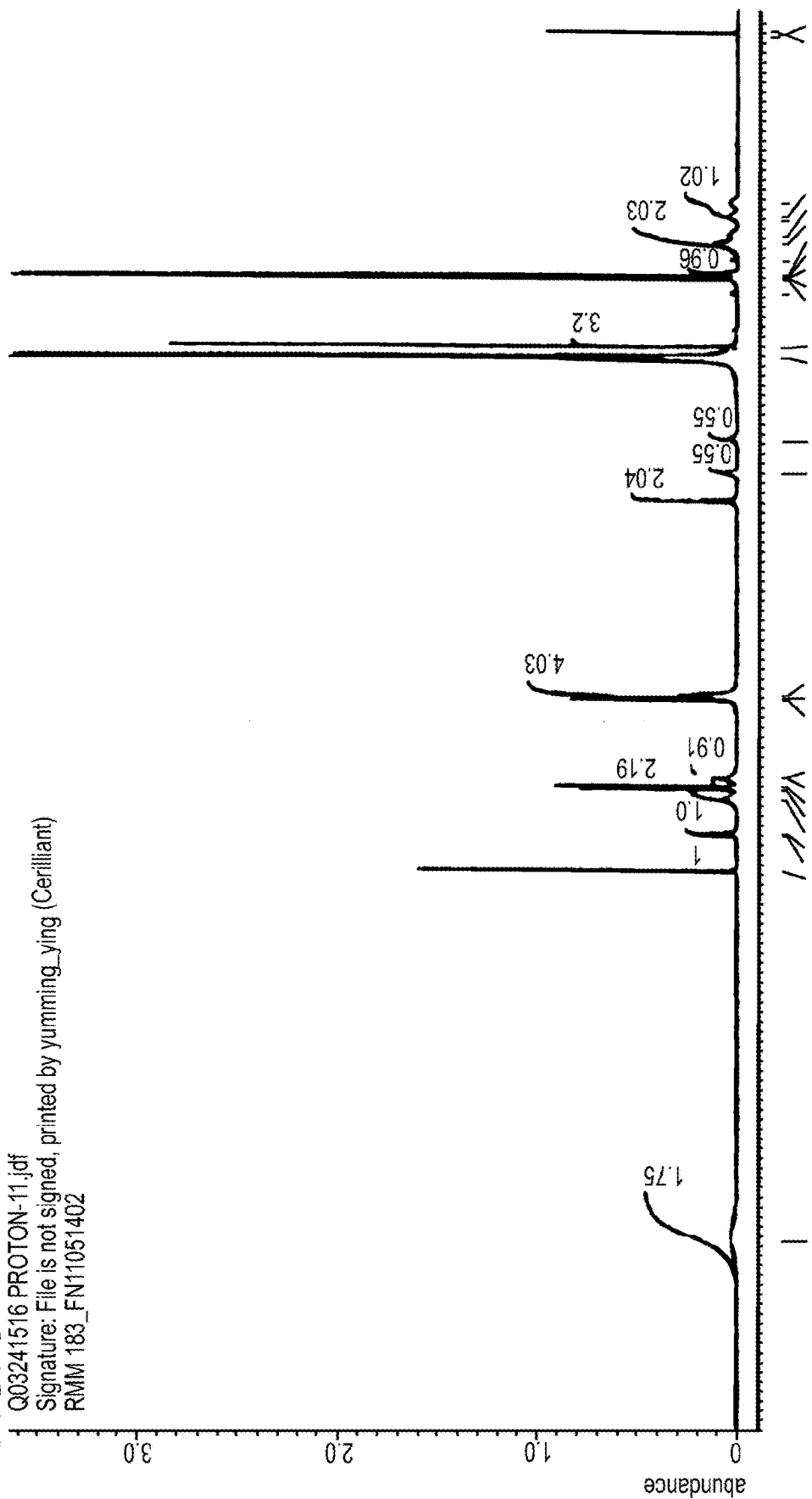
FIG. 9 shows the H NMR spectrum for compound (VI).
Figure 10:
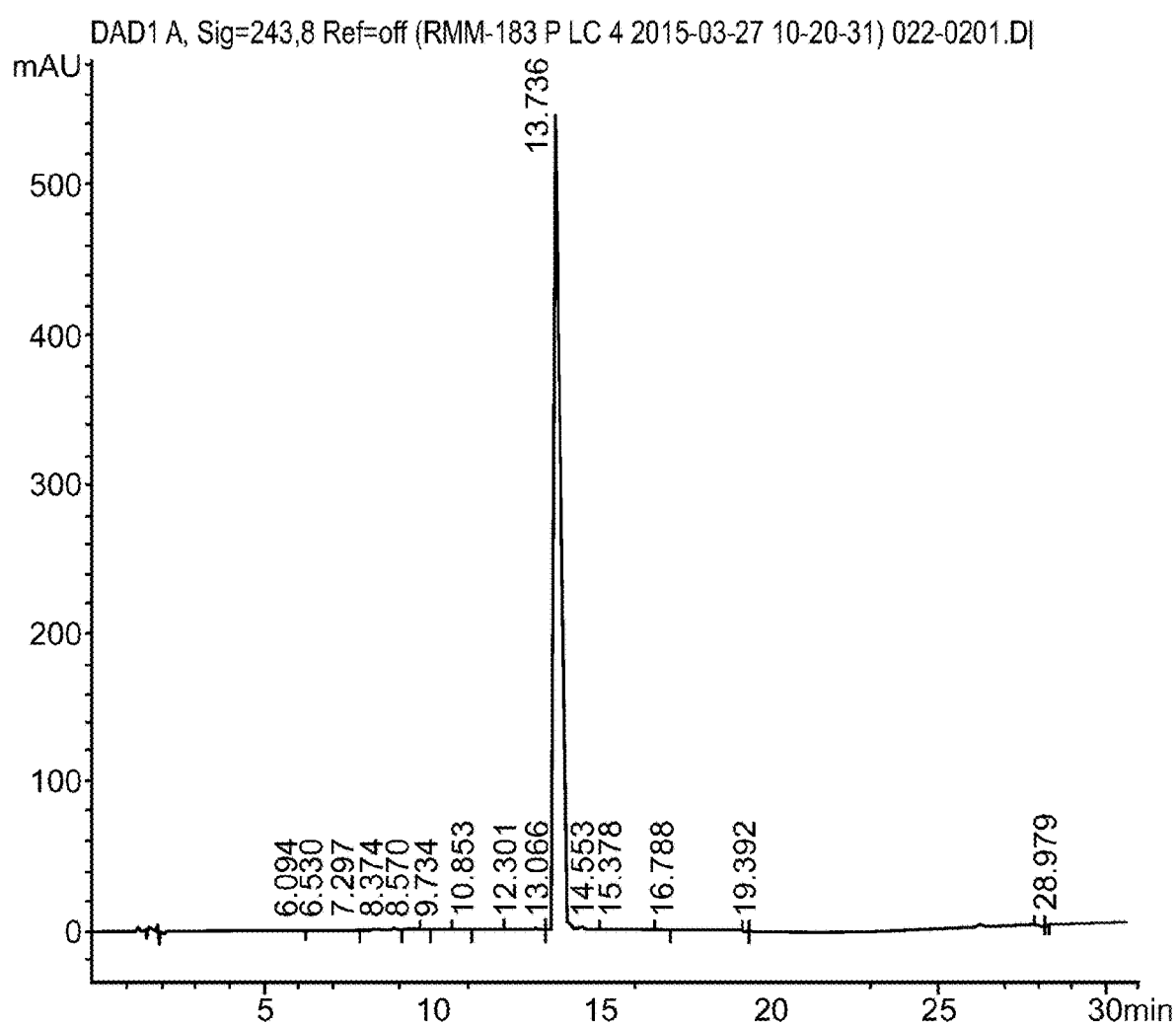
FIG. 10 shows the UPLC/UV purity of compound (VI).

Compounds of Formula (VI) were synthesized as described above using L-glutamic acid-$^{13}C_5$ (e.g., commercially available from Sigma-Aldrich, Catalog #60480). FIG. 9 shows the 1H NMR spectrum obtained for compound (VI). FIG. 10 shows the UPLC/UV purity of compound (VI). Spectral and physical data for compound (VI) are provided below:

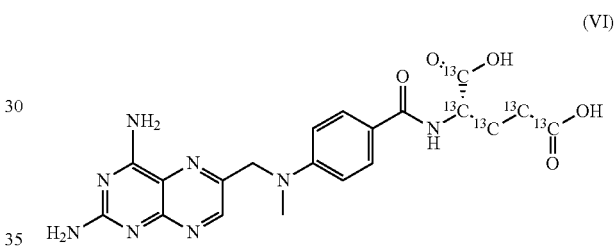

(VI)

Spectral and Physical Data

| Analytical Test | Method | Results |
|---|---|---|
| Chromatographic Purity by HPLC/UV Analysis | USP<621>, SP10-0102 | 98.5% [1] |
| Isotopic Purity Evaluation by LC/MS/MS Analysis | USP <736>, SP10-0107 | MRM Transition Results |
| | | 455 » 308    0.00% |
| | | 460 » 308    >99.99% |
| | | 461 » 314    0.00% |
| | | 466 » 314    0.00% |
| | | 469 » 317    0.00% |
| Identity by LC/MS Analysis | USP<736>, SP10-0107 | Consistent with Structure |
| Isotopic Purity and Distribution by High Resolution MS Analysis[2] | USP <736>, SP10-0107 | 0.00% $^{13}C_0$ vs $^{13}C_5$ |
| | | 0.00% $^{13}C_0$ to $^{13}C_1$    3.54% $^{13}C_4$ |
| | | 0.01% $^{13}C_2$    96.36% $^{13}C_5$ |
| | | 0.09% $^{13}C_3$    0.00% $^{13}C_6$ to $^{13}C_8$ |
| Identity by $^1$H-NMR Analysis | USP <761>, SP10-01 IS | Consistent with Structure |
| Residual Solvent by $^1$H-NMR Analysis | USP <761>, SP10-0116 | None Detected |
| Residual Water Analysis by Karl Fischer Coulometry | AM1346[3] | 2.96% |
| ICP-MS Analysis[4] | Outsourced | 0.70% $Na^+$ |
| Purity Factor: HPLC Assay[5] | Internal | 89.8% |
| Purity Factor: LCMS Assay[5] | Internal | 54.6% |

[1] Purity value is the average of two independent analyses
[2] Isotopic distribution values are adjusted for the natural abundance of isotopes (M + 1 adjusted 19.66%; M + 2 adjusted 2.87%; M + 3 adjusted 0.31%)
[3] Validated analytical method
[4] Counter ion to Na+ by Ion Chromatography confirmed to be CL
[5] Assay performed by generating a 100 µg/mL solution m Methanol with 0.1N Sodium hydroxide, and comparing against a Certified Reference Standard of 100 µg/mL Methotrexate or Methotrexate-D3 in Methanol with 0.1N Sodium hydroxide.

| Purity Factor: | HPLC Assay | Check Standard | |
|---|---|---|---|
| Analysis Method: | HPLC/UV | Check Standard: | Methotrexate-$D_3$. Primary Standard |
| Column: | Prodigy ODS3. 5 µm. 4.6 × 250 mm | Certified Concentration: | 100.0 ± 0.9 µg ml |
| Mobile Phase: | Acetonitrile::0.1% Phosphoric acid in | | |

| | | | | |
|---|---|---|---|---|
| Flow Rite: | Water (15::85) | | | |
| Wavelength: | 1.0 mL/min | | | |
| | 243 nm | | | |

| Sample VI | Prepared Concentration | Verified Concentration | No. of Injections | % RSD - Homogeneity |
|---|---|---|---|---|
| | 1.000 mg/mL | 0.898 mg/mL | 6 | 2.2 |

* Concentration is verified through multiple analyses and is calculated as the average of multiple analyses compared to an independently prepared check standard.

| | | | |
|---|---|---|---|
| Purity Factor: | LC/MS Assay | Check Standard 1 | |
| Analysis Method: | LC/MS | Check Standard: | Methotrexate Primary Standard |
| Column: | Kinetex. 2.6 μm. 2.1 × 50 mm | Certified Concentration: | 1.000 ± 0.005 mg/mL |
| Mobile Phase: | 0.1% Formic acid m Water::Acetonitrile (90:: 10) | | |
| Flow Rate: | 0.3 mL/min | | |
| Polarity: | MRM, Positive Ion | | |

| Sample | Prepared Concentration | Verified Concentration | No. of Injections | % RSD - Homogeneity |
|---|---|---|---|---|
| | 1.000 mg · mL | 0.546 mg/mL | 6 | 0.7 |

*Concentration is verified through multiple analyses and is calculated as the average of multiple analyses compared to an independently prepared check standard.
[1] Check standard diluted 1:10 from 1.000 mg/mL to 100.0 μg/mL for comparison to Sample VI.

Identity by LC/MS

| | |
|---|---|
| Column: | Ascentis Express Phenyl-Hexyl, 2.7 μm. 3.0 × 50 mm |
| Mobile Phase: | A:: 0.1% Formic Acid in Water<br>B:: Acetonitrile |
| Flow Rate: | 0.4 mL/min |
| Scan Range: | 100-1200 amu |
| Ionization: | Electrospray. Positive Ion |
| Instrument: | Waters XEVO G2 QTOF |
| Acquired: | May 22, 2015 |

| Gradient: | Time (min) | % A | % B |
|---|---|---|---|
| | 0.0 | 90 | 10 |
| | 5.0 | 70 | 30 |
| | 6.0 | 70 | 30 |
| | 6.1 | 90 | 10 |
| | 8.0 | 90 | 10 |

Isotopic Purity Evaluation by LC/MS/MS

| | | | |
|---|---|---|---|
| Column: | Kinetex, 2.6 μm, 2. | Instrument: | Agilent 6410A Mass Spectrometer |
| Mobile Phase: | A:: 0.1% Formic Acid in Water::Acetonitrile (90::10) | Acquired: | May 22, 2015 |
| Flow Rate: | 0.3 mL/min | | |
| Ionization: | Electrospray Positive Ion | | |

| Compound m/z | MRM Transition | Transition area % |
|---|---|---|
| 455 (native) | 455 » 308 | 0.00% |
| 460 (m/z for M + 5) | 460 » 314 | >99.99% |
| 461 (m/z for M + 6) | 461 » 314 | 0.00% |
| 466 (m/z for M + 11) | 466 » 314 | 0.00% |
| 469 (m/z for M + 14) | 469 » 317 | 0.00% |

Isotopic Purity by High Resolution MS

| | | | | |
|---|---|---|---|---|
| Column: | Ascentis Express Phenyl-Hexyl, 2.7 µm, 3.0 × 50 mm | | | |
| Mobile Phase: | A: 0.1% Formic Acid in Water | | | |
| | B: Acetonitrile | | | |
| Flow Rate: | 0.4 mL/min | | | |
| Scan Range: | 455-463 amu | | | |
| Ionization: | Electrospray, PositiveIon | | | |
| Instrument: | Waters XEVO G2 QTOF | | | |
| Acquired: | May 22, 2015 | | | |

| Gradient: | Time (min) | % A | % B |
|---|---|---|---|
| | 0.0 | 90 | 10 |
| | 5.0 | 70 | 30 |
| | 6.0 | 70 | 30 |
| | 6.1 | 90 | 10 |
| | 8.0 | 90 | 10 |

| | Area | Isotopic % | Adjusted Area | Adjusted Isotopic % | |
|---|---|---|---|---|---|
| $^{13}C$ | 1 | 0.002 | 1 | 0.003 | Adjusted area and isotopic |
| $^{13}C_0$ | 1 | 0.002 | 1 | 0.002 | distribution values are adjusted |
| $^{13}C_1$ | 3 | 0.007 | 3 | 0.008 | for the natural abundance of |
| $^{13}C_2$ | 33 | 0.075 | 32 | 0.090 | isotopes. In this case area for |
| $^{13}C_3$ | 1279 | 2.894 | 1273 | 3.535 | M + 1 is adjusted 19.66%; M + 2 is |
| $^{13}C_4$ | 34944 | 79.061 | 34693 | 96.363 | adjusted 2.87%; and M + 3 is |
| $^{13}C_5$ | 6857 | 15.514 | 0 | 0.000 | adjusted 0.31%. If adjusted areas |
| $^{13}C_6$ | 996 | 2.253 | 0 | 0.000 | were negative numbers, they were |
| $^{13}C_7$ | 85 | 0.192 | 0 | 0.000 | set to a value of zero. |
| $^8$Sum | 44199 | — | 36002 | — | |
| $^{13}C_0/^{13}C_5 \times 100$ | | 0.003 | | 0.003 | |

Compound of Formula VII

Figure 11:
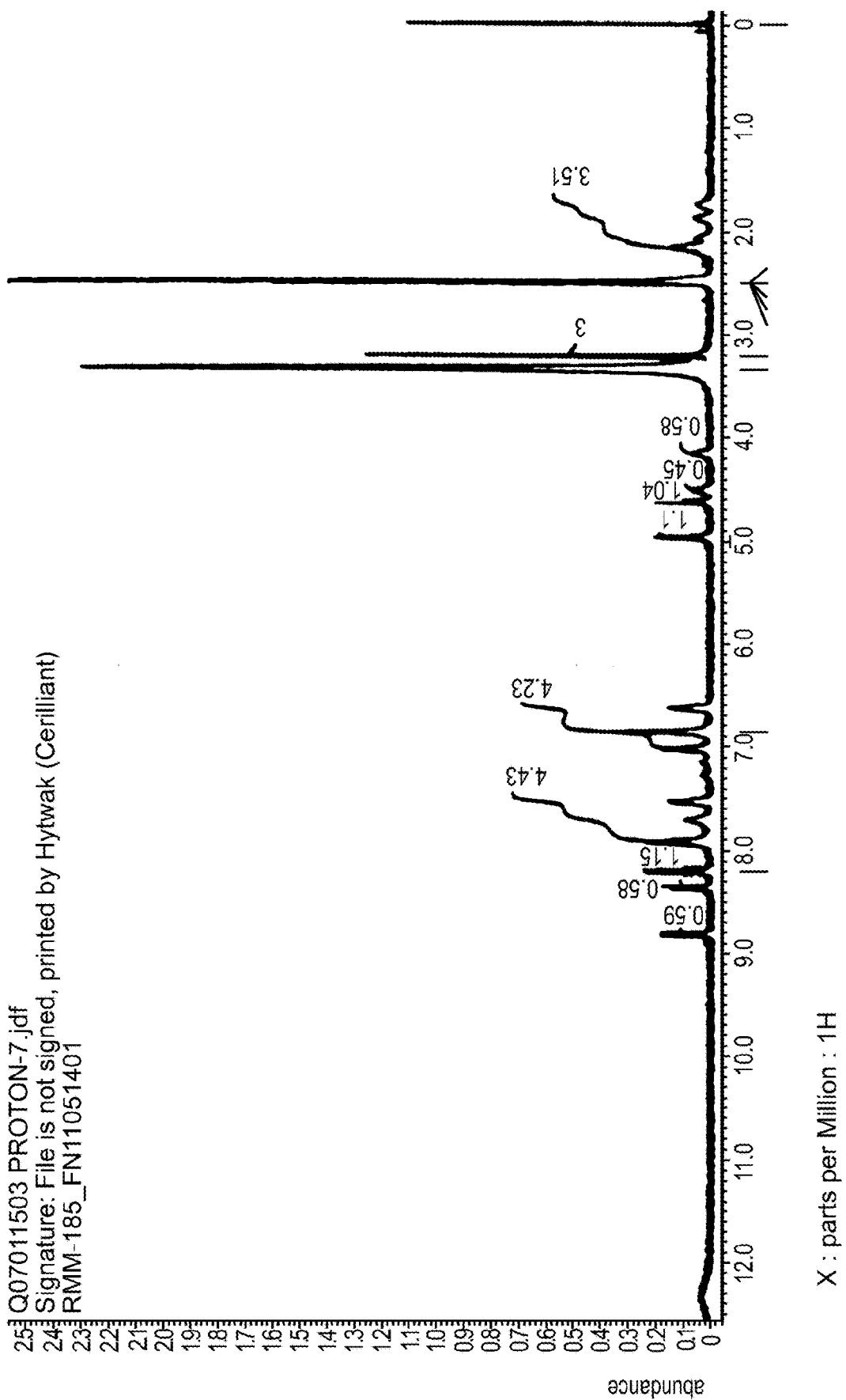
FIG. 11 shows the $^1$H NMR spectrum for compound (VII).
Figure 12:
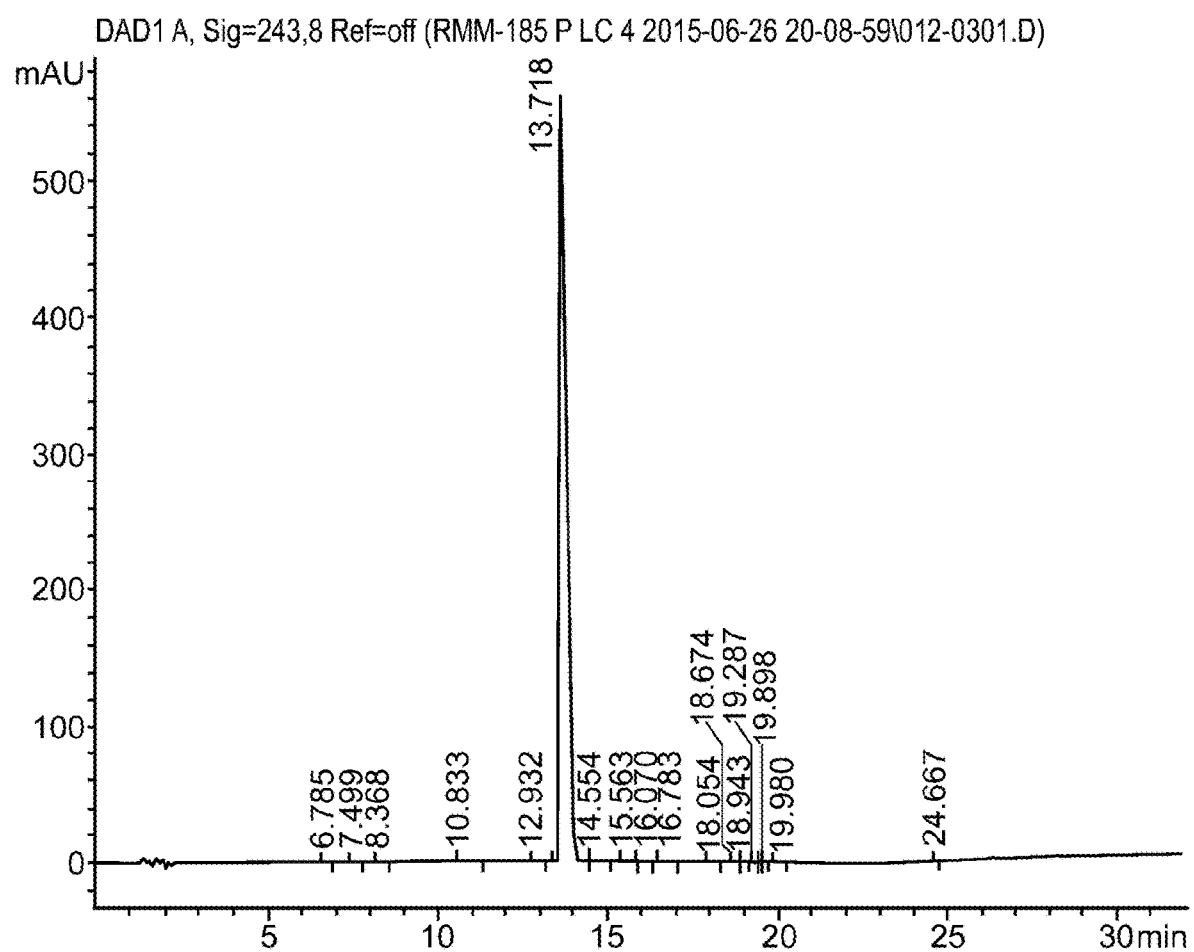
FIG. 12 shows the UPLC/UV purity of compound (VII).
Figure 13:
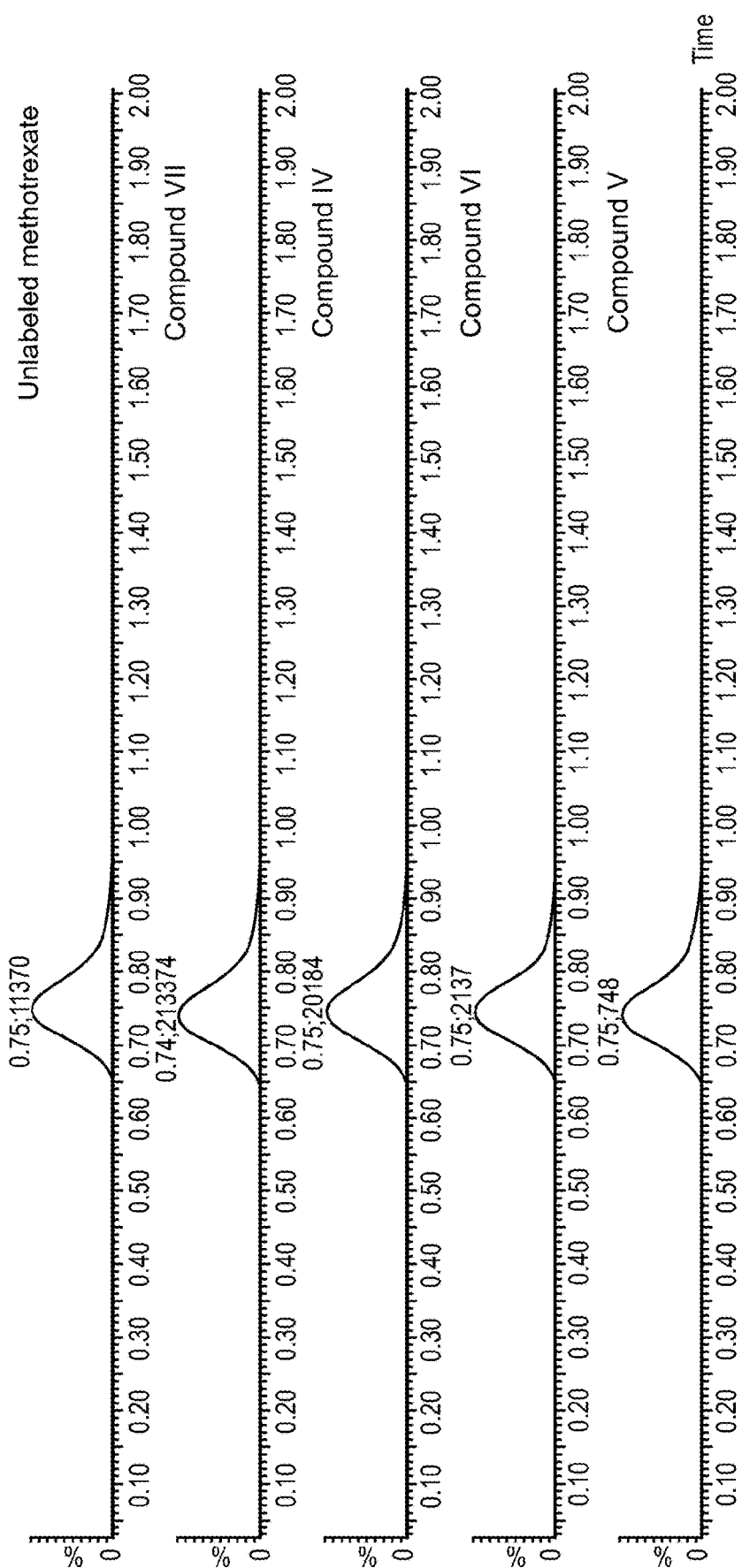
FIG. 13 shows a chromatogram demonstrating the co-elution of compounds (IV)-(VIII) with unlabeled methotrexate.

Compounds of Formula (VII) were synthesized as described above using L-glutamic acid-$^{13}C_5$ (e.g., commercially available from Sigma-Aldrich, Catalog #60480), benzyl alcohol (ring-$^{13}C_6$) (commercially available from Cambridge Isotope Laboratories, Inc., Catalog #CL-2298-0.1), and acetone-$^{13}C_3$ (commercially available from Sigma-Aldrich, Catalog #491667). FIG. 11 shows the 1H NMR spectrum obtained for compound (VII). FIG. 12 shows the UPLC/UV purity of compound (VII). Spectral and physical data for compound (VII) are provided below:

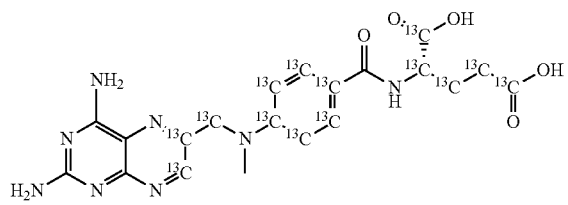 [SMILES: CN(C[13CH]1[13CH]=Nc2nc(N)nc(N)c2N1)[13CH]1[13CH]=[13CH][13C](C(=O)N[13C@@H]([13CH2][13CH2][13C](=O)O)[13C](=O)O)=[13CH][13CH2]1]

(VII)

Spectral and Physical Data

| Analytical Test | Method | Results |
|---|---|---|
| Chromatographic Purity by HPLC/UV Analysis | USP<621>, SP10-0102 | 99.7% [1] |
| Isotopic Purity Evaluation by LC/MS/MS Analysis | USP<736>, SP10-0107 | MRM Transition Results |
| | | 455 » 308   0.00% |
| | | 460 » 308   0.00% |
| | | 461 » 314   0.00% |
| | | 466 » 314   0.01% |
| | | 469 » 317   99.99% |
| Identity by LC/MS Analysis | USP<736>, SP10-0107 | Consistent with Structure |
| Isotopic Purity and Distribution by High Resolution MS Analysis | USP <736>, SP10-0107 | 0.00% $^{13}C_0$ vs $^{13}C_{14}$ |
| | | 0.00% $^{13}C_0$ to $^{13}C_{10}$   8.97% $^{13}C_{13}$ |
| | | 0.01% $^{13}C_{11}$   90.66% $^{13}C_{14}$ |
| | | 0.35% $^{13}C_{12}$ |
| Identity by $^1$H-NMR Analysis | USP <761>, SP10-01 IS | |
| Residual Solvent by $^1$H-NMR Analysis | USP <761>, SP10-0116 | None Detected |
| Residual Water Analysis by Karl Fischer Coulometry | AM1346[2] | 1.79% |
| ICP-MS Analysis[3] | Outsourced | 664.0 ppm |
| Purity Factor: HPLC Assay[4] | Internal | 83.6% |
| Purity Factor: LCMS Assay[4] | Internal | 36.1% |

[1] Purity value is the average of two independent analyses
[2] Validated analytical method
[3] Counter ion to Na+ by Ion Chromatography confirmed to be Cl
[4] Assay performed by generating a 100 µg/mL solution m Methanol with 0.1N Sodium hydroxide, and comparing against a Certified Reference Standard of 100 µg/mL Methotrexate or Methotrexate-D3 in Methanol with 0.1N Sodium hydroxide.

| Purity Factor: | HPLC Assay | Check Standard | |
|---|---|---|---|
| Analysis Method: | HPLC/UV | Check Standard: | Methotrexate-D₃, Primary Standard |
| Column: | Prodigy ODS3. 5 µm. 4.6 × 250 mm | Certified Concentration: | 100.0 ± 0.9 µg/ml |
| Mobile Phase: | Acetonitrile::0.1% Phosphoric acid in Water (15::85) | | |
| Flow Rate: | 1.2 mL/min | | |
| Wavelength: | 243 nm | | |

| Sample VII | Prepared Concentration | Verified Concentration | No. of Injections | % RSD - Homogeneity |
|---|---|---|---|---|
| | 1.000 mg/mL | 83.6 µg/mL | 6 | 1.9 |

* Concentration is verified through multiple analyses and is calculated as the average of multiple analyses compared to an independently prepared check standard.

| Purity Factor: | LC/MS Assay | Check Standard 1 | |
|---|---|---|---|
| Analysis Method: | LC/MS | Check Standard: | Methotrexate Primary Standard |
| Column: | Kinetex. 2.6 µm. 2.1 × 50 mm | Certified Concentration: | 1.000 ± 0.005 mg/mL |
| Mobile Phase: | 0.1% Formic acid m Water::Acetonitrile (90:: 10) | | |
| Flow Rate: | 0.3 mL /min | | |
| Polarity: | MRM, Positive Ion | | |

| Sample VII | Prepared Concentration | Verified Concentration | No. of Injections | % RSD - Homogeneity |
|---|---|---|---|---|
| | 100 µg./mL | 36.1 µg/mL | 6 | 4.1 |

*Concentration is verified through multiple analyses and is calculated as the average of multiple analyses compared to an independently prepared check standard.

[1] Check standard diluted 1:10 from 1.000 mg/mL to 100.0 µg/mL for comparison to Sample VII.

Identity by LC/MS

| Column: | Ascentis Express Phenyl-Hexyl, 2.7 µm. 3.0 × 50 mm |
|---|---|
| Mobile Phase: | A:: 0.1% Formic Acid in Water |
| | B:: Acetonitrile |
| Flow Rate: | 0.4 mL/min |
| Scan Range: | 100-1200 amu |
| Ionization: | Electrospray. Positive Ion |
| Instrument: | Waters XEVO G2 QTOF |
| Acquired: | Jul. 15, 2015 |

-continued

| Gradient: | Time (min) | % A | % B |
|---|---|---|---|
| | 0.0 | 90 | 10 |
| | 5.0 | 70 | 30 |
| | 6.0 | 70 | 30 |
| | 6.1 | 90 | 10 |
| | 8.0 | 90 | 10 |

Isotopic Purity Evaluation by LC/MS/MS

| Column: | Kinetex, 2.6 µm, 2. | Instrument: | Agilent 6410A Mass Spectrometer |
|---|---|---|---|
| Mobile Phase: | A::0.1% Formic Acid in Water::Acetonitrile (90::10) | Acquired: | Jul. 8, 2015 |
| Flow Rate: | 0.3 mL/min | | |
| Ionization: | Electrospray, Positive Ion | | |

| Compound m/z | MRM Transition | Transition area % |
|---|---|---|
| 455 (native) | 455 » 308 | 0.00% |
| 460 (m/z for M + 5) | 460 » 314 | 0.00% |
| 461 (m/z for M + 6) | 461 » 314 | 0.00% |
| 466 (m/z for M + 11) | 466 » 314 | 0.01% |
| 469 (m/z for M + 14) | 469 » 317 | 99.99% |

Isotopic Purity by High Resolution MS

| Column: | Ascentis Express Phenyl-Hexyl, 2.7 µm, 3.0 × 50 mm |
|---|---|
| Mobile Phase: | A:: 0.1% Formic Acid in Water |
| | B:: Acetonitrile |
| Flow Rate: | 0.4 mL/min |
| Scan Range: | 455-463 amu |
| Ionization: | Electrospray, PositiveIon |
| Instrument: | Waters XEVO G2 QTOF |
| Acquired: | Jul. 15, 2015 |

| Gradient: | Time (min) | % A | % B |
|---|---|---|---|
| | 0.0 | 90 | 10 |
| | 5.0 | 70 | 30 |
| | 6.0 | 70 | 30 |
| | 6.1 | 90 | 10 |
| | 8.0 | 90 | 10 |

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

We claim:

1. A compound having the structure:

or a salt thereof;
wherein each of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ is independently selected from carbon or carbon-13; and
wherein at least 5 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

2. The compound of claim 1, wherein at least 10 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

3. The compound of claim 1, wherein at least 12 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

4. The compound of claim 1, wherein 5 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

5. The compound of claim 1, wherein 6 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

6. The compound of claim 1, wherein 11 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

7. The compound of claim 1, wherein 14 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, and $Y_{14}$ are carbon-13.

8. The compound of claim 1, wherein at least 5 of $Y_4$, $Y_5$, $Y_6$, $Y_7$, $Y_8$, and $Y_9$, are carbon-13.

9. The compound of claim 1, wherein $Y_{10}$, $Y_{11}$, $Y_{12}$, $Y_{13}$, and $Y_{14}$ are carbon-13.

10. The compound of claim 1, wherein $Y_1$, $Y_2$, and $Y_3$ are carbon-13.

11. The compound of claim 1, having the structure:

or a salt thereof.

12. The compound of claim 1, having the structure:

or a salt thereof.

13. The compound of claim 1, having the structure:

or a salt thereof.

14. The compound of claim 1, having the structure:

or a salt thereof.

* * * * *